(12) United States Patent
Feng et al.

(10) Patent No.: US 7,906,523 B2
(45) Date of Patent: *Mar. 15, 2011

(54) DIPEPTIDYL PEPTIDASE INHIBITORS

(75) Inventors: Jun Feng, Carlsbad, CA (US); Stephen L. Gwaltney, San Diego, CA (US); Jeffrey A. Stafford, San Diego, CA (US); Zhiyuan Zhang, San Diego, CA (US); Bruce J. Elder, Wynantskill, NY (US); Paul K. Isbester, Castleton, NY (US); Grant J. Palmer, Clifton Park, NY (US); Jonathon S. Salsbury, Albany, NY (US); Luckner G. Ulysse, Albany, NY (US)

(73) Assignee: Takeda Pharmaceutical Company Limited, Osaka (JP)

( * ) Notice: Subject to any disclaimer, the term of this patent is extended or adjusted under 35 U.S.C. 154(b) by 25 days.

This patent is subject to a terminal disclaimer.

(21) Appl. No.: 11/929,737

(22) Filed: Oct. 30, 2007

(65) Prior Publication Data

US 2008/0188501 A1 Aug. 7, 2008

Related U.S. Application Data

(63) Continuation of application No. 11/080,992, filed on Mar. 15, 2005.

(60) Provisional application No. 60/553,571, filed on Mar. 15, 2004, provisional application No. 60/629,524, filed on Nov. 18, 2004.

(51) Int. Cl.
*C07D 401/04* (2006.01)
*A61K 31/506* (2006.01)
*A61P 3/10* (2006.01)
*A61P 19/02* (2006.01)
*A61P 35/00* (2006.01)

(52) U.S. Cl. ............ 514/274; 544/312; 544/309

(58) Field of Classification Search ............. 544/309, 544/312, 274; 514/274
See application file for complete search history.

(56) References Cited

U.S. PATENT DOCUMENTS

| | | | |
|---|---|---|---|
| 3,322,756 A | 5/1967 | Hilmer et al. |
| 3,544,570 A | 12/1970 | Timmler et al. |
| 3,823,135 A | 7/1974 | Pilgram et al. |
| 3,960,949 A | 6/1976 | Ahrens et al. |
| 4,494,978 A | 1/1985 | Chan |
| 4,935,493 A | 6/1990 | Bachovchin et al. |
| 5,366,862 A | 11/1994 | Venton et al. |
| 5,387,512 A | 2/1995 | Balani et al. |
| 5,433,955 A | 7/1995 | Bredehorst et al. |
| 5,462,928 A | 10/1995 | Bachovchin et al. |
| 5,512,549 A | 4/1996 | Chen et al. |
| 5,543,396 A | 8/1996 | Powers et al. |
| 5,580,979 A | 12/1996 | Bachovchin |
| 5,601,986 A | 2/1997 | Takacs |
| 5,614,379 A | 3/1997 | MacKellar |
| 5,614,492 A | 3/1997 | Habener |
| 5,624,894 A | 4/1997 | Bodor |
| 5,798,344 A | 8/1998 | Kuroki et al. |
| 5,811,278 A | 9/1998 | Okamura et al. |
| 5,811,281 A | 9/1998 | Quaroni et al. |
| 5,814,460 A | 9/1998 | Venton et al. |
| 5,885,997 A | 3/1999 | Lohray et al. |
| 5,939,560 A | 8/1999 | Jenkins et al. |
| 5,965,532 A | 10/1999 | Bachovchin |
| 5,985,884 A | 11/1999 | Lohray et al. |
| 6,006,753 A | 12/1999 | Efendic |
| 6,011,155 A | 1/2000 | Villhauer |
| 6,090,786 A | 7/2000 | Augustyns et al. |
| 6,107,317 A | 8/2000 | Villhauer |
| 6,110,949 A | 8/2000 | Villhauer |
| 6,124,305 A | 9/2000 | Villhauer |
| 6,129,911 A | 10/2000 | Faris |
| 6,156,739 A | 12/2000 | Griffin et al. |
| 6,166,063 A | 12/2000 | Villhauer |
| 6,172,081 B1 | 1/2001 | Damon |
| 6,184,020 B1 | 2/2001 | Blinkovsky et al. |
| 6,201,132 B1 | 3/2001 | Jenkins et al. |
| 6,214,340 B1 | 4/2001 | Takeuchi et al. |
| 6,235,493 B1 | 5/2001 | Bissell et al. |
| 6,251,391 B1 | 6/2001 | Wilkinson et al. |
| 6,258,597 B1 | 7/2001 | Bachovchin et al. |

(Continued)

FOREIGN PATENT DOCUMENTS

BR 699812 11/1950

(Continued)

OTHER PUBLICATIONS

Marcus et al. PubMed Abstract (Intervirology, 45/4-6):260-6) 2002.

(Continued)

*Primary Examiner* — Venkataraman Balasubramanian
(74) *Attorney, Agent, or Firm* — Mitchell R. Brustein

(57) ABSTRACT

Compounds, pharmaceuticals, kits and methods are provided for use with DPP-IV and other S9 proteases that comprise a compound comprising:

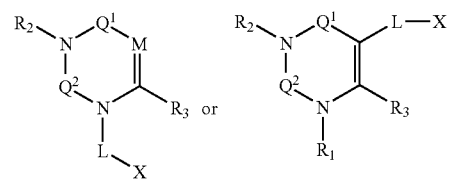

wherein M is N or $CR_4$; $Q^1$ and $Q^2$ are each independently selected from the group consisting of CO, SO, $SO_2$, and $C=NR_9$; and each L, X, $R_1$, $R_2$, and $R_3$ are as defined herein.

15 Claims, 1 Drawing Sheet

U.S. PATENT DOCUMENTS

| | | |
|---|---|---|
| 6,261,794 B1 | 7/2001 | Chang |
| 6,265,551 B1 | 7/2001 | Duke-Cohan et al. |
| 6,303,661 B1 | 10/2001 | Demuth et al. |
| 6,309,868 B1 | 10/2001 | Monod et al. |
| 6,310,069 B1 | 10/2001 | Lohray et al. |
| 6,319,893 B1 | 11/2001 | Demuth et al. |
| 6,325,989 B1 | 12/2001 | Duke-Cohan et al. |
| 6,335,429 B1 | 1/2002 | Cai et al. |
| 6,337,069 B1 | 1/2002 | Grouzmann et al. |
| 6,342,611 B1 | 1/2002 | Weber et al. |
| 6,355,614 B1 | 3/2002 | Wallner |
| 6,380,398 B2 | 4/2002 | Kanstrup et al. |
| 6,395,767 B2 | 5/2002 | Robl et al. |
| 6,432,969 B1 | 8/2002 | Villhauer |
| 6,447,772 B1 | 9/2002 | Houston |
| 6,448,045 B1 | 9/2002 | Levine et al. |
| 6,458,924 B2 | 10/2002 | Knudsen et al. |
| 6,485,955 B1 | 11/2002 | Huber et al. |
| 6,495,544 B2 | 12/2002 | Moormann et al. |
| 6,500,804 B2 | 12/2002 | Demuth et al. |
| 6,518,277 B1 | 2/2003 | Sadhu et al. |
| 6,521,644 B1 | 2/2003 | Broqua |
| 6,528,486 B1 | 3/2003 | Larsen et al. |
| 6,545,170 B2 | 4/2003 | Pitzele et al. |
| 6,548,481 B1 | 4/2003 | Demuth et al. |
| 6,548,529 B1 | 4/2003 | Robl et al. |
| 6,555,519 B2 | 4/2003 | Washburn |
| 6,555,521 B2 | 4/2003 | Hermeling et al. |
| 6,559,188 B1 | 5/2003 | Gatlin et al. |
| 6,573,096 B1 | 6/2003 | Chen |
| 6,573,287 B2 | 6/2003 | Sulsky et al. |
| 6,586,198 B2 | 7/2003 | Brown |
| 6,608,038 B2 | 8/2003 | Caplan et al. |
| 6,617,340 B1 | 9/2003 | Villhauer |
| 6,620,821 B2 | 9/2003 | Robl |
| 6,620,910 B1 | 9/2003 | Calas et al. |
| 6,627,636 B2 | 9/2003 | Robl |
| 6,645,995 B2 | 11/2003 | Kanstrup et al. |
| 6,664,273 B2 | 12/2003 | Burnett et al. |
| 6,673,815 B2 | 1/2004 | Devasthale et al. |
| 6,673,829 B2 | 1/2004 | Dorwald et al. |
| 6,686,337 B2 | 2/2004 | Connor |
| 6,699,871 B2 | 3/2004 | Edmondson et al. |
| 6,703,238 B2 | 3/2004 | Bachovchin et al. |
| 6,706,742 B2 | 3/2004 | De Nanteuil et al. |
| 6,710,040 B1 | 3/2004 | Hulin et al. |
| 6,716,843 B2 | 4/2004 | De Nanteuil et al. |
| 6,727,261 B2 | 4/2004 | Gobbi et al. |
| 6,727,271 B2 | 4/2004 | Cheng et al. |
| 6,761,440 B2 | 7/2004 | Chou et al. |
| 6,800,650 B2 | 10/2004 | Boehringer et al. |
| 6,803,357 B1 | 10/2004 | Bachovchin et al. |
| 6,825,169 B1 | 11/2004 | Bachovchin et al. |
| 6,867,205 B2 | 3/2005 | Boehringer et al. |
| 7,230,000 B1 | 6/2007 | Finer et al. |
| 2001/0018210 A1 | 8/2001 | Bachovchin et al. |
| 2001/0020006 A1 | 9/2001 | Demuth et al. |
| 2001/0031780 A1 | 10/2001 | Kanstrup et al. |
| 2001/0047078 A1 | 11/2001 | Chang |
| 2001/0051646 A1 | 12/2001 | Demuth et al. |
| 2002/0006899 A1 | 1/2002 | Pospisilik et al. |
| 2002/0016100 A1 | 2/2002 | Okabe et al. |
| 2002/0019411 A1 | 2/2002 | Robl et al. |
| 2002/0037829 A1 | 3/2002 | Aronson et al. |
| 2002/0041871 A1 | 4/2002 | Brudnak |
| 2002/0049153 A1 | 4/2002 | Bridon et al. |
| 2002/0049164 A1 | 4/2002 | Demuth et al. |
| 2002/0061839 A1 | 5/2002 | Scharpe et al. |
| 2002/0071838 A1 | 6/2002 | Demuth et al. |
| 2002/0077340 A1 | 6/2002 | Sulsky et al. |
| 2002/0082292 A1 | 6/2002 | Sahoo et al. |
| 2002/0082427 A1 | 6/2002 | Demuth et al. |
| 2002/0103242 A1 | 8/2002 | Sahoo et al. |
| 2002/0103384 A1 | 8/2002 | Kanstrup et al. |
| 2002/0110560 A1 | 8/2002 | Demuth et al. |
| 2002/0115843 A1 | 8/2002 | Oi et al. |
| 2002/0132979 A1 | 9/2002 | Chen |
| 2002/0147130 A1 | 10/2002 | Huber et al. |
| 2002/0147157 A1 | 10/2002 | Connor |
| 2002/0155565 A1 | 10/2002 | Garin-Chesa et al. |
| 2002/0164759 A1 | 11/2002 | Travis et al. |
| 2002/0165164 A1 | 11/2002 | Demuth et al. |
| 2002/0169159 A1 | 11/2002 | Medina et al. |
| 2002/0183367 A1 | 12/2002 | Sulsky et al. |
| 2002/0193390 A1 | 12/2002 | Villhauer |
| 2002/0198205 A1 | 12/2002 | Himmelsbach et al. |
| 2002/0198242 A1 | 12/2002 | Demuth et al. |
| 2003/0008905 A1 | 1/2003 | Demuth et al. |
| 2003/0008925 A1 | 1/2003 | Esteve et al. |
| 2003/0027282 A1 | 2/2003 | Huber et al. |
| 2003/0040478 A1 | 2/2003 | Drucker et al. |
| 2003/0045464 A1 | 3/2003 | Hermeling et al. |
| 2003/0055052 A1 | 3/2003 | Peters et al. |
| 2003/0060412 A1 | 3/2003 | Prouty et al. |
| 2003/0060434 A1 | 3/2003 | Nielsen et al. |
| 2003/0069234 A1 | 4/2003 | Medina et al. |
| 2003/0087935 A1 | 5/2003 | Cheng et al. |
| 2003/0087950 A1 | 5/2003 | DeNanteuil et al. |
| 2003/0089935 A1 | 5/2003 | Fan et al. |
| 2003/0092630 A2 | 5/2003 | Demuth et al. |
| 2003/0092697 A1 | 5/2003 | Cheng et al. |
| 2003/0096846 A1 | 5/2003 | Cheng et al. |
| 2003/0096857 A1 | 5/2003 | Evans et al. |
| 2003/0100563 A1 | 5/2003 | Edmondson et al. |
| 2003/0103968 A1 | 6/2003 | Amelsberg et al. |
| 2003/0105077 A1 | 6/2003 | Kanstrup et al. |
| 2003/0119736 A1 | 6/2003 | Demuth et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0130199 A1 | 7/2003 | von Hoersten et al. |
| 2003/0130281 A1 | 7/2003 | Boehringer et al. |
| 2003/0130306 A1 | 7/2003 | Devasthale et al. |
| 2003/0134802 A1 | 7/2003 | Demuth et al. |
| 2003/0135023 A1 | 7/2003 | Demuth et al. |
| 2003/0139429 A1 | 7/2003 | Cohen |
| 2003/0139434 A1 | 7/2003 | Balkan et al. |
| 2003/0144206 A1 | 7/2003 | Knudsen et al. |
| 2003/0148961 A1 | 8/2003 | Heiser et al. |
| 2003/0149071 A1 | 8/2003 | Gobbi et al. |
| 2003/0153509 A1 | 8/2003 | Bachovchin et al. |
| 2003/0162820 A1 | 8/2003 | Demuth et al. |
| 2003/0166578 A1 | 9/2003 | Arch et al. |
| 2003/0166662 A1 | 9/2003 | Fryburg et al. |
| 2003/0166690 A1 | 9/2003 | Ebdrup et al. |
| 2003/0171358 A1 | 9/2003 | Jeppesen et al. |
| 2003/0171411 A1 | 9/2003 | Kodra et al. |
| 2003/0176357 A1 | 9/2003 | Pospisilik et al. |
| 2003/0181497 A1 | 9/2003 | Chen et al. |
| 2003/0186963 A1 | 10/2003 | Dorwald et al. |
| 2003/0187254 A1 | 10/2003 | Perry et al. |
| 2003/0191112 A1 | 10/2003 | Dorwald et al. |
| 2003/0195188 A1 | 10/2003 | Boehringer et al. |
| 2003/0195190 A1 | 10/2003 | Peschke et al. |
| 2003/0199451 A1 | 10/2003 | Mogensen et al. |
| 2003/0199528 A1 | 10/2003 | Kanstrup et al. |
| 2003/0199563 A1 | 10/2003 | Robl et al. |
| 2003/0199672 A1 | 10/2003 | Knudsen et al. |
| 2003/0203946 A1 | 10/2003 | Behrens et al. |
| 2003/0216382 A1 | 11/2003 | Boehringer et al. |
| 2003/0216450 A1 | 11/2003 | Evans et al. |
| 2003/0220345 A1 | 11/2003 | Hamby et al. |
| 2003/0225102 A1 | 12/2003 | Sankaranarayanan |
| 2003/0232761 A1 | 12/2003 | Hinke et al. |
| 2003/0236272 A1 | 12/2003 | Carr |
| 2004/0002495 A1 | 1/2004 | Sher et al. |
| 2004/0002609 A1 | 1/2004 | Hulin |
| 2004/0006062 A1 | 1/2004 | Smallheer et al. |
| 2004/0009972 A1 | 1/2004 | Ding et al. |
| 2004/0009998 A1 | 1/2004 | Dhar et al. |
| 2004/0034014 A1 | 2/2004 | Kanstrup et al. |
| 2004/0053369 A1 | 3/2004 | Abbott et al. |
| 2004/0054171 A1 | 3/2004 | Jensen et al. |
| 2004/0058876 A1 | 3/2004 | Hoffmann et al. |
| 2004/0063935 A1 | 4/2004 | Yasuda |
| 2004/0072874 A1 | 4/2004 | Sato et al. |
| 2004/0072892 A1 | 4/2004 | Fukushima et al. |

| | | | | | | |
|---|---|---|---|---|---|---|
| 2004/0077645 A1 | 4/2004 | Himmelsbach et al. | EP | 0 442 473 A | 8/1991 | |
| 2004/0082497 A1 | 4/2004 | Evans et al. | EP | 0505893 | 9/1992 | |
| 2004/0082607 A1 | 4/2004 | Oi et al. | EP | 0547442 A1 | 6/1993 | |
| 2004/0087587 A1 | 5/2004 | Himmelsbach et al. | EP | 0547514 | 6/1993 | |
| 2004/0092478 A1 | 5/2004 | Rothermel et al. | EP | 0574846 | 12/1993 | |
| 2004/0097510 A1 | 5/2004 | Himmelsbach et al. | EP | 0587377 A2 | 3/1994 | |
| 2004/0106655 A1 | 6/2004 | Kitajima et al. | EP | 0657452 | 6/1995 | |
| 2004/0106656 A1 | 6/2004 | Ashton et al. | EP | 0702013 | 3/1996 | |
| 2004/0106802 A1 | 6/2004 | Sankaranarayanan | EP | 900568 A2 | 3/1999 | |
| 2004/0110817 A1 | 6/2004 | Hulin | EP | 900568 A2 | 10/1999 | |
| 2004/0116328 A1 | 6/2004 | Yoshikawa et al. | EP | 1136482 A1 | 9/2001 | |
| 2004/0132713 A1 | 7/2004 | Hulin et al. | EP | 1197799 A1 | 4/2002 | |
| 2004/0132732 A1 | 7/2004 | Han et al. | FR | 2.162.106 | 11/1972 | |
| 2004/0138148 A1 | 7/2004 | Fushimi et al. | GB | 1377642 | 12/1974 | |
| 2004/0138214 A1 | 7/2004 | Himmelsbach et al. | GB | 1441665 A | 7/1976 | |
| 2004/0138215 A1 | 7/2004 | Eckhardt et al. | GB | 1464248 A | 2/1977 | |
| 2004/0147434 A1 | 7/2004 | Ansorge et al. | GB | 2143542 A | 2/1985 | |
| 2004/0152192 A1 | 8/2004 | Bachovchin et al. | GB | 2230527 A | 10/1990 | |
| 2004/0152745 A1 | 8/2004 | Jackson et al. | JP | 9295977 | 11/1997 | |
| 2004/0166125 A1 | 8/2004 | Himmelsbach et al. | JP | 2002/338466 | 11/2002 | |
| 2004/0167133 A1 | 8/2004 | Edmondson et al. | JP | 2003/128551 | 5/2003 | |
| 2004/0167191 A1 | 8/2004 | Demuth et al. | JP | 2004/99600 A | 4/2004 | |
| 2004/0167341 A1 | 8/2004 | Haffner et al. | JP | 2004/123738 A | 4/2004 | |
| 2004/0171104 A1 | 9/2004 | Blinkovsky et al. | KM | 53005180 A | 1/1978 | |
| 2004/0171555 A1 | 9/2004 | Demuth et al. | WO | WO 89/10701 | 11/1989 | |
| 2004/0171848 A1 | 9/2004 | Haffner et al. | WO | WO 91/11457 | 8/1991 | |
| 2004/0176406 A1 | 9/2004 | Gobbi et al. | WO | WO 91/12001 | 8/1991 | |
| 2004/0176428 A1 | 9/2004 | Edmondson et al. | WO | WO 93/21162 | 1/1993 | |
| 2004/0180925 A1 | 9/2004 | Matsuno et al. | WO | WO 93/08259 A2 | 4/1993 | |
| 2004/0186153 A1 | 9/2004 | Yasuda et al. | WO | WO 93/08259 A3 | 4/1993 | |
| 2004/0198786 A1 | 10/2004 | Gretzke et al. | WO | WO 94/03055 | 2/1994 | |
| 2004/0209891 A1 | 10/2004 | Broqua et al. | WO | WO 95/15309 | 6/1995 | |
| 2004/0229820 A1 | 11/2004 | Bachovchin et al. | WO | WO 95/29691 | 11/1995 | |
| 2004/0229848 A1 | 11/2004 | Demuth et al. | WO | WO 95/35031 | 12/1995 | |
| 2004/0236102 A1 | 11/2004 | Brockunier et al. | WO | WO 96/02667 | 2/1996 | |
| 2004/0242566 A1 | 12/2004 | Feng et al. | WO | WO 96/32384 | 10/1996 | |
| 2004/0242568 A1 | 12/2004 | Feng et al. | WO | WO 96/38550 | 12/1996 | |
| 2004/0242636 A1 | 12/2004 | Haffner et al. | WO | WO 97/40832 | 11/1997 | |
| 2004/0242898 A1 | 12/2004 | Hulin | WO | WO 98/00439 | 1/1998 | |
| 2004/0254167 A1 | 12/2004 | Biftu et al. | WO | WO 98/18763 | 5/1998 | |
| 2004/0254226 A1 | 12/2004 | Feng et al. | WO | WO 98/19998 | 5/1998 | |
| 2004/0259843 A1 | 12/2004 | Madar et al. | WO | WO 98/24780 | 6/1998 | |
| 2004/0259870 A1 | 12/2004 | Feng et al. | WO | WO 98/50046 | 11/1998 | |
| 2004/0259883 A1 | 12/2004 | Sakashita et al. | WO | WO 98/51803 | 11/1998 | |
| 2004/0259902 A1 | 12/2004 | Boehringer et al. | WO | WO 99/02705 | 1/1999 | |
| 2004/0259903 A1 | 12/2004 | Boehringer et al. | WO | WO 99/16864 | 4/1999 | |
| 2004/0259919 A1 | 12/2004 | Magnin et al. | WO | WO 99/17799 | 4/1999 | |
| 2005/0014732 A1 | 1/2005 | Gulve et al. | WO | WO 99/18856 | 4/1999 | |
| 2005/0014946 A1 | 1/2005 | Demuth et al. | WO | WO 99/28474 | 6/1999 | |
| 2005/0020574 A1 | 1/2005 | Hauel et al. | WO | WO 99/38501 | 8/1999 | |
| 2005/0026921 A1 | 2/2005 | Eckhardt et al. | WO | WO 99/46272 | 9/1999 | |
| 2005/0032804 A1 | 2/2005 | Cypes et al. | WO | WO 99/47152 | 9/1999 | |
| 2005/0038020 A1 | 2/2005 | Hamann et al. | WO | WO 99/50249 | 10/1999 | |
| 2005/0043292 A1 | 2/2005 | Parker et al. | WO | WO 99/61431 | 12/1999 | |
| 2005/0043299 A1 | 2/2005 | Evans et al. | WO | WO 99/62914 | 12/1999 | |
| 2005/0058635 A1 | 3/2005 | Demuth et al. | WO | WO 99/67278 | 12/1999 | |
| 2005/0065144 A1 | 3/2005 | Feng et al. | WO | WO 99/67279 | 12/1999 | |
| 2005/0065145 A1 | 3/2005 | Cao et al. | WO | WO 00/07617 | 2/2000 | |
| 2005/0065148 A1 | 3/2005 | Feng et al. | WO | WO 00/09666 | 2/2000 | |
| 2005/0070350 A1 | 3/2005 | McVay | WO | WO 00/10549 | 3/2000 | |
| 2005/0070531 A1 | 3/2005 | Feng et al. | WO | WO 00/15211 | 3/2000 | |
| 2005/0070535 A1 | 3/2005 | Feng et al. | WO | WO 00/20416 | 4/2000 | |
| 2005/0070706 A1 | 3/2005 | Feng et al. | WO | WO 00/76986 A1 | 4/2000 | |
| 2005/0075330 A1 | 4/2005 | Feng et al. | WO | WO 00/34241 | 6/2000 | |
| 2006/0135767 A1 | 6/2006 | Feng et al. | WO | WO 00/40583 | 7/2000 | |
| 2007/0060528 A1 | 3/2007 | Christopher et al. | WO | WO 00/43366 | 7/2000 | |
| 2007/0060530 A1 | 3/2007 | Christopher et al. | WO | WO 00/47219 | 8/2000 | |
| 2007/0066635 A1 | 3/2007 | Andres et al. | WO | WO 00/53171 | 9/2000 | |
| 2008/0003283 A1 | 1/2008 | Feng et al. | WO | WO 00/56296 | 9/2000 | |
| 2008/0108807 A1 | 5/2008 | Feng et al. | WO | WO 00/56297 | 9/2000 | |
| 2008/0108808 A1 | 5/2008 | Feng et al. | WO | WO 00/57721 | 10/2000 | |
| | | | WO | WO 01/14318 A2 | 3/2001 | |
| FOREIGN PATENT DOCUMENTS | | | WO | WO 01/16301 | 3/2001 | |
| DE | 21 50 686 A1 | 4/1973 | WO | WO 01/19866 | 3/2001 | |
| DE | 2361551 A1 | 6/1975 | WO | WO 01/23364 A1 | 4/2001 | |
| DE | 2500024 A1 | 7/1976 | WO | WO 01/34594 A1 | 5/2001 | |
| DE | 2801289 A1 | 5/1979 | WO | WO 01/40180 | 6/2001 | |
| DE | 10256264 A | 6/2004 | WO | WO 01/52825 A2 | 7/2001 | |
| EP | 0378255 A2 | 7/1990 | WO | WO 01/55105 | 8/2001 | |

| | | | | | | |
|---|---|---|---|---|---|---|
| WO | WO 01/56988 A1 | 8/2001 | | WO | WO 2003035640 A1 | 5/2003 |
| WO | WO 01/62266 | 8/2001 | | WO | WO 03/045228 A2 | 6/2003 |
| WO | WO 01/68603 | 9/2001 | | WO | WO 03/045977 A2 | 6/2003 |
| WO | WO 01/70729 A1 | 9/2001 | | WO | WO 03/048081 A2 | 6/2003 |
| WO | WO 01/72290 | 10/2001 | | WO | WO 03/048158 A1 | 6/2003 |
| WO | WO 01/74299 | 10/2001 | | WO | WO 03/051848 | 6/2003 |
| WO | WO 01/79206 | 10/2001 | | WO | WO 03/055881 | 7/2003 |
| WO | WO 01/81304 | 11/2001 | | WO | WO 03/057144 | 7/2003 |
| WO | WO 01/81337 | 11/2001 | | WO | WO 03/057200 A2 | 7/2003 |
| WO | WO 01/89569 | 11/2001 | | WO | WO 03/057666 | 7/2003 |
| WO | WO 01/94597 | 12/2001 | | WO | WO 03/063903 A2 | 8/2003 |
| WO | WO 01/96295 A2 | 12/2001 | | WO | WO 03/065983 | 8/2003 |
| WO | WO 01/97808 A1 | 12/2001 | | WO | WO 03/068748 | 8/2003 |
| WO | WO 02/02560 A2 | 1/2002 | | WO | WO 03/068757 | 8/2003 |
| WO | WO 02/04610 | 1/2002 | | WO | WO 03/072197 | 9/2003 |
| WO | WO 02/08931 | 1/2002 | | WO | WO 03/072556 A1 | 9/2003 |
| WO | WO 02/09716 A | 2/2002 | | WO | WO 03/074500 | 9/2003 |
| WO | WO 02/14271 | 2/2002 | | WO | WO 03/076393 | 9/2003 |
| WO | WO 02/20488 A2 | 3/2002 | | WO | WO 03/076414 | 9/2003 |
| WO | WO 02/20804 | 3/2002 | | WO | WO 03/076418 A1 | 9/2003 |
| WO | WO 02/26703 | 4/2002 | | WO | WO 03/077935 | 9/2003 |
| WO | WO 02/28742 | 4/2002 | | WO | WO 03/080070 | 10/2003 |
| WO | WO 02/30890 | 4/2002 | | WO | WO 03/080633 | 10/2003 |
| WO | WO 02/30891 | 4/2002 | | WO | WO 03/082817 | 10/2003 |
| WO | WO 02/31134 | 4/2002 | | WO | WO 03/082859 | 10/2003 |
| WO | WO 02/34242 A2 | 5/2002 | | WO | WO 03/082898 A2 | 10/2003 |
| WO | WO 02/34243 A2 | 5/2002 | | WO | WO 03/084940 | 10/2003 |
| WO | WO 02/34900 | 5/2002 | | WO | WO 03/092605 A2 | 11/2003 |
| WO | WO 02/38541 | 5/2002 | | WO | WO 03/099279 A1 | 12/2003 |
| WO | WO 02/38742 | 5/2002 | | WO | WO 03/099286 | 12/2003 |
| WO | WO 02/051836 | 7/2002 | | WO | WO 03/099818 A1 | 12/2003 |
| WO | WO 02/053170 | 7/2002 | | WO | WO 03/101449 | 12/2003 |
| WO | WO 02/059301 | 8/2002 | | WO | WO 03/101958 | 12/2003 |
| WO | WO 02/059343 | 8/2002 | | WO | WO 03/104207 | 12/2003 |
| WO | WO 02/062764 | 8/2002 | | WO | WO 03/104208 | 12/2003 |
| WO | WO 02/066627 | 8/2002 | | WO | WO 03/104229 | 12/2003 |
| WO | WO 02/068420 | 9/2002 | | WO | WO 03/106416 A2 | 12/2003 |
| WO | WO 02/076450 | 10/2002 | | WO | WO 03/106456 | 12/2003 |
| WO | WO 02/083109 A1 | 10/2002 | | WO | WO 2004/002535 | 1/2004 |
| WO | WO 02/083128 | 10/2002 | | WO | WO 2004/002986 | 1/2004 |
| WO | WO 02/092127 | 11/2002 | | WO | WO 2004/004655 | 1/2004 |
| WO | WO 02/096357 | 12/2002 | | WO | WO 2004/004661 | 1/2004 |
| WO | WO 03/000180 | 1/2003 | | WO | WO 2004/004665 | 1/2004 |
| WO | WO 03/000181 A2 | 1/2003 | | WO | WO 2004/007446 | 1/2004 |
| WO | WO 03/000250 | 1/2003 | | WO | WO 2004/007468 | 1/2004 |
| WO | WO 03/002530 | 1/2003 | | WO | WO 2004/011640 | 2/2004 |
| WO | WO 03/002531 | 1/2003 | | WO | WO 2004/014860 | 2/2004 |
| WO | WO 03/002553 | 1/2003 | | WO | WO 2004/017989 A1 | 3/2004 |
| WO | WO 03/002593 A2 | 1/2003 | | WO | WO 2004/018467 | 3/2004 |
| WO | WO 03/002595 A2 | 1/2003 | | WO | WO 2004/018468 | 3/2004 |
| WO | WO 03/002596 A2 | 1/2003 | | WO | WO 2004/018469 | 3/2004 |
| WO | WO 03/004496 | 1/2003 | | WO | WO 2004/020407 | 3/2004 |
| WO | WO 03/004498 | 1/2003 | | WO | WO 2004/024184 | 3/2004 |
| WO | WO 03/007888 A2 | 1/2003 | | WO | WO 2004/026822 | 4/2004 |
| WO | WO 03/010197 | 2/2003 | | WO | WO 2004/028524 | 4/2004 |
| WO | WO 03/010314 | 2/2003 | | WO | WO 2004/031175 | 4/2004 |
| WO | WO 03/011807 | 2/2003 | | WO | WO 2004/031374 A2 | 4/2004 |
| WO | WO 03/011814 | 2/2003 | | WO | WO 2004/032836 | 4/2004 |
| WO | WO 03/011834 | 2/2003 | | WO | WO 2004/032861 | 4/2004 |
| WO | WO 03/011892 | 2/2003 | | WO | WO 2004/033455 | 4/2004 |
| WO | WO 03/014318 | 2/2003 | | WO | WO 2004/037169 | 5/2004 |
| WO | WO 03/015775 | 2/2003 | | WO | WO 2004/037176 A2 | 5/2004 |
| WO | WO 03/016335 A2 | 2/2003 | | WO | WO 2004/037181 | 5/2004 |
| WO | WO 03/002287 A2 | 3/2003 | | WO | WO 2004/041795 | 5/2004 |
| WO | WO 03/017936 | 3/2003 | | WO | WO 2004/043940 | 5/2004 |
| WO | WO 03/024942 | 3/2003 | | WO | WO 2004/046106 | 6/2004 |
| WO | WO 03/024965 | 3/2003 | | WO | WO 2004/048352 | 6/2004 |
| WO | WO 03/053330 | 3/2003 | | WO | WO 2004/050022 | 6/2004 |
| WO | WO 03/026652 A1 | 4/2003 | | WO | WO 2004/050656 | 6/2004 |
| WO | WO 03/027080 A1 | 4/2003 | | WO | WO 2004/050658 | 6/2004 |
| WO | WO 03/030946 A1 | 4/2003 | | WO | WO 2004/052850 | 6/2004 |
| WO | WO 03/033524 A2 | 4/2003 | | WO | WO 2004/058266 | 7/2004 |
| WO | WO 03/035057 A | 5/2003 | | WO | WO 2004/062613 A2 | 7/2004 |
| WO | WO 03/035067 | 5/2003 | | WO | WO 2004/064778 | 8/2004 |
| WO | WO 03/037327 | 5/2003 | | WO | WO 2004/067509 | 8/2004 |
| WO | WO 03/037888 A1 | 5/2003 | | WO | WO 2004/069162 | 8/2004 |
| WO | WO 03/038123 | 5/2003 | | WO | WO 2004/071454 | 8/2004 |
| WO | WO 03/040114 | 5/2003 | | WO | WO 2004/075815 | 9/2004 |
| WO | WO 03/040174 A2 | 5/2003 | | WO | WO 2004/075891 | 9/2004 |

| | | |
|---|---|---|
| WO | WO 2004/076401 | 9/2004 |
| WO | WO 2004/076433 | 9/2004 |
| WO | WO 2004/076434 | 9/2004 |
| WO | WO 2004/078777 | 9/2004 |
| WO | WO 2004/080958 | 9/2004 |
| WO | WO 2004/083212 | 9/2004 |
| WO | WO 2004/085408 A1 | 10/2004 |
| WO | WO 2004/085661 | 10/2004 |
| WO | WO 2004/087053 | 10/2004 |
| WO | WO 2004/087650 | 10/2004 |
| WO | WO 2004/087880 | 10/2004 |
| WO | WO 2004/089362 | 10/2004 |
| WO | WO 2004/096806 | 11/2004 |
| WO | WO 2004/098625 | 11/2004 |
| WO | WO 2004/099134 | 11/2004 |
| WO | WO 2004/099185 | 11/2004 |
| WO | WO 2004/101514 | 11/2004 |
| WO | WO 2004/103276 | 12/2004 |
| WO | WO 2004/103993 | 12/2004 |
| WO | WO 2004/110436 | 12/2004 |
| WO | WO 2004/111041 | 12/2004 |
| WO | WO 2004/111051 | 12/2004 |
| WO | WO 2004/112701 | 12/2004 |
| WO | WO 2005/000846 | 1/2005 |
| WO | WO 2005/000848 | 1/2005 |
| WO | WO 2005/003135 | 1/2005 |
| WO | WO 2005/011581 | 2/2005 |
| WO | WO 2005/012249 | 2/2005 |
| WO | WO 2005/016911 | 2/2005 |
| WO | WO 2005/019168 | 3/2005 |
| WO | WO 2005/095381 | 10/2005 |

OTHER PUBLICATIONS

Van Heeswijk et al., PubMed Abstract (Antivir Ther. 6(4);2001-29) Dec. 2001.
Wolf Manfred E. "Burger's Medicinal Chemistry, 5ed, Part 1" John Wiley and Sons, 1995, pp. 975-977.
Banker, G.S. et al, "Modern Pharmaceutices, 3rd edition", Marcel Dekker, New York, 1996, pp. 451 and 596.
West, Antony R., Solid State Chemistry and its Applictions, Wile, New York, 1988, pp. 358 & 365.
Vippagunta et al, Advanced Drug Delivery Reviews 48: 3-26, 2001.
Cecil Textbook of Medicine, edited by Bennet, J.C., and Plum F., 20th edition, vol. 1, 1004-10, 1996.
Green et al., Expert Opin. Emergin Drugs, 11(3); 525-539, 2006.
Mall et al. Reactivity Difference of Cis-Trans Pairs: Differnt Behavior of Stillbene Oxides and Activates Stibene Imines, 1987, Journal of Organic Chemistry, 1987, vol. 52, pp. 4812-4814.
Abdel-Fattah et al. Indian Journal of Heterocyclic Chemistry (1999), 8(3), 177-182. (Abstract, 2 pages).
Abdel-Rahman, R. M.: Synthesis of some new fluorine bearing trisubstituted 3-thioxo-1, 2, 4-triazin-5-ones as potential anticancer agents: Farmaco, Edizione Scientifica, Societa Chimica Italiana, Pavia, IT, vol. 47, No. 3 (Mar. 1992), pp. 319-326, XP008000322.
Abstract of Barnickel et al. that shows the prior art compounds (one page), Apr. 5, 2001.
Abstract of EP 900568 that shows the prior art compounds (three pages), Mar. 10, 1999.
Abstract of Lakhan et al. Journal of Indian Chemical Society (1987), 64 (5), 316-18 (2 pages).
Abstract of Pattanaik et al. Indian Journal of Chemistry, Section B; Organic Chemistry including Medicinal Chemistry (1998), 37B (12), 1304-1306. (three pages).
Abstract of Shyam et al. Current Science (1975), 44(16), 572-4 (one page).
Abstract of Tiwari et al. Indian of Journal of Pharmaceutical Sciences (1978), 40(2), 40-3 (2 pages).
Adel Hamid et al. Scientia Pharmaceutica (2001), 69(4), 351-366.
Akahoshi, F. et al.: "Synthesis and pharmacological activitey of triazolo[1,5-a]triazine derivatives inhibiting eosinophilia." Journal of Medicinal Chemistry, vol. 41, No. 16, (Jul. 30, 1998), pp. 2985-2993, XP002390903.
An abstract of Pattanaik et al. Indian Journal of Chemistry, Section B; Organic Chemistry including Medicinal Chemistry (1998), 37B (12), 1304-1306 from STN CAS online search printout (3 pages).

Argaud, Doriane et al., Metaformin decreases gluconeogenesis by enhancing the pyruvate kinase flux in isolated rat hepatocytes, European J. Biochem. 213, 1341-1348 (1993).
Ashcroft, Stephen J.H. et al., Structure-activity relationships of alloxan-like compounds derived from uric acid, Br. J. Pharmac. (1986), 89 pp. 469-472.
Baker, B.R. et al., Irreversible Enzyme Inhibitors. On the Mode of Pyrimidine Binding of 5-alkyl and 5-Arylpyrimidines to Dihydrofolic Reductase (1,2), Journal of Heterocyclic Chemistry vol. 4 (1967) pp. 39-48.
Bal, Gunther, Dipeptidyl Peptidase IV and Prolyl Oligopeptidase: Design, Synthesis and Evaluation of Substrates and Inhibitors, (2002) Universiteit Antwerpen.
Barakat, S.E.S., Synthesis and hypoglycemic activity of some new 3-[4- [[[(cyclohexylamino) carbonyl] amino]sulfony]phenyl]-4(3H)-quinazolinones, Az. J. Pharm. Sci., vol. 25, (2000), pp. 48-57.
Barakat, S.E.S., Synthesis and Hypoglycemic Activity of Some New 4(3H)—Quinazolinone Analogues, Saudi Pharmaceutical Journal, vol. 8, No. 4 (2000) pp. 198-204.
Barnela et al. Indian Journal of Chemistry Section B: Organic Chemistry Including Medicinal Chemistry (1986), 25B(7), 709-11. (Abstract 2 pages).
Belgodere, Elena et al., Synthesis of Substituted Pyrimidines, Study of the Structure and of the Tautomeric Equilibria, (1976) Chem. Abstracts, Columbus, OH vol. 85 No. 9.
Bezuglyi, P.O. et al., Synthesis of arylsulfonyl hydrazide of 3-R-quinazolone-4-carbonyl-2-acid, Pharmaceutical Journal (1979), pp. 70-71.
Bhaduri, A.P. et al, Urinary Metabolite of 2-Piperazino-3 (H)-4-Quinazolone (Centpiperalone), A Potent Blood Sugar Lowering Agent, Indian J. Biochem. Biophys., vol. 12 (1975), pp. 413-414.
Borrell, J. I. et al.: "Synthesis, structure and cytotoxicity evaluation of palladium(II) complexes of 4-amino-3-hydrazino-1,2,4-triazin-5(4h)-on es and 4-amino-3-(n-methylhydrazino)-1,2,4-triazi N-5(4H)-ones" Anales De Quimica, vol. 91, No. 3/4, 1995, pp. 243-252, XP008000323.
Botta, M., Saladino, R., Lamba, D. Nicoletti, R.: Researches on Antiviral Agents. 31. Synthesis and Transformations of Racemic and Chiral 6-Oxiranyl Pyrimidinones, Tetrahedron, vol. 49, 1993, pp. 6053-6070, XP002329846.
Bouras, Mohammed, et al., Metabolism of enterostatin in rat intestine, brain, membranes and serum: differential involvement of proline-specific peptidases, Peptides, vol. 16, No. 3, (1995), pp. 399-405.
Brun, Jean-Frederic, et al., Effects of Oral Zinc Gluconate on Glucose Effectiveness and Insulin Sensitivity in Humans, Biological Trace Element Research vol. 47 (1995), pp. 385-391.
Buckley, Di, Analysis of the Degradation of Insulinotropin [GLP-1 (7-37)] In Human Plasma and Production of Degradation Resistant Analogs, Regul. Pept. 40, 117, 1992.
Buysens, K. J. et al.: "Synthesis of New Pyrrolo[3,4-b]- and [3,4-c]pyridin(on)es and related 1,7-Naphthyridinones and 2,7-naphthyridines via intramolecular diels-alder reactions of 2(1H)-pyrazinones" Tetrahedron, Elsevier Science Publishers, Amsterdam, NL, vol. 52, No. 27, (Jul. 1, 1996), pp. 9161-9178, XP004104003.
Caira M R: "Crystalline Polymorphism of Organic Compounds" Topics in Current Chemistry, Springer, Berlin, DE, vol. 198, 1998, pp. 163-208, XP001156954 ISSN: 0340-1022, p. 16.
Chatterjee, A.K. et al., Effect of Centpiperalone in Insulin Deficient Diabetes, Indian Journal of Experimental Biology vol. 18 (1980), pp. 1005-1008.
Chatterjee, A.K. et al., Effect of Centpiperalone, a New Hypoglycemic Agent on Insulin Biosynthesis & Release from Isolated Pancreatic Islets of Rat, Indian Journal of Experimental Biology vol. 20 (1981) pp. 270-272.
Chenard et al. J. Med Chem. 2001, 44, 1710-1717.
Coppola, Gary M. et al., 1-Aminomethylisoquinoline-4-carboxylates as Novel Dipeptidylpeptidase IV Inhibitors, Bioorganic & Medicinal Chemistry Letters vol. 10 (2000), pp. 1555-1558.
Database Beilstein [online] Beilstein Corssfire Institut Zur Foerderung Der Chemischen Wissenschaften, DE; 1989 XP002392086. Database Accession No. BRN 5951213 abstract.

Database Beilstein [online] Beilstein Crossfire Institut Zur Foerderung Der Chemischen Wissenschaften, DE; 1924, XP002392085. Database Accession No. BRN 3799088 abstract.
Database Beilstein [online] Beilstein Crossfire Institut Zur Foerderung Der Chemischen Wissenschaften, DE; 1960 XP002392087. Database Accession No. BRN 609897 abstract.
Database Beilstein [online] Beilstein Crossfire Institut Zur Foerderung Der Chemischen Wissenschaften, DE; 1993 XP002392088. Database Accession No. BRN 6139401 abstract.
Database Beilstein [online] Beilstein Crossfire Institut Zur Foerderung Der Chemischen Wissenschaften, DE; Citation No. 5593678 1991, XP00239083.
Database Beilstein [online] Beilstein Crossfire Institut Zur Foererung Der Chemischen Wissenschaften DE; 1974 XP002392089. Database Accession No. BRN 514343 abstract.
Database Beilstein [online] Beilstein Crossfire Institut Zur Forderung Der Chemischen Wissenschaften, DE; 1991, XP002392082. Database Accession No. BRN 5340228 abstract.
Database Biosis [Online] Biosciences Information Service, Philadelphia, PA, US; 1991, Bahaji E-H et al.: "Studies on Immunostimulating Derivatives Synthesis of Some Pyrrolo-1 2-C-Pyrimidines" XP002392081. Database accession No. PREV199192140000 abstract.
Database CA [online] Chemical Abstract service, Columbus, Ohio, US; Reg No. 102482-94-0 Liu, Gang: "Fungal endophyte-epichloe and its secondary metabolites" XP002392084. Database Accession No. 2004:340837 abstract.
Database CA Online Chemical Abstracts Service, Columbus, OH, US; Troschuetz, Reinhard et al., The reaction of O-functional benzylmalononitriles with N-bisnucleophiles as well as alcoholates. XP-002311761 retrieved from STN Database accession No. 1994:217538 abstract & Archiv Der Pharmazie (Winheim, Germany), 326(11), 865-9 Coden: ARPMAS; ISSN: 0365-6233, 1993.
Database Crossfire Beilstein Institut Zur Foerderung Der Chmischen Wissenschaften. XP-002310117. Beilstein Registry No. 8373244 & KHIM. Geterotsikl. Soedin., No. 8, 1998, pp. 1125-1129.
Database Crossfire Beilstein Institut Zur Foerderung Der Chmischen Wissenschaften. XP-002310118. Beilstein Registry No. 7643826 & KHIM. Geterotsikl. Soedin., vol. 32, No. 5, 1996, pp. 703-707.
Database Crossfire Beilstein Institut Zur Foerderung Der Chmischen Wissenschaften. XP-002310119. Beilstein Registry No. 649497 & J. Pharm. Sci. vol. 80, No. 7, 1991, pp. 705-706.
Database Crossfire Beilstein Institut Zur Foerderung Der Chmischen Wissenschaften. XP-002310120. Beilstein Registry No. 638238 & Synthetic Procedures in Nucleic Acid Chemistry, vol. 1, 1968, p. 92.
Database Crossfire Beilstein Institut Zur Foerderung Der Chmischen Wissenschaften. XP-002310121. Beilstein Registry No. 7289032 & Nucleosides Nucleotides, vol. 14, No. 3-5, 1995, pp. 653-656.
Database Crossfire Beilstein Institut zur Foerderung der Wissenchaften, Frankfurt am Main, DE; XP002335064. Database Accession No. 1447881 & J. Heterocycl.Chem., vol. 305,1972, pp. 724-730.
Database Crossfire Beilstein Institut zur Foerderung der Wissenchaften, Frankfurt am Main, DE; XP002335065. Database Accession No. 1447134 & J.Org.Chem., vol. 43, 1978, pp. 4069-4074.
Database Crossfire Beilstein Institut zur Foerderung der Wissenchaften, Frankfurt am Main, DE; XP002335066. Database Accession No. 386682 & J.Chem.Soc., 1952, pp. 4985-4990.
Database Crossfire Beilstein Institut zur Foerderung der Wissenchaften, Frankfurt am Main, DE; XP002335067. Database Accession No. 389575 & Chem.Ber., vol. 88, 1968, pp. 106-109.
Database Crossfire Beilstein Institut zur Foerderung der Wissenchaften, Frankfurt am Main, DE; XP002335068. Database Accession No. 472441 & Yakugaku Zasshi, vol. 88, 1968, pp. 106-109.
Database Crossfire Beilstein Institut zur Foerderung der Wissenchaften, Frankfurt am Main, DE; XP002335069. Database Accession No. 1447840 & Chem.Ber., vol. 101, No. 8, 1968, pp. 2679-2689.
Database Crossfire Beilstein Institut zur Foerderung der Wissenchaften, Frankfurt am Main, DE; XP002335070. Database Accession No. 1448669 & Chem.Ber., vol. 101, No. 8, 1968, pp. 2679-2689.
Database Crossfire Beilstein Institut zur Foerderung der Wissenchaften, Frankfurt am Main, DE; XP002335071. Database Accession No. 4991064, J.Chem.Soc.Perkin Trans.1, 1980, pp. 1370-1380.
Database Crossfire Beilstein Institut zur Foerderung der Wissenchaften, Frankfurt am Main, DE; XP002335072. Database Accession No. 990008, J.Prakt.Chem., vol. 315, 1973, pp. 1166-1168.
Database Crossfire Beilstein Institut zur Foerderung der Wissenchaften, Frankfurt am Main, DEe; XP002335073. Database Accession No. 6219070, J.Prakt.Chem., vol. 330, No. 2, 1988, pp. 323-324.
Database Crossfire Beilstein Institut zur Foerderung der Wissenchaften, Frankfurt am Main, DE; XP002335074. Database Accession No. 392446, J.Heterocycl.Chem., vol. 8, 1971, pp. 367-371.
Database Crossfire Beilstein Institut zur Foerderung der Wissenchaften, Frankfurt am Main, DE; XP002335075. Database Accession No. 4742608, J. Prakt.Chem., vol. 333, No. 1, 1991, pp. 149-151.
Database Crossfire Beilstein Institut zur Foerderung der Wissenchaften, Frankfurt am Main, DE; XP002335076. Database Accession nNo. 490809, & Angew.Chem., vol. 84, 1972, p. 1185.
Database Crossfire Beilstein Institut zur Foerderung der Wissenschaften, Franfurt am Main, DE: XP002335063. Database-Accession No. 1525341 & J. Heterocycl.Chem., vol. 12, 1975, pp. 683-687.
Deacon, Carolyn F. et al., Both Subcutaneously and Intravenously Administered Glucagon-Like Peptide I Are Rapidly Degraded From the $NH_2$-Terminus in Type II Diabetic Patients and in Healthy Subjects, Diabetes, vol. 44 (1996), pp. 1125-1131.
Deacon, Carolyn F. et al., Degradation of Glucagon-Like Peptide 1 in Vitro Yields an N-Terminally Truncated Peptide That is a Major Endogenous Metabolite in Vivo, Journal of Clinical Endocrinology and Metabolism vol. 80, No. 3 (1995), pp. 952-957.
Deacon, Carolyn F. et al., Dipeptidyl peptidase IV Inhibition as an Approach to the Treatment and Prevention of Type 2 Diabetes: a Historical Perspective, Biochemical and Biophysical Research Communications 294 (2002), pp. 1-4.
Deacon, Carolyn F. et al., Dipeptidyl peptidase IV Inhibition Influences GLP-1 Metabolism in Vivo, Regulatory Peptides vol. 64 Issues 1-3 (1996) p. 30.
Deacon, Carolyn F. et al., Dipeptidyl peptidase IV Inhibition Potentiates the Insulinotropic Effect of Glucagon-Like Peptide 1 in the Anesthetized Pig, Diabetes, vol. 47 (1998), pp. 764-769.
Demuth, Hans-Ulrich et al., Rebuttal to Deacon and Holst: "Metaformin effects on depeptidyl peptidase IV degradation of glucagons-like peptide-1" versus "dipeptidyl peptidase inhibition as an approach to the treatment and prevention of type 2 diabetes: a historical perspective" Biochemical and Biophysical Research Communications 296 (2002) pp. 229-232.
Dey, Paramita D., et al., Regioselective [4+2] Cycloaddition versus Nucleophilic Reactions of N-Arylamino Substituted 1,3-Diaza-1,3-Butadienes with Ketenes: Synthesis of Pyrimidinone and Fused Pyrimidione Derivatives. Part II. Tetrahedron, vol. 53, No. 40, pp. 13829-13840, 1997.
Dumas, Donald J. "Total synthesis of peramine" Journal of Organic Chemistry, American Chemical Society, Easton, US, vol. 5, 1988, pp. 4650-4653, XP002087391.
Engel, Michael et al., The crystal structure of dipeptidyl peptidase IV (CD26) reveals its functional regulation and enzymatic mechanism, Proc. Nat. Acad. Sci. Early Edition (2003), pp. 1-6.
Fantus, I. George, et al., Mechanism of Action of Metformin: Insulin Receptor and Postreceptor Effects in Vitro and in Vivo, J. Clinical Endocrinology & Metabolism (1986), pp. 898-905.
Fraisse, L., et al. Long-Chained Substituted Uric Acid and 5,6-Diaminouracil Derivatives as Novel Agents against Free Radical Processes: Synthesis and in Vitro Activity, Journal of Medicinal Chemistry, vol. 36, 1993, pp. 1456-1473, XP002329847.
Fraser & Kermack "The Reaction of Paludrine (Proguanil) with Ethyl Acetoacetate" 1951 pp. 2682-2686.
Garratt, Peter J. et al., A Novel Synthesis of Dihydropyrimidines, J. Chem. Soc., Chem. Commun. (1987), pp. 568-569.
Garratt, Peter J. et al., One-Carbon Compounds as Synthetic Intermediates. The Synthesis of Hydropyrimidines and Hydroquinazolines by Sequential Nucleophilic Addition to Diphenyl Cyanocarbonimidate With Concomitant Cyclization, J. Org. Chem. (1988), pp. 1062-1069.

Gazit, Aviv et al., Tyrphostins IV—Highly Potent Inhibitors of EGF Receptor Kinase. Structure-Activity Relationship Study of 4-Anilidoquinazolines, Bioorganic & Medicinal Chemistry, vol. 4, No. 8 (1996) pp. 1203-1207.

Guerrieri, N., et al., Vanadium Inhibition of Serine and Cysteine Proteases, Comparative Biochemistry and Physiology Part A 122 (1997), pp. 331-336.

Gupta, a. et al.: "Fluorine containing Biologically Active Agents: Synthesis of some new Pyrimidine Derivatives" J.Ind. Chem.Soc., vol. 71 1994, pp. 635-636, XP000889664 compound 1.

Gupta, C.M. et al., A Novel Class of Hypoglycaemic Agents: Syntheses & SAR in 2-Substituted 4(3H)-Quinazolones, 2-Substituted 4-Hydroxypolymethylene 5,6]pyrimidines & 3-Substituted 4-Oxopyrido [I,2-a] pyrimidines, Indian Journal of Chemistry, vol. 9 (1971), pp. 201-206.

Gupta, C.M. et al., Drugs Acting on the Central Nervous System. Syntheses of Substituted Quinazolones and Quinazolines and Triazepino-and Triazocionquinazolones, Division of Medicinal Chemistry, Central Drug Research Institute, Lucknow, India (1968), pp. 392-395.

Gupta, C.M. et al., New Potent Blood Sugar Lowering Compound, Nature, vol. 223 (1969), p. 524.

Hcaplus 121: 35089, 1994.

Hcaplus 122: 132810, 1994.

Hermecz, Istvan et al., Pyrido[1,2-a]Pyrimidines; New Chemical Entities in Medicinal Chemistry, Medicinal Research Reviews, vol. 8, No. 2 (1988) pp. 203-230.

Hinke, Simon A. et al., Metformin Effects on Dipeptidylpeptidase IV Degradation of Glucagon-like Peptide-1, Biochemical and Biophysical Research Communications, 291 (2002) pp. 1302-1308.

Hinke, Simon A. et al., On Combination Therapy of Diabetes With Metformin and Dipeptidyl Peptidase IV Inhibitors, Diabetes Care, vol. 25, No. 8 (2002) pp. 1490-1492.

Holz, George G. et al, Pancreatic Beta-Cells are Rendered Glucose-Competent by the Insulinotropic Hormone Glucagon-Like Peptide-1(7-37), Nature, vol. 361 (1993), pp. 362-365.

Jakubkiene, Virginija, et al., (G-Methyl-2methylsulfany1-4-oxo-3,4-dihydro-3- pyrimidinyl)acetic acid and related compounds exhibiting anti-inflammatory activity. Pharmazie 57 (2002) 9, pp. 610-613.

Jones, Terence R., et al., Azafluorenes Containing Two Bridgehead Nitrogen Atoms. Journal of the Chemical Society, Perkin Transactions 1, No. 12, Dec. 1987, pp. 2585-2592.

Kesarwani, A. P. et al.: Solid-phase synthesis of quinazolin-(3H)-ones with three-point diversity, Tetrahedron Letters, vol. 43, (2002) pp. 5579-5581.

Khalid, Noraini M., et al., Purification and Partial Characterization of a ProlylDipeptidyl Aminopeptidase From Lactobacillus helveticus CNRZ 32, Applied and Environmental Microbiology (1990), pp. 381-388.

Kieffer, Timothy J. et al., Degradation of Glucose-Dependant Insulinotropic Polypeptide and Truncated Glucagon-Like Peptide 1 in Vitro and in Vivo by Dipeptidyl Peptidase IV, Endocrinology, vol. 136, No. 8 (1995) 3585-3596.

Kim, H.O. et al., Structure-Activity Relationships of 1,3-Dialkylxanthine Derivatives at Rat $A_3$ Adenosine Receptors, Journal of Medicinal Chemistry, vol. 37, 1994, pp. 3373-3382, XP002329848.

Kimura, Toshikiro et al., Oral Administration of Insulin as Poly(Vinyl Alcohol)-Gel Spheres in Diabetic Rats, Biological & Pharmaceutical Bulletin, vol. 19, No. 6 (1996), 897-900.

Kobe, J. et al.: "The synthesis of s-triazolo[4.3-a]1,3,5-triazines" Tetrahedron, Elsevier Science Publishers, Amsterdam, NL, vol. 26, Jul. 1970, pp. 3357-3368, XP002390908.

Koreeda, Yuji et al., Isolation and Characterization of Dipeptidyl Peptidase IV From *Prevotella loescheii* ATCC 15930, Archives of Oral Biology, 46 (2001), 759-766.

Kotra, L. P. et al.: "4-Azido-2-pyrimidone Nucleosides and Related Chemistry" Journal of Organic Chemistry, American Chemical Society. Easton, US, vol. 62, 1997, pp. 7267-7271, XP002390905.

Kozhevnikov et al. Tr. Perm. Sel.-Khoz. Inst. (1971), No. 79, 66-72 From ref. Zh., Khim. 1972, Abstr. No. 9Zh404 Journal (English Abstract attached).

Kusar, Mihael et al., Diethyl $N,N$-Dimethylaminomethylenemalonate in the Synthesis of Fused Heterocyclic Systems, Heterocyclic Chem. 33 (1996) pp. 1041-1046.

Li Jinping, et al., Permolybdate and Pertungstate—Potent Stimulators of Insulin Effects in Rat Adipocytes: Mechanism of Action, Biochemistry, 34 (1995) 6218-6225.

Lin, Jian, Total Synthesis and Biological Evaluation of Fluoroolefin-containing Dipeptidyl Isosteres as Inhibitors of Dipeptidyl Peptidase IV (CD26), Dissertation presented to State University of New York at Albany, Department of Chemistry (1998).

Loeser, Eric et al., Selective $N$-Alkylation of Primary Amines with Chloroacetamides Under pH-Controlled Aqueous Conditions, Synthetic Communications, 32(3) (2002) pp. 403-409.

Majim R. Berichet der Deutschen Chemischen Gesellschaft 1908 41 pp. 176-186.

Malloy, J. Ardill et al., Effect of Metaformin Treatment on Gastric Acid Secretion Gastrointestinal Hormone Levels in Normal Subjects, Diabetologia, vol. 19 (1980) 93-96.

Mannucci, Eduardo, et al., Effect of Metformin on Glucagon-Like Peptide-1 (GLP-1) and Leptin Levels in Obese Nondiabetic Subjects, Diabetes Care, vol. 24, No. 3 (2001) 489-494.

Mentlein, Rolf et al., Dipeptidyl-Peptidase IV Hydrolyses gastric Inhibitory Polypeptide, Glucagon-Like Peptide-1(7-36)amide, Peptide Histidine Methionine and is Respoinsible for Their Degradation in Human Serum, Eur. J. Biochem, vol. 214, 829-835 (1991).

Meyerovitch, Joseph et al., Oral Administration of Vanadate Normalizes Blood Glucose Levels in Streptozotocin-Treated Rats, the Journal of Biological Chemistry, vol. 262, No. 14 (1987) 6658-6662.

Molina, P. et al.: "Iminophosphorane-mediated annulation of 1,3,5-triazine to benzimidazole: Synthesis of 1,3,5-triazino[1,2-a]benzimidazoles" Synthesis 1992 Germany, No. 3, 1992- pp. 297-302, XP002390907.

Mukerjee, S.S. et al., Chronic Toxicity Studies of a Hypoglycemic Compound: Centpiperalone in Rats & Rhesus Monkeys, Indian Journal of Experimental Biology, vol. 17 (1979) pp. 1346-1349.

Mukerjee, S.S. et al., Effect of 2-piperazino-4(3H)-quinazolinone monoacetate on the tissue respiration, glucose uptake and lactic acid production by rat hemidiaphragm, Biochemical Pharmacology, vol. 23 (1974) 3066-3067.

Mukerjee, S.S. et al., Studies on the Mechanism of Centpiperalone-lnduced Hypoglycemia, Acta Diabet. Lat 13, 8 (1976) p. 8.

Mukerjee, S.S. et al., Tissue Distribution of [$^3$H]Centpiperalone after Oral Administration, Indian J. Biochem. Biophys., vol. 17 (1980) pp. 399-401.

Mukherjee, Subal S. et al., Studies on the Mechanism of Centpiperalone-lnduced Hypoglycemia, Acta Diabet. Lat. 13, 8, (1976) pp. 8-19.

Mukherjee, Surath K. et al., A novel hypoglycemic compound, Biochemical Pharmacology, vol. 22 (1972) pp. 1529-1531.

Mukherjee, Surath K. et al., Effect of 2-piperazino-4(3H)-quinazolinone monoacetate on some aspects of carbohydrate metabolism of albino rats, Biochemical Pharmacology, vol. 22 (1973) pp. 2205-2206.

Mukherjee, Surath K. et al., Influence of Timing Oral Dosing of a Novel Hypoglycaemic Agent A-4166 in Relation to Food, Diabetologia vol. 38 A194 Supplement 1 (1995).

Mukherjee, Surath K. et al., Studies on the Metabolic Changes Induced by a Synthetic Insulinogenic Agent, Ind. J. Physiol. & Allied Sci., vol. 30, No. 3 (1976) pp. 105-116.

Murthy, G. Rama et al., New Hypoglycemic Agents: Part V—Synthesis & Hypoglycemic Activity of Some New 1-[[p-(4-OXO-2-Methyl/Phenyl-3 (4H)-Quinazolinyl) Phenyl]] 3-Aryl-2-Ureas, Indian Drugs, 25 (1) (1987) pp. 19-22.

Murthy, G. Rama et al., New Hypoglycemic Agents: Synthesis and Hypogylcemic Activity of Some New 1-[{p-(4-OXO-2-Substituted-3(4H)-Quinazolinyl)-Phenyl} Sulphonyl]-3-Aryl/Cyclohexyl-2-Thioureas, Current Science, vol. 56, No. 24 (1987) pp. 1263-1265.

Nakamura, Seiji, et al., Effect of Chronic Vanadate Administration in Partially Depancreatized Rats, Diabetes Research and Clinical Practice 27 (1995) pp. 51-59. (Abstract Only).

Ohkubo, I., et al., Dipeptidyl Peptidase IV From Porcine Seminal Plasma: Purification, Characterization, and N-Terminal Amino Acid Sequence, J. Biochem. (Tokyo) (1994) 116(5) pp. 1182-11826.

Pandeya, S.N. et al., Synthesis of Some New Amidine Derivatives As Potent Hypoglycemic Agents, Pharmacological Research Communications, vol. 17, No. 8 (1985) pp. 699-709.

Patent Abstracts of Japan, vol. 2003, No. 12, Xanthine Derivative, Dec. 5, 2003 & JP 2003 300977 A (Sumitomo Pharmaceut Co Ltd), Oct. 21, 2003, Abstract.

Patent Asbstracts of Japan Publication No. 2002338551, Publication Date Nov. 27, 2002.

Pauly, R.P. et al., Inhibition of Dipeptydyl Peptidase IV (DPIV) in Rat Results in Improved Glucose Tolerance, Regulatory Peptides vol. 64, Issues 1-3 (1996) p. 148.

Pederson, Raymond A. et al., Improved Glucose Tolerance in Zucker Fatty Rats by Oral Administration of the Dipeptidyl Peptidase IV Inhibitor Isoleucine Thiazolide, Diabetes, vol. 47 (1998) pp. 1253-1258.

Pillai, Sreekumar et al., Effects of ATP, Vanadate, and Molybdate on Cathepsin D-catalyzed Proteolysis, The Journal of Biological Chemistry, vol. 280, No. 14 (1985) pp. 8384-8389.

Podanyi, Benjamin et al., Nitrogen Bridgehead Compounds. 62. Conformational Analysis of 6, 7, 8, 9-Tetrahydro-4H-pyrido[1,2-a]pyrimidin-4-ones and Their Methyl Derivatives by NMR Spectroscopy, J. Org. Chem. 51 (1985) 394-399.

Poje, M. et al., Diabetogenic action of allozan-like derivatives of uric acid, Experentia 36 (1980) pp. 78-79.

Poje, M. et al., Oxidation of Uric Acid. 4. Synthesis, Structure, and Diabetogenic Action of 5-Imino-2,4,6 (1H,3H,5H)-pyrimidinetrione Salts and Their Alloxan-like Covalent Adducts, J. Med. Chem. 26 (1983) 861-4.

Polacek, I. et al., Hypoglycemic Activity of Amine Derivatives, Arzneim.-Forsch./ Drug Res. 28 (1978), 791-93.

Pridal, L. et al., Glucagon-Like Peptide-1(7-37) Has a Larger Volume of Distribution Than Glucagon-Like Peptide1(7-36)amide in Dogs and is Degraded More Quickly in Vitro by Dog Plasma, European Journal of Drug Metabolism and Pharmacokinetics, vol. 21 (1995), pp. 51-59.

Ram, Vishnu Ji et al., Synthesis and Antihyperglycemic Activity of Suitably Functionalized 3H-quinazolin-4-ones, Bioorganic & Medicinal Chemistry 11 (2003), pp. 2439-2444.

Rauchman, B.S. et al. "2,4—Diamino-5-benylpyrimidines and Analogues as antibacterial Agents", Journal of Med. Chem., vol. 23, 1980, pp. 384-391, XP002335048 Scheme II.

Sammour et al. Egyptian Journal of Chemistry (1979) vol. Date 1976, 19(6), 1109- 16. (Abstract 2 pages).

Sawyer, James H. et al., Pyrido[1,2-a]pyrimidinium Salts. Part 1. Synthesis from 2-Aminopyridines and Interconversion with 2-(2-Acylvinylamino) pyridines, J.C.S. Perkin I (1972), 1138-1143.

Saxena, A.M. et al., Mode of action of three structurally different hypoglycemic agents: A comparative study, Indian Journal of Experimental Biology, vol. 34 (1996), pp. 351-355.

Sedo, Aleksi et al., Dipeptidyl peptidase IV-like molecules: homologous proteins or homologous activities? Biochimica et Biophysica Acta 1550 (2001), pp. 107-116.

Sekiya, T. et al., Pyrimidine derivatives. III (1) Synthesis of hypoglycemic 4-alkoxy-2-piperazino-activity of 6-polymethylenepyrmidines, Eur. J. Med. Chem. (1982), 75-79.

Senten, Kristel et al., Development of Potent and Selective Dipeptidyl Peptidase II Inhibitors, Bioorganic & Medicinal Chemistry Letters 12 (2002) pp. 2825-2828.

Seth, M. et al., Syntheses of 2-Substituted & 2,3-Distributed 4(3H)-Quinazolones, Indian Journal of Chemistry, vol. 14B (1975), 536-540.

Sharma, Arun K., et al. Tandem sigmatropic shifts in [4+] cycloaddition reactions of 1,3-diazabuta-1,3-dienes with butadienylketene: synthesis of pyrimidinone derivatives. J. Chem. Soc., Perkin Trans. 1, 2002, 774-784.

Shimazawa, Rumiko et al., Novel Small Molecule Nonpeptide Aminopeptidase N Inhibitors with a Cyclic Imide Skeleton, J. Enzyme Inhibition, vol. 14 (1999) pp. 259-275.

Shisheva, Assia, et al., Insulinlike Effects of Zinc Ion in Vitro and in Vivo; Preferential Effects on Desensitized Adipocytes and Induction of Normoglycemia in Streptozocin-Induced Rats, Diabetes, vol. 41 (1992), pp. 982-988.

Sinyak, R. S. et al., Synthesis and Biological Properties of Derivatives of 4-Heterylmercaptoquinazoline, Translated from Khimiko-farmatsevticheskii Zhurnal, vol. 20, No. 2, pp. 168-171 (1986), pp. 103-105.

Sokal, Joseph E., Basal Plasma Glucagon Levels of Man, Journal of Clinical Investigation, vol. 46, no. 5 (1967) pp. 778-785.

Soliman et al. Journal of the Chemical Society of Pakistan (1986), 8(2), 97-106. (Abstract 2 pages).

Somasekhara et al. Indian Journal of Pharmacey (1972), 34(5), 121-2.

Somasekhara et al. Indian Journal of Pharmacy (1972), 34(5), 121-2.

Srivastava, P.P. et al., Efficacy of Centpiperalone in Combination With Biguanide & Sulfonylurea, Indian Journal of Experimental Biology, vol. 21 (1983), pp. 390-392.

STN Printout, Barnickel et al. Abstract of WO 01/23364 A1, 2001.

Sun et al. CAPLUS Abstract 128:257413 (1998).

Tam, S. Y-K, et al.: "Nucleosides 112. Synthesis of Some New Pyrazolo-1 5-A-1 3 5-Triazines and Their C Nucleosides" Journal of Organic Chemistry, vol. 44, No. 25, 1979, pp. 4547-4553, XP002390906.

Tanaka, Keiji et al, Vanadate Inhibits the ATP-Dependant Degradation of Proteins in Reticulocytes Without Affecting Ubiquitin Conjugation, The Journal of Biological Chemistry, vol. 259, No. 4 (1983), 2803-2809.

Villhauer, Edwin B. et al., 1-[[(3-Hydroxy-1-adamantyl)amino]acetyl]-2-cyano-(S)- pyrrolidine: A Potent, Selective, and Orally Bioavailable Dipeptidyl Peptidase IV Inhibitor with Antihyperglycemic Properties, J. Med. Chem. 46 (2003), pp. 2774-2789.

Villhauer, Edwin B. et al., DPP-IV Inhibition and Therapeutic Potential, Annual Reports in Chemistry 36 (2001), 191-200.

Wang, F. et al.: "A novel Synthesis of Aryl[1,2-a]pyrazine Derivatives" Molecules, Molecular Diversity Preservation International, Basel, CH, vol. 9, May 2004, pp. 574-582, XP002390904.

Weber, A.E.: Dipeptidyl Peptidase IV Inhibitors for the Treatment of Diabetes, Journal of Medicinal Chemistry, vol. 47, 2004 pp. 4135-4141, XP002329845.

Wells, Carol L. et al., Role of Anaerobic Flora in the Translocation of Aerobic and Facultatively Anaerobic Intestinal Bacteria, Infection and Immunity, vol. 55, No. 11 (1987) pp. 2689-2694.

Wiedeman, Paul E. et al., Dipeptidyl peptidase IV inhibitors for the treatment of impaired glucose tolerance and type 2 diabetes, Current Opinion in Investigational Drugs, vol. 4, No. 4 (2003), pp. 412-420.

Wolf et al., CAPLUS Abstract 115: 114452 (1991).

Yasuda, Nobuyuki et al. Enhanced Secretion of Glucagon-Like Peptide 1 by Biguanide Compounds, Biochemical and Biophysical Research Communications 298 (2002), pp. 779-784.

Yuen, V.G. et al., Acute and Chronic Oral Administration of Bis(maltolato)oxovanadium(IV) in Zucker Diabetic Fatty (ZDF) Rats, Diabetes Research and Clinical Practice 43 (1999), pp. 9-19.

Zander, Mette, et al., Additive Glucose-Lowering Effects of Glucagon-Like Peptide-1 and Metformin in Type 2 Diabetes, Diabetes Care, vol. 24, No. 4 (2001) pp. 720-725.

Zhang, Anqi et al., Vanadate Stimulation of Insulin Release in Normal Mouse Islets, The Journal of Biological Chemistry, vol. 266, No. 32 (1991), pp. 21649-21656.

DIPEPTIDYL PEPTIDASE INHIBITORS

RELATED APPLICATION

This application is a continuation of U.S. application Ser. No. 11/080,992, filed Mar. 15, 2005, which claims the benefit of U.S. Provisional Application No. 60/553,571 filed Mar. 15, 2004 and U.S. Provisional Application No. 60/629,524 filed Nov. 18, 2004, all of which are incorporated herein by reference.

FIELD OF THE INVENTION

The invention relates to compounds that may be used to inhibit dipeptidyl peptidases as well as compositions of matter and kits comprising these compounds. The present invention also relates to methods for inhibiting dipeptidyl peptidases as well as treatment methods using compounds according to the present invention.

DESCRIPTION OF RELATED ART

Dipeptidyl Peptidase IV (IUBMB Enzyme Nomenclature EC.3.4.14.5) is a type II membrane protein that has been referred to in the literature by a wide a variety of names including DPP4, DP4, DAP-IV, FAPβ, adenosine deaminase complexing protein 2, adenosine deaminase binding protein (ADAbp), dipeptidyl aminopeptidase IV; Xaa-Pro-dipeptidyl-aminopeptidase; Gly-Pro naphthylamidase; postproline dipeptidyl aminopeptidase IV; lymphocyte antigen CD26; glycoprotein GP110; dipeptidyl peptidase IV; glycylproline aminopeptidase; glycylproline aminopeptidase; X-prolyl dipeptidyl aminopeptidase; pep X; leukocyte antigen CD26; glycylprolyl dipeptidylaminopeptidase; dipeptidyl-peptide hydrolase; glycylprolyl aminopeptidase; dipeptidyl-aminopeptidase IV; DPP IV/CD26; amino acyl-prolyl dipeptidyl aminopeptidase; T cell triggering molecule Tp103; X-PDAP. Dipeptidyl Peptidase IV is referred to herein as "DPP-IV."

DPP-IV is a non-classical serine aminodipeptidase that removes Xaa-Pro dipeptides from the amino terminus (N-terminus) of polypeptides and proteins. DPP-IV dependent slow release of dipeptides of the type X-Gly or X-Ser has also been reported for some naturally occurring peptides.

DPP-IV is constitutively expressed on epithelial and endothelial cells of a variety of different tissues (intestine, liver, lung, kidney and placenta), and is also found in body fluids. DPP-IV is also expressed on circulating T-lymphocytes and has been shown to be synonymous with the cell-surface antigen, CD-26. DPP-IV has been implicated in a number of disease states, some of which are discussed below.

DPP-IV is responsible for the metabolic cleavage of certain endogenous peptides (GLP-1 (7-36), glucagon) in vivo and has demonstrated proteolytic activity against a variety of other peptides (GHRH, NPY, GLP-2, VIP) in vitro.

GLP-1 (7-36) is a 29 amino-acid peptide derived by post-translational processing of proglucagon in the small intestine. GLP-1 (7-36) has multiple actions in vivo including the stimulation of insulin secretion, inhibition of glucagon secretion, the promotion of satiety, and the slowing of gastric emptying. Based on its physiological profile, the actions of GLP-1 (7-36) are believed to be beneficial in the prevention and treatment of type II diabetes and potentially obesity. For example, exogenous administration of GLP-1 (7-36) (continuous infusion) in diabetic patients has been found to be efficacious in this patient population. Unfortunately, GLP-1 (7-36) is degraded rapidly in vivo and has been shown to have a short half-life in vivo ($t_{1/2}$=1.5 minutes).

Based on a study of genetically bred DPP-IV knock out mice and on in vivo/in vitro studies with selective DPP-IV inhibitors, DPP-IV has been shown to be the primary degrading enzyme of GLP-1 (7-36) in vivo. GLP-1 (7-36) is degraded by DPP-IV efficiently to GLP-1 (9-36), which has been speculated to act as a physiological antagonist to GLP-1 (7-36). Inhibiting DPP-IV in vivo is therefore believed to be useful for potentiating endogenous levels of GLP-1 (7-36) and attenuating the formation of its antagonist GLP-1 (9-36). Thus, DPP-IV inhibitors are believed to be useful agents for the prevention, delay of progression, and/or treatment of conditions mediated by DPP-IV, in particular diabetes and more particularly, type 2 diabetes mellitus, diabetic dislipidemia, conditions of impaired glucose tolerance (IGT), conditions of impaired fasting plasma glucose (IFG), metabolic acidosis, ketosis, appetite regulation and obesity.

DPP-IV expression is increased in T-cells upon mitogenic or antigenic stimulation (Mattem, T., et al., *Scand. J. Immunol.*, 1991, 33, 737). It has been reported that inhibitors of DPP-IV and antibodies to DPP-IV suppress the proliferation of mitogen-stimulated and antigen-stimulated T-cells in a dose-dependant manner (Schon, E., et al., *Biol. Chem.*, 1991, 372, 305). Various other functions of T-lymphocytes such as cytokine production, IL-2 mediated cell proliferation and B-cell helper activity have been shown to be dependent on DPP-IV activity (Schon, E., et al., *Scand. J. Immunol*, 1989, 29, 127). DPP-IV inhibitors, based on boroProline, (Flentke, G. R., et al., *Proc. Nat. Acad. Sci. USA,* 1991, 88, 1556) although unstable, were effective at inhibiting antigen-induced lymphocyte proliferation and IL-2 production in murine CD4+ T-helper cells. Such boronic acid inhibitors have been shown to have an effect in vivo in mice causing suppression of antibody production induced by immune challenge (Kubota, T. et al., *Clin. Exp. Immun.,* 1992, 89, 192). The role of DPP-IV in regulating T lymphocyte activation may also be attributed, in part, to its cell-surface association with the transmembrane phosphatase, CD45. DPP-IV inhibitors or non-active site ligands may possibly disrupt the CD45-DPP-IV association. CD45 is known to be an integral component of the T-cell signaling apparatus. It has been reported that DPP-IV is essential for the penetration and infectivity of HIV-1 and HIV-2 viruses in CD4+ T-cells (Wakselman, M., Nguyen, C., Mazaleyrat, J.-P., Callebaut, C., Krust, B., Hovanessian, A. G., Inhibition of HIV-1 infection of CD 26+ but not CD 26-cells by a potent cyclopeptidic inhibitor of the DPP-IV activity of CD 26. Abstract P. 44 of the 24.sup.th European Peptide Symposium 1996). Additionally, DPP-IV has been shown to associate with the enzyme adenosine deaminase (ADA) on the surface of T-cells (Kameoka, J., et al., *Science,* 193, 26 466). ADA deficiency causes severe combined immunodeficiency disease (SCID) in humans. This ADA-CD26 interaction may provide clues to the pathophysiology of SCID. It follows that inhibitors of DPP-IV may be useful immunosuppressants (or cytokine release suppressant drugs) for the treatment of among other things: organ transplant rejection; autoimmune diseases such as inflammatory bowel disease, multiple sclerosis and rheumatoid arthritis; and the treatment of AIDS.

It has been shown that lung endothelial cell DPP-IV is an adhesion molecule for lung-metastatic rat breast and prostate carcinoma cells (Johnson, R. C., et al., *J. Cell. Biol.,* 1993, 121, 1423). DPP-IV is known to bind to fibronectin and some metastatic tumor cells are known to carry large amounts of fibronectin on their surface. Potent DPP-IV inhibitors may be useful as drugs to prevent metastases of, for example, breast and prostrate tumors to the lungs.

High levels of DPP-IV expression have also been found in human skin fibroblast cells from patients with psoriasis, rheumatoid arthritis (RA) and lichen planus (Raynaud, F., et al., *J. Cell. Physiol.*, 1992, 151, 378). Therefore, DPP-IV inhibitors may be useful as agents to treat dermatological diseases such as psoriasis and lichen planus.

High DPP-IV activity has been found in tissue homogenates from patients with benign prostate hypertrophy and in prostatosomes. These are prostate derived organelles important for the enhancement of sperm forward motility (Vanhoof, G., et al., *Eur. J. Clin. Chem. Clin. Biochem.*, 1992, 30, 333). DPP-IV inhibitors may also act to suppress sperm motility and therefore act as a male contraceptive agent. Conversely, DPP-IV inhibitors have been implicated as novel for treatment of infertility, and particularly human female infertility due to Polycystic ovary syndrome (PCOS, Stein-Leventhal syndrome) which is a condition characterized by thickening of the ovarian capsule and formation of multiple follicular cysts. It results in infertility and amenorrhea.

DPP-IV is thought to play a role in the cleavage of various cytokines (stimulating hematopoietic cells), growth factors and neuropeptides.

Stimulated hematopoietic cells are useful for the treatment of disorders that are characterized by a reduced number of hematopoietic cells or their precursors in vivo. Such conditions occur frequently in patients who are immunosuppressed, for example, as a consequence of chemotherapy and/or radiation therapy for cancer. It was discovered that inhibitors of dipeptidyl peptidase type IV are useful for stimulating the growth and differentiation of hematopoietic cells in the absence of exogenously added cytokines or other growth factors or stromal cells. This discovery contradicts the dogma in the field of hematopoietic cell stimulation, which provides that the addition of cytokines or cells that produce cytokines (stromal cells) is an essential element for maintaining and stimulating the growth and differentiation of hematopoietic cells in culture. (See, e.g., PCT Intl. Application No. PCT/US93/017173 published as WO 94/03055).

DPP-IV in human plasma has been shown to cleave N-terminal Tyr-Ala from growth hormone-releasing factor and cause inactivation of this hormone. Therefore, inhibitors of DPP-IV may be useful in the treatment of short stature due to growth hormone deficiency (Dwarfism) and for promoting GH-dependent tissue growth or re-growth.

DPP-IV can also cleave neuropeptides and has been shown to modulate the activity of neuroactive peptides substance P, neuropeptide Y and CLIP (Mentlein, R., Dahms, P., Grandt, D., Kruger, R., Proteolytic processing of neuropeptide Y and peptide YY by dipeptidyl peptidase IV, *Regul. Pept.*, 49, 133, 1993; Wetzel, W., Wagner, T., Vogel, D., Demuth, H.-U., Balschun, D., Effects of the CLIP fragment ACTH 20-24 on the duration of REM sleep episodes, *Neuropeptides*, 31, 41, 1997). Thus DPP-IV inhibitors may also be useful agents for the regulation or normalization of neurological disorders.

Several compounds have been shown to inhibit DPP-IV. Nonetheless, a need still exists for new DPP-IV inhibitors that have advantageous potency, stability, selectivity, toxicity and/or pharmacodynamics properties. In this regard, a novel class of DPP-IV inhibitors are provided herein.

SUMMARY OF THE INVENTION

The present invention relates to compounds that have activity for inhibiting DPP-IV. It is noted that these compounds may also have activity for inhibiting other S9 proteases and thus may be used against these other S9 proteases as well as DPP-IV. The present invention also provides compositions, articles of manufacture and kits comprising these compounds.

In one embodiment, a pharmaceutical composition is provided that comprises a DPP-IV inhibitor according to the present invention as an active ingredient. Pharmaceutical compositions according to the invention may optionally comprise 0.001%-100% of one or more DPP-IV inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraocularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with DPP-IV.

In one embodiment, a kit is provided that comprises a composition comprising at least one DPP-IV inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one DPP-IV inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit DPP-IV.

In another embodiment, the compounds, compositions, kits and articles of manufacture are used to treat a disease state for which DPP-IV possesses activity that contributes to the pathology and/or symptomology of the disease state.

In another embodiment, a compound is administered to a subject wherein DPP-IV activity within the subject is altered, preferably reduced.

In another embodiment, a prodrug of a compound is administered to a subject that is converted to the compound in vivo where it inhibits DPP-IV.

In another embodiment, a method of inhibiting DPP-IV is provided that comprises contacting DPP-IV with a compound according to the present invention.

In another embodiment, a method of inhibiting DPP-IV is provided that comprises causing a compound according to the present invention to be present in a subject in order to inhibit DPP-IV in vivo.

In another embodiment, a method of inhibiting DPP-IV is provided that comprises administering a first compound to a subject that is converted in vivo to a second compound wherein the second compound inhibits DPP-IV in vivo. It is noted that the compounds of the present invention may be the first or second compounds.

In another embodiment, a therapeutic method is provided that comprises administering a compound according to the present invention.

In another embodiment, a method of inhibiting cell proliferation is provided that comprises contacting a cell with an effective amount of a compound according to the present invention.

In another embodiment, a method of inhibiting cell proliferation in a patient is provided that comprises administering to the patient a therapeutically effective amount of a compound according to the present invention.

In another embodiment, a method of treating a condition in a patient which is known to be mediated by DPP-IV, or which is known to be treated by DPP-IV inhibitors, comprising administering to the patient a therapeutically effective amount of a compound according to the present invention.

In another embodiment, a method is provided for using a compound according to the present invention in order to manufacture a medicament for use in the treatment of disease state which is known to be mediated by DPP-IV, or which is known to be treated by DPP-IV inhibitors.

In another embodiment, a method is provided for treating a disease state for which DPP-IV possesses activity that contributes to the pathology and/or symptomology of the disease state, the method comprising: causing a compound according to the present invention to be present in a subject in a therapeutically effective amount for the disease state.

In another embodiment, a method is provided for treating a disease state for which DPP-IV possesses activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which DPP-IV possesses activity that contributes to the pathology and/or symptomology of the disease state, the method comprising: administering a compound according to the present invention to a subject such that the compound is present in the subject in a therapeutically effective amount for the disease state.

In another embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of diseases that may be treated by administration of compounds and compositions according to the present invention include, but are not limited to conditions mediated by DPP-IV, in particular diabetes, more particular type 2 diabetes mellitus, diabetic dislipidemia, conditions of impaired glucose tolerance (IGT), conditions of impaired fasting plasma glucose (IFG), metabolic acidosis, ketosis, appetite regulation, obesity, immunosuppressants or cytokine release regulation, autoimmune diseases such as inflammatory bowel disease, multiple sclerosis and rheumatoid arthritis, AIDS, cancers (prevention of metastases, for example, breast and prostrate tumors to the lungs), dermatological diseases such as psoriasis and lichen planus, treatment of female infertility, osteoporosis, male contraception and neurological disorders.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting DPP-IV and thus may themselves be prodrugs for another compound. Such prodrugs of another compound may or may not themselves independently have DPP-IV inhibitory activity.

DEFINITIONS

Figure 1:
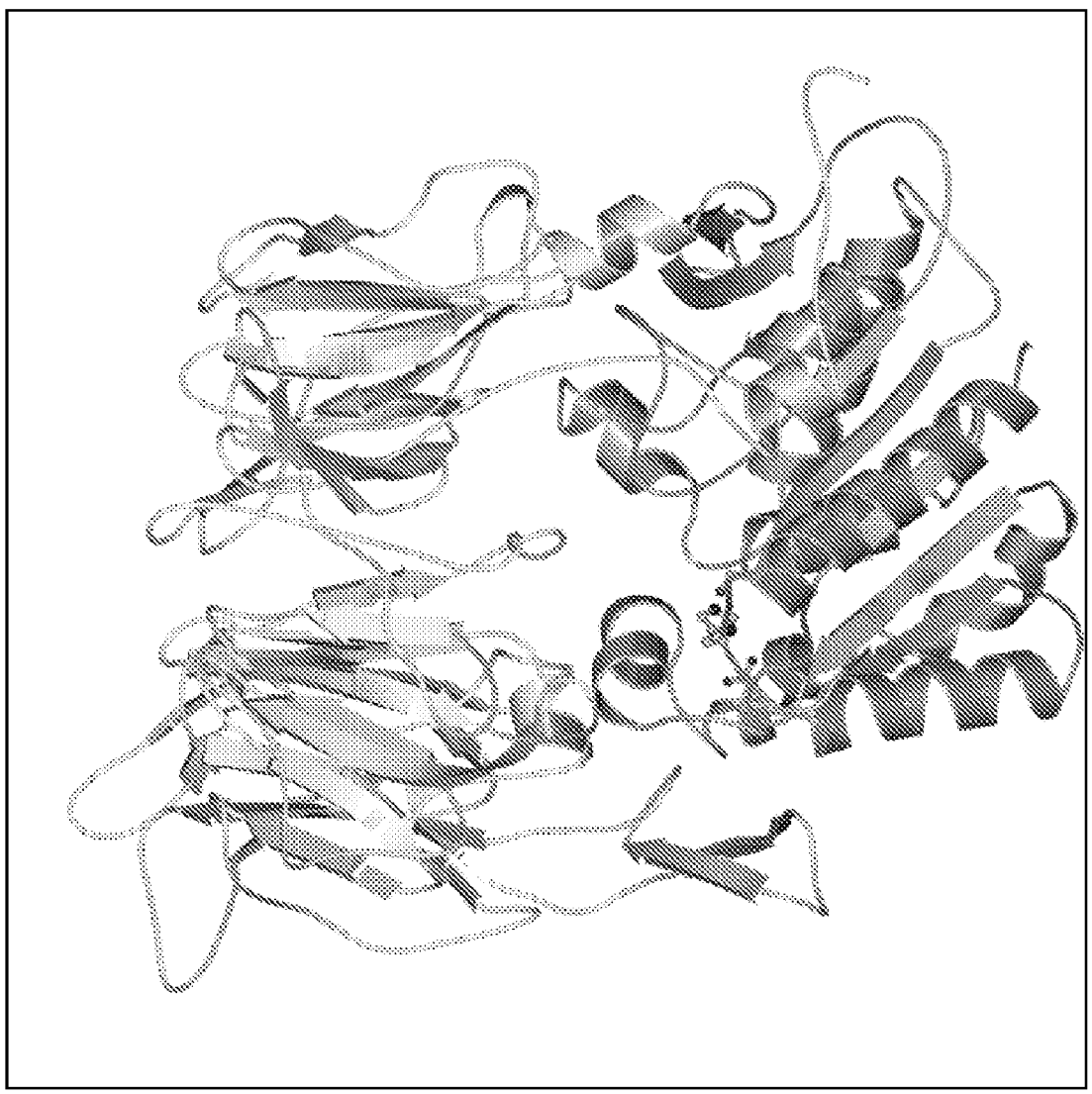
FIG. 1 illustrates a ribbon diagram overview of the structure of DPP-IV, highlighting the secondary structural elements of the protein.

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with C3-C8 rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" represented by itself means a straight or branched, unsaturated, aliphatic radical having a chain of carbon atoms having at least one double bond between adjacent carbon atoms. $C_X$ alkenyl and $C_{X-Y}$ alkenyl are typically used where X and Y indicate the number of carbon atoms in the chain. For example, $C_{2-6}$ alkenyl includes alkenyls that have a chain of between 2 and 6 carbons.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with oxygen (See "oxaalkyl") or nitrogen atoms (See "aminoalkyl") between the carbon atoms. $C_X$ alkyl and $C_{X-Y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like).

"Alkylene", unless indicated otherwise, means a straight or branched, saturated or unsaturated, aliphatic, divalent radical. $C_X$ alkylene and $C_{X-Y}$ alkylene are typically used where X and Y indicate the number of carbon atoms in the chain. For example, $C_{1-6}$ alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like).

"Alkylidene" means a straight or branched saturated or unsaturated, aliphatic radical connected to the parent molecule by a double bond. $C_X$ alkylidene and $C_{X-Y}$ alkylidene are typically used where X and Y indicate the number of carbon atoms in the chain. For example, $C_{1-6}$ alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like).

"Alkynyl" represented by itself means a straight or branched, unsaturated, aliphatic radical having a chain of carbon atoms having at least one triple bond between adjacent carbon atoms. $C_X$ alkynyl and $C_{X-Y}$ alkynyl are typically used where X and Y indicate the number of carbon atoms in the chain. For example, $C_{2-6}$ alkynyl includes alkynyls that have a chain of between 2 and 6 carbons.

"Amino" means a nitrogen moiety having two further substituents where a hydrogen or carbon atom is attached to the nitrogen. For example, representative amino groups include —NH$_2$, —NHCH$_3$, —N(CH$_3$)$_2$, —NHC$_{1-3}$-alkyl, —N(C$_{1-3}$-alkyl)$_2$ and the like. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aminoalkyl" means an alkyl, as defined above, except where one or more substituted or unsubstituted nitrogen atoms (—N—) are positioned between carbon atoms of the alkyl. For example, an $(C_{2-6})$ aminoalkyl refers to a chain comprising between 2 and 6 carbons and one or more nitrogen atoms positioned between the carbon atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $C_X$ aryl and $C_{X-Y}$ aryl are typically used where X and Y indicate the number of atoms in the ring.

"Bicycloalkyl" means a saturated or partially unsaturated fused bicyclic or bridged polycyclic ring assembly.

"Bicycloaryl" means a bicyclic ring assembly wherein the rings are linked by a single bond or fused and at least one of the rings comprising the assembly is aromatic. $C_X$ bicycloaryl and $C_{X-Y}$ bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NR$_a$R$_b$ where R$_a$ and R$_b$ are each independently two further substituents where a hydrogen or carbon atom is attached to the nitrogen.

"Carbocycle" means a ring consisting of carbon atoms.

"Carbocyclic ketone derivative" means a carbocyclic derivative wherein the ring contains a —CO— moiety.

"Carbonyl" means the radical —CO—. It is noted that the carbonyl radical may be further substituted with a variety of substituents to form different carbonyl groups including acids, acid halides, aldehydes, amides, esters, and ketones.

"Carboxy" means the radical —CO$_2$—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, fused bicyclic or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent saturated or partially unsaturated, monocyclic or polycyclic ring assembly. $C_X$ cycloalkylene and $C_{X-Y}$ cycloalkylene are typically used where X and Y indicate the number of carbon atoms in the ring assembly.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted $(C_{1-3})$alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —N=, —NR$_c$—, —N$^+$(O$^-$)=, —O—, —S— or —S(O)$_2$—, wherein R$_c$ is further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like.

"Heterocycloalkylene" means cycloalkylene, as defined in this application, provided that one or more of the ring member carbon atoms is replaced by a heteroatom.

"Heteroaryl" means a cyclic aromatic group having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this application, provided that one or more of the atoms within the ring is a heteroatom. For example, hetero($C_{4-10}$)bicycloaryl as used in this application includes, but is not limited to, 2-amino-4-oxo-3,4-dihydropteridin-6-yl, tetrahydroisoquinolinyl, and the like.

"Heterocycloalkyl" means cycloalkyl, as defined in this application, provided that one or more of the atoms forming the ring is a heteroatom selected, independently from N, O, or S, Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Hydroxy" means the radical —OH.

"Iminoketone derivative" means a derivative comprising the moiety —C(NR)—, wherein R comprises a hydrogen or carbon atom attached to the nitrogen.

"Isomers" mean any compound having an identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Nitro" means the radical —NO$_2$.

"Oxaalkyl" means an alkyl, as defined above, except where one or more oxygen atoms (—O—) are positioned between carbon atoms of the alkyl. For example, an ($C_{2-6}$)oxaalkyl refers to a chain comprising between 2 and 6 carbons and one or more oxygen atoms positioned between the carbon atoms.

"Oxoalkyl" means an alkyl, further substituted with a carbonyl group. The carbonyl group may be an aldehyde, ketone, ester, amide, acid or acid chloride.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of inhibitors of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have DPP-IV inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis*, 3rd edition, John Wiley & Sons, Inc. 1999.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted.

"Sulfinyl" means the radical —SO—. It is noted that the sulfinyl radical may be further substituted with a variety of substituents to form different sulfinyl groups including sulfinic acids, sulfinamides, sulfinyl esters, and sulfoxides.

"Sulfonyl" means the radical —$SO_2$—. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thiocarbonyl" means the radical —CS—. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the disease (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$R_aR_bR_c$ where $R_a$, $R_b$, and $R_c$ may each independently be hydrogen or any other substituent where the atom attached to the carbon is a heteroatom or cyano. Hence, $CF_3$, $CH_2OH$ and $CH_2CN$, for example, are all $C_1$ alkyls.

DETAILED DESCRIPTION OF THE INVENTION

The present invention relates to compounds, compositions, kits and articles of manufacture that may be used to inhibit dipeptidyl peptidases IV (referred to herein as DPP-IV).

DPP-IV (EC.3.4.14.5 also known as DPP4, DP4, DAP-IV, adenosine deaminase complexing protein 2, adenosine deaminase binding protein (ADAbp) or CD26) is a 766 residue, 240 kDa protein that is a highly specific membrane bound non-classical serine aminodipeptidase. DPP-IV has a serine type mechanism of protease activity, cleaving off dipeptides from the amino-terminus of peptides with proline or alanine at the penultimate position. In addition the slow release of dipeptides of the type X-Gly or X-Ser is reported for some naturally occurring peptides. DPP-IV is constitutively expressed on epithelial and endothelial cells of a variety of different tissues (intestine, liver, lung, kidney and placenta), and is also found in body fluids. DPP-IV is also expressed on circulating T-lymphocytes and has been shown to be synonymous with the cell-surface antigen, CD-26. The wild-type form of full length DPP-IV is described in GenBank Accession Number NM_001935 ("Dipeptidyl peptidase IV (CD 26) gene expression in enterocyte-like colon cancer cell lines HT-29 and Caco-2. Cloning of the complete human coding sequence and changes of dipeptidyl peptidase IV mRNA levels during cell differentiation", Darmoul, D., Lacasa, M., Baricault, L., Marguet, D., Sapin, C., Trotot, P., Barbat, A. and Trugnan, G., J. Biol. Chem., 267 (7), 4824-4833, 1992).

DPP-IV is a member of the S9 family of serine proteases, more particularly the S9B family. Other members of the S9 family include, but are not limited to:

Subfamily S9A: Dipeptidyl-peptidase; Oligopeptidase B (EC 3.4.21.83); Oligopeptidase B; Prolyl oligopeptidase (EC 3.4.21.26);

Subfamily S9B: Dipeptidyl aminopeptidase A; Dipeptidyl aminopeptidase B Dipeptidyl-peptidase IV (EC 3.4.14.5); Dipeptidyl-peptidase V Fibroblast activation protein alpha subunit; Seprase Subfamily S9C: Acylaminoacyl-peptidase (EC 3.4.19.1)

It is noted that the compounds of the present invention may also possess inhibitory activity for other S9 family members and thus may be used to address disease states associated with these other family members.

1. Crystal Structure of DPP-IV

Syrrx, Inc. (San Diego, Calif.) recently solved the crystal structure of DPP-IV. Knowledge of the crystal structure was used to guide the design of the DPP-IV inhibitors provided herein.

FIG. 1 illustrates a ribbon diagram overview of the structure of DPP-IV, highlighting secondary structural elements of the protein. DPP-IV is a cylindrical shaped molecule with an approximate height of 70 Å and a diameter of 60 Å. The catalytic triad of DPP-IV (Ser642, Asp720 and His752) is illustrated in the center of the figure by a "ball and stick" representation. This triad of amino acids is located in the peptidase domain or catalytic domain of DPP-IV. The catalytic domain is covalently linked to the β-propeller domain. The catalytic domain of DPP-IV includes residues 1-67 and 511-778. The catalytic domain of DPP-IV adopts a characteristic α/β hydrolase fold. The core of this domain contains an 8-stranded β-sheet with all strands being parallel except one. The α-sheet is significantly twisted and is flanked by three α-helices on one side and five α-helices on the other. The topology of the β-strands is 1, 2, −1×, 2× and (1×) (J. S. Richardson: The anatomy and taxonomy of protein structure; (1981) Adv. Protein Chem. 269, 15076-15084). A number of residues were identified that contribute to the shape and charge characteristics of the active site. Knowledge of these residues has been an important contribution to the design of DPP-IV inhibitors of the present invention.

2. DPP-IV Inhibitors

In one embodiment, DPP-IV inhibitors of the present invention include compounds comprising:

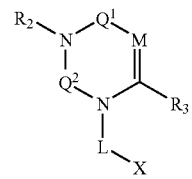

wherein

M is N or $CR_4$;

$Q^1$ and $Q^2$ are each independently selected from the group consisting of CO, CS, SO, $SO_2$, and C=$NR_9$;

$R_2$ is hydrogen or selected from the group consisting of $(C_{1-10})$alkyl, $(C_{3-12})$cycloalkyl, $(C_{3-12})$cycloalkyl$(C_{1-5})$alkyl, hetero$(C_{3-12})$cycloalkyl$(C_{1-5})$alkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, hetero$(C_{4-12})$bicycloaryl$(C_{1-5})$alkyl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, carbonyl group, imino group, sulfonyl group and sulfinyl group, each substituted or unsubstituted;

$R_3$ is selected from the group consisting of perhalo$(C_{1-10})$ alkyl, amino, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$ alkyl, imino $(C_{1-3})$alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;

$R_4$ is hydrogen or is selected from the group consisting of halo, perhalo$(C_{1-10})$alkyl, amino, cyano, thio, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, hydroxy, alkoxy, aryloxy, heteroaryloxy, carbonyl group, imino group, sulfonyl group and sulfinyl group, each substituted or unsubstituted;

$R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted;

L is a linker providing 1, 2 or 3 atom separation between X and the ring to which L is attached, wherein the atoms of the linker providing the separation are selected from the group consisting of carbon, oxygen, nitrogen, and sulfur; and X is selected from the group consisting of $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

In another embodiment, DPP-IV inhibitors of the present invention include compounds comprising:

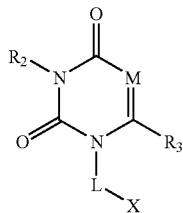

wherein

M is N or CR$_4$;

R$_2$ is hydrogen or selected from the group consisting of (C$_{1-10}$)alkyl, (C$_{3-12}$)cycloalkyl, (C$_{3-12}$)cycloalkyl(C$_{1-5}$)alkyl, hetero(C$_{3-12}$)cycloalkyl(C$_{1-5}$)alkyl, hetero(C$_{3-12}$)cycloalkyl, aryl(C$_{1-10}$)alkyl, heteroaryl(C$_{1-5}$)alkyl, (C$_{9-12}$)bicycloaryl, hetero(C$_{4-12}$)bicycloaryl, hetero(C$_{4-12}$)bicycloaryl(C$_{1-5}$)alkyl, carbonyl(C$_{1-13}$)alkyl, thiocarbonyl(C$_{1-13}$)alkyl, sulfonyl (C$_{1-3}$)alkyl, sulfinyl (C$_{1-3}$)alkyl, imino (C$_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted;

R$_3$ is selected from the group consisting of perhalo(C$_{1-10}$)alkyl, amino, (C$_{1-10}$)alkyl, cycloalkyl, heterocycloalkyl, arylalkyl, heteroarylalkyl, aryl, heteroaryl, carbonyl (C$_{1-3}$)alkyl, thiocarbonyl (C$_{1-3}$)alkyl, sulfonyl (C$_{1-3}$)alkyl, sulfinyl (C$_{1-3}$)alkyl, imino (C$_{1-3}$)alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;

R$_4$ is hydrogen or is selected from the group consisting of halo, perhalo(C$_{1-10}$)alkyl, amino, cyano, thio, (C$_{1-10}$)alkyl, cycloalkyl, heterocycloalkyl, arylalkyl, heteroarylalkyl, aryl, heteroaryl, carbonyl (C$_{1-3}$)alkyl, thiocarbonyl (C$_{1-3}$)alkyl, sulfonyl (C$_{1-3}$)alkyl, sulfinyl (C$_{1-3}$)alkyl, imino (C$_{1-3}$)alkyl, hydroxy, alkoxy, aryloxy, heteroaryloxy, carbonyl group, imino group, sulfonyl group and sulfinyl group, each substituted or unsubstituted;

L is a linker providing 1, 2 or 3 atom separation between X and the ring to which L is attached, wherein the atoms of the linker providing the separation are selected from the group consisting of carbon, oxygen, nitrogen, and sulfur; and X is selected from the group consisting of (C$_{1-10}$)alkyl, (C$_{3-12}$)cycloalkyl, hetero(C$_{3-12}$)cycloalkyl, aryl(C$_{1-10}$)alkyl, heteroaryl(C$_{1-5}$)alkyl, (C$_{9-12}$)bicycloaryl, hetero(C$_{4-12}$)bicycloaryl, carbonyl (C$_{1-3}$)alkyl, thiocarbonyl (C$_{1-3}$)alkyl, sulfonyl (C$_{1-3}$)alkyl, sulfinyl (C$_{1-3}$)alkyl, imino (C$_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

Substituent L:

In one variation of the above embodiments, DPP-IV inhibitors of the present invention comprise compounds wherein the 1, 2 or 3 atoms of L providing the separation consist of carbon atoms. In another variation, the 1, 2 or 3 atoms of L providing the separation are selected from the group of linkers consisting of at least one oxygen or at least one nitrogen atom. In yet another variation, L separates X from the ring atom by one atom.

In one particular variation of the above embodiments, L is selected from the group consisting of —CH$_2$—, —CH$_2$CH$_2$—, —CH$_2$CH$_2$CH$_2$—, —C(O)—, —CH$_2$C(O)—, —C(O)CH$_2$—, —CH$_2$—C(O)CH$_2$—, —C(O)CH$_2$CH$_2$—, —CH$_2$CH$_2$C(O)—, —O—, —OCH$_2$—, —CH$_2$O—, —CH$_2$OCH$_2$—, —OCH$_2$CH$_2$—, —CH$_2$CH$_2$O—, —N(CH$_3$)—, —NHCH$_2$—, —CH$_2$NH—, —CH$_2$NHCH$_2$—, —NHCH$_2$CH$_2$—, —CH$_2$CH$_2$NH—, —NH—C(O)—, —NCH$_3$—C(O)—, —C(O)NH—, —C(O)NCH$_3$—, —NHC(O)CH$_2$—, —C(O)NHCH$_2$—, —C(O)CH$_2$NH—, —CH$_2$NHC(O)—, —CH$_2$C(O)NH—, —NHCH$_2$C(O)—, —S—, —SCH$_2$—, —CH$_2$S—, —SCH$_2$CH$_2$—, —CH$_2$SCH$_2$—, —CH$_2$CH$_2$S—, —C(O)S—, —C(O)SCH$_2$—, —CH$_2$C(O)S—, —C(O)CH$_2$S—, and —CH$_2$SC(O)—, each substituted or unsubstituted.

In another particular variation of the above embodiments, L is selected from the group consisting of —CH$_2$—, —C(O)—, —CH$_2$C(O)—, —C(O)CH$_2$—, —CH$_2$—C(O)CH$_2$—, —C(O)CH$_2$CH$_2$—, and —CH$_2$CH$_2$C(O)—, each substituted or unsubstituted.

In one particular variation of the above embodiments, -L-X taken together is selected from the group consisting of —(CH$_2$)-(2-cyano)phenyl; —(CH$_2$)-(3-cyano)phenyl; —(CH$_2$)-(2-hydroxy)phenyl; —(CH$_2$)-(3-hydroxy)phenyl; —(CH$_2$)-(2-alkenyl)phenyl; —(CH$_2$)-(3-alkenyl)phenyl; —(CH$_2$)-(2-alkynyl)phenyl; —(CH$_2$)-(3-alkynyl)phenyl; —(CH$_2$)-(2-methoxy)phenyl; —(CH$_2$)-(3-methoxy)phenyl; —(CH$_2$)-(2-nitro)phenyl; —(CH$_2$)-(3-nitro)phenyl; —(CH$_2$)-(2-carboxy)phenyl; —(CH$_2$)-(3-carboxy)phenyl; —(CH$_2$)-(2-carboxamido)phenyl; —(CH$_2$)-(3-carboxamido)phenyl; —(CH$_2$)-(2-sulfonamido)phenyl; —(CH$_2$)-(3-sulfonamido)phenyl; —(CH$_2$)-(2-tetrazolyl)phenyl; —(CH$_2$)-(3-tetrazolyl)phenyl; —(CH$_2$)-(2-aminomethyl)phenyl; —(CH$_2$)-(3-aminomethyl)phenyl; —(CH$_2$)-(2-hydroxymethyl)phenyl; —(CH$_2$)-(3-hydroxymethyl)phenyl; —(CH$_2$)-(2-phenyl)phenyl; —(CH$_2$)-(3-phenyl)phenyl; —(CH$_2$)-(2-halo)phenyl; —(CH$_2$)-(3-halo)phenyl; —(CH$_2$)-(2-CONH$_2$)phenyl; —(CH$_2$)-(3-CONH$_2$)phenyl; —(CH$_2$)-(2-CONH(C$_{1-7}$)alkyl)phenyl; —(CH$_2$)-(3-CONH(C$_{1-7}$)alkyl)phenyl; —(CH$_2$)-(2-CO$_2$(C$_{1-7}$)alkyl)phenyl; —(CH$_2$)-(3-CO$_2$(C$_{1-7}$)alkyl)phenyl; —(CH$_2$)-(2-NH$_2$)phenyl; —(CH$_2$)-(3-NH$_2$)phenyl; —(CH$_2$)-(2-(C$_{3-7}$)alkyl)phenyl; —(CH$_2$)-(3-(C$_{3-7}$)alkyl)phenyl; —(CH$_2$)-(2-(C$_{3-7}$)cycloalkyl)phenyl; —(CH$_2$)-(3-(C$_{3-7}$)cycloalkyl)phenyl; —(CH$_2$)-(2-aryl)phenyl; —(CH$_2$)-(3-aryl)phenyl; —(CH$_2$)-(2-heteroaryl)phenyl; —(CH$_2$)-(3-heteroaryl)phenyl; —(CH$_2$)-2-bromo-5-fluoro phenyl; —(CH$_2$)-2-chloro-5-fluoro phenyl; —(CH$_2$)-2-cyano-5-fluoro phenyl; —(CH$_2$)-2,5-dichloro phenyl; —(CH$_2$)-2,5-difluoro phenyl; —(CH$_2$)-2,5-dibromo phenyl; —(CH$_2$)-2-bromo-3,5-difluoro phenyl; —(CH$_2$)-2-chloro-3,5-difluoro phenyl; —(CH$_2$)-2,3,5-trifluoro phenyl; —(CH$_2$)-2,3,5,6-tetrafluorophenyl; —(CH$_2$)-2-bromo-3,5,6-trifluoro phenyl; —(CH$_2$)-2-chloro-3,5,6-trifluoro phenyl; —(CH$_2$)-2-cyano-3,5-difluoro phenyl; —(CH$_2$)-2-cyano-3,5,6-trifluoro phenyl; —(CH$_2$)-(2-heterocycloalkyl)phenyl; and —(CH$_2$)-(3-heterocycloalkyl)phenyl, each substituted or unsubstituted.

In another embodiment, DPP-IV inhibitors of the present invention include compounds comprising:

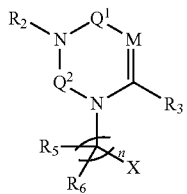

wherein n is 1, 2, or 3;

M is N or $CR_4$;

$Q^1$ and $Q^2$ are each independently selected from the group consisting of CO, CS, SO, $SO_2$, and $C=NR_9$;

$R_2$ is hydrogen or selected from the group consisting of $(C_{1-10})$alkyl, $(C_{3-12})$cycloalkyl, $(C_{3-12})$cycloalkyl$(C_{1-5})$alkyl, hetero$(C_{3-12})$cycloalkyl$(C_{1-5})$alkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, hetero$(C_{4-12})$bicycloaryl$(C_{1-5})$alkyl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, carbonyl group, imino group, sulfonyl group and sulfinyl group, each substituted or unsubstituted;

$R_3$ is selected from the group consisting of perhalo$(C_{1-10})$ alkyl, amino, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$ alkyl, imino $(C_{1-3})$alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;

$R_4$ is hydrogen or is selected from the group consisting of halo, perhalo$(C_{1-10})$alkyl, amino, cyano, thio, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, hydroxy, alkoxy, aryloxy, heteroaryloxy, carbonyl group, imino group, sulfonyl group and sulfinyl group, each substituted or unsubstituted;

each $R_5$ and $R_6$ is independently hydrogen or is selected from the group consisting of a substituted or unsubstituted $(C_{1-10})$alkyl, a substituted or unsubstituted $(C_{1-10})$alkoxy, cyano, and halo, or where $R_5$ and $R_6$ are taken together to form a ring;

$R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted; and X is selected from the group consisting of $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

Substituent X:

In regard to particular variations of the present invention, there is provided compounds wherein X is a substituted or unsubstituted $(C_{3-7})$cycloalkyl. According to each of the above variations, the invention provides compounds wherein X is a substituted or unsubstituted $(C_{3-7})$heterocycloalkyl, or wherein X is a substituted or unsubstituted aryl.

Further, according to each of the above variations, the invention provides compounds wherein X is a substituted or unsubstituted phenyl, or wherein X is a substituted or unsubstituted heteroaryl. In another variation according to the above variation, X is a ring having a non-hydrogen substituent at a 2 or 3 position of the ring.

According to the above variations, there is provided compounds wherein X is a ring having a non-hydrogen substituent at a 2 or 3 position of the ring selected from the group consisting of $(C_{1-10})$alkyl, $(C_{3-12})$cycloalkyl, hetero$(C_{3-12})$ cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl $(C_{1-3})$alkyl, thiocarbonyl $(C_{1-3})$alkyl, sulfonyl $(C_{1-3})$alkyl, sulfinyl $(C_{1-3})$ alkyl, imino $(C_{1-3})$alkyl, amino, aryl, heteroaryl, hydroxy, alkoxy, aryloxy, heteroaryloxy, carbonyl group, cyano, nitro, halo, imino group, sulfonyl group and sulfinyl group, each substituted or unsubstituted. In another variation of the above, X is a substituted or unsubstituted halophenyl or dihalophenyl. In yet another variation, X is a substituted or unsubstituted haloaryl, haloheteroaryl, dihaloaryl or dihaloheteroaryl.

According to the above variations, X is selected from the group consisting of (2-cyano)phenyl; (3-cyano)phenyl; (2-hydroxy)phenyl; (3-hydroxy)phenyl; (2-alkenyl)phenyl; (3-alkenyl)phenyl; (2-alkynyl)phenyl; (3-alkynyl)phenyl; (2-methoxy)phenyl; (3-methoxy)phenyl; (2-nitro)phenyl; (3-nitro)phenyl; (2-carboxy)phenyl; (3-carboxy)phenyl; —$(CH_2)$-(2-carboxamido)phenyl; (3-carboxamido)phenyl; (2-sulfonamido)phenyl; (3-sulfonamido)phenyl; (2-tetrazolyl)phenyl; (3-tetrazolyl)phenyl; (2-aminomethyl)phenyl; (3-aminomethyl)phenyl; (2-hydroxymethyl)phenyl; (3-hydroxymethyl)phenyl; (2-phenyl)phenyl; (3-phenyl)phenyl; (2-halo)phenyl; (3-halo)phenyl; (2-$CONH_2$)phenyl; (3-$CONH_2$)phenyl; (2-CONH$(C_{1-7})$alkyl)phenyl; (3-CONH $(C_{1-7})$alkyl)phenyl; (2-$CO_2(C_{1-7})$alkyl)phenyl; (3-$CO_2(C_{1-7})$ alkyl)phenyl; (2-$NH_2$)phenyl; (3-$NH_2$)phenyl; (2-$(C_{3-7})$ alkyl)phenyl; (3-$(C_{3-7})$alkyl)phenyl; (2-$(C_{3-7})$cycloalkyl) phenyl; (3-$(C_{3-7})$cycloalkyl)phenyl; (2-aryl)phenyl; (3-aryl) phenyl; (2-heteroaryl)phenyl; (3-heteroaryl)phenyl; 2-bromo-5-fluoro phenyl; 2-chloro-5-fluoro phenyl; 2-cyano-5-fluoro phenyl; 2,5-dichloro phenyl; 2,5-difluoro phenyl; 2,5-dibromo phenyl; 2-bromo-3,5-difluoro phenyl; 2-chloro-3,5-difluoro phenyl; 2,3,5-trifluoro phenyl; 2,3,5,6-tetrafluorophenyl; 2-bromo-3,5,6-trifluoro phenyl; 2-chloro-3,5,6-trifluoro phenyl; 2-cyano-3,5-difluoro phenyl; 2-cyano-3,5,6-trifluoro phenyl; (2-heterocycloalkyl)phenyl; and (3-heterocycloalkyl)phenyl, each substituted or unsubstituted.

In regard to the above particular variations, the invention also include compounds wherein X is selected from the group consisting of

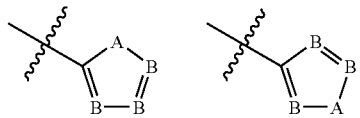

wherein

A is S, O or $NR_{24}$;

B is $CR_{23}$ or N;

$R_{23}$ is independently selected from the group consisting of hydrogen, halo, perhalo$(C_{1-10})$alkyl, amino, thio, cyano, $CF_3$, nitro, $(C_{1-10})$alkyl, $(C_{3-12})$cycloalkyl, hetero$(C_{3-12})$cycloalkyl, aryl$(C_{1-10})$alkyl, heteroaryl $(C_{1-5})$alkyl, $(C_{9-12})$bicycloaryl, hetero($C_{8-12}$)bicycloaryl, carbonyl ($C_{1-3}$)alkyl, thiocarbonyl ($C_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted; and $R_{24}$ is independently selected from the group consisting of hydrogen, perhalo($C_{1-10}$)alkyl, amino, ($C_{1-10}$)alkyl, ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloaryl, hetero($C_{8-12}$)bicycloaryl, carbonyl ($C_{1-3}$)alkyl, thiocarbonyl ($C_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted.

In one variation of the above embodiments and variations, X is selected from the group consisting of

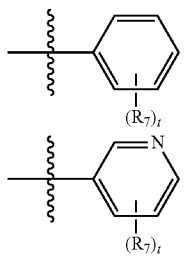 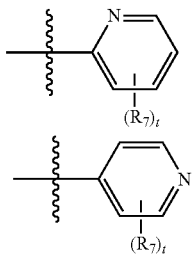

wherein t is 0, 1, 2, 3, 4 or 5; and each $R_7$ is independently selected from the group consisting of halo, perhalo($C_{1-10}$)alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted.

In another variation of the above compounds, X is selected from the group consisting of

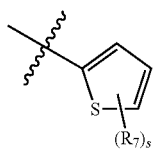 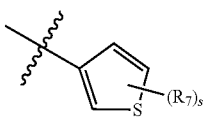

wherein s is 0, 1, 2, or 3; and each $R_7$ is independently selected from the group consisting of halo, perhalo($C_{1-10}$)alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted.

In one particular variation of the above compounds, $R_7$ is independently selected from the group consisting of -cyano, -methoxy, -nitro, -carboxy, -sulfonamido, -tetrazolyl, -aminomethyl, -hydroxymethyl, -phenyl, -halo, —$CONH_2$, —$CONH(C_{1-7})$alkyl, —$CO_2(C_{1-7})$alkyl, —$NH_2$, —OH, —($C_{1-5}$)alkyl, -alkenyl, -alkynyl, ($C_{1-5}$)cycloalkyl, aryl, heteroaryl, and heterocycloalkyl, each substituted or unsubstituted.

In another embodiment, DPP-IV inhibitors of the present invention include compounds comprising:

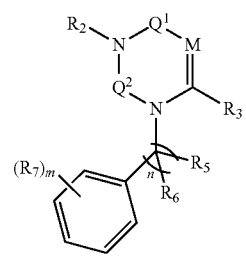

wherein m is 0, 1, 2, 3, 4, or 5;

n is 1, 2, or 3;

M is N or $CR_4$;

$Q^1$ and $Q^2$ are each independently selected from the group consisting of CO, CS, SO, $SO_2$, and C=$NR_9$;

$R_2$ is hydrogen or selected from the group consisting of ($C_{1-10}$)alkyl, ($C_{3-12}$)cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl ($C_{1-13}$)alkyl, thiocarbonyl ($C_{1-13}$)alkyl, sulfonyl ($C_{1-3}$)alkyl, sulfinyl ($C_{1-3}$)alkyl, imino ($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted;

$R_3$ is selected from the group consisting of perhalo($C_{1-10}$)alkyl, amino, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-13}$)alkyl, sulfonyl ($C_{1-13}$)alkyl, sulfinyl ($C_{1-13}$)alkyl, imino ($C_{1-13}$)alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;

$R_4$ is hydrogen or is selected from the group consisting of halo, perhalo($C_{1-10}$)alkyl, amino, cyano, thio, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, hydroxy, alkoxy, aryloxy, heteroaryloxy, carbonyl group, imino group, sulfonyl group and sulfinyl group, each substituted or unsubstituted;

each $R_5$ and $R_6$ is independently hydrogen or is selected from the group consisting of a substituted or unsubstituted ($C_{1-10}$)alkyl, a substituted or unsubstituted ($C_{1-10}$)alkoxy, cyano, and halo, or where $R_5$ and $R_6$ are taken together to form a ring;

each $R_7$ is independently selected from the group consisting of halo, perhalo($C_{1-10}$)alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted; and $R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted.

In another embodiment, DPP-IV inhibitors of the present invention include compounds comprising:
a member selected from the group consisting of

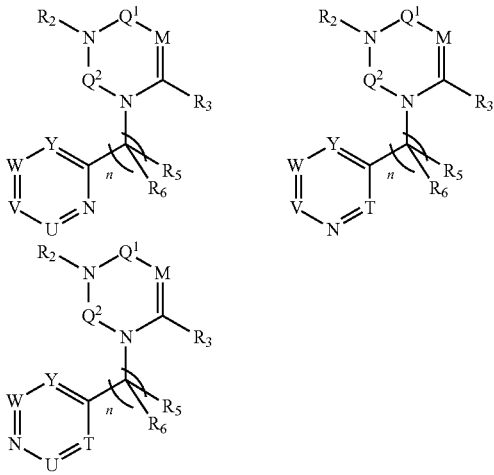

wherein
n is 1, 2, or 3;
M is N or $CR_4$;
each of T, U, V, W and Y is independently nitrogen or $CR_{16}$, provided that no more than two of T, U, V, W and Y are nitrogen;
$Q^1$ and $Q^2$ are each independently selected from the group consisting of CO, CS, SO, $SO_2$, and $C=NR_9$;
$R_2$ is hydrogen or selected from the group consisting of $(C_{1-10})$alkyl, $(C_{3-12})$cycloalkyl, $(C_{3-12})$cycloalkyl$(C_{1-5})$alkyl, hetero$(C_{3-12})$cycloalkyl$(C_{1-5})$alkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, hetero$(C_{4-12})$bicycloaryl$(C_{1-5})$alkyl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, carbonyl group, imino group, sulfonyl group and sulfinyl group, each substituted or unsubstituted;
$R_3$ is selected from the group consisting of perhalo$(C_{1-10})$alkyl, amino, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$ alkyl, imino $(C_{1-3})$alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;
$R_4$ is hydrogen or is selected from the group consisting of halo, perhalo$(C_{1-10})$alkyl, amino, cyano, thio, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, hydroxy, alkoxy, aryloxy, heteroaryloxy, carbonyl group, imino group, sulfonyl group and sulfinyl group, each substituted or unsubstituted;
each $R_5$ and $R_6$ is independently hydrogen or is selected from the group consisting of a substituted or unsubstituted $(C_{1-10})$alkyl, a substituted or unsubstituted $(C_{1-10})$alkoxy, cyano, and halo, or where $R_5$ and $R_6$ are taken together to form a ring;
$R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted; and each $R_{16}$ is independently selected from the group consisting of halo, perhalo$(C_{1-10})$alkyl, $CF_3$, $(C_{1-10})$alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted.

In another embodiment, DPP-IV inhibitors of the present invention include compounds comprising:

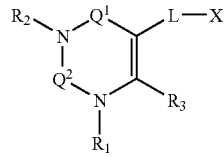

wherein
$Q^1$ and $Q^2$ are each independently selected from the group consisting of CO, CS, SO, $SO_2$, and $C=NR_9$;
$R_1$ is hydrogen or is selected from the group consisting of halo, perhalo$(C_{1-10})$alkyl, amino, cyano, thio, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, hydroxy, alkoxy, aryloxy, heteroaryloxy, carbonyl group, imino group, sulfonyl group and sulfinyl group, each substituted or unsubstituted;
$R_2$ is hydrogen or selected from the group consisting of $(C_{1-10})$alkyl, $(C_{3-12})$cycloalkyl, $(C_{3-12})$cycloalkyl$(C_{1-5})$alkyl, hetero$(C_{3-12})$cycloalkyl$(C_{1-5})$alkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, hetero$(C_{4-12})$bicycloaryl$(C_{1-5})$ alkyl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, carbonyl group, imino group, sulfonyl group and sulfinyl group, each substituted or unsubstituted;
$R_3$ is selected from the group consisting of perhalo$(C_{1-10})$ alkyl, amino, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$ alkyl, imino $(C_{1-3})$alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;
$R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted;
L is a linker providing 1, 2 or 3 atom separation between X and the ring to which L is attached, wherein the atoms of the linker providing the separation are selected from the group consisting of carbon, oxygen, nitrogen, and sulfur; and
X is selected from the group consisting of $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

In another embodiment, DPP-IV inhibitors of the present invention include compounds comprising:

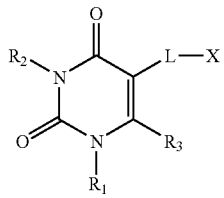

wherein $R_1$ is hydrogen or is selected from the group consisting of halo, perhalo($C_{1-10}$)alkyl, amino, cyano, thio, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, hydroxy, alkoxy, aryloxy, heteroaryloxy, carbonyl group, imino group, sulfonyl group and sulfinyl group, each substituted or unsubstituted;

$R_2$ is hydrogen or selected from the group consisting of ($C_{1-10}$)alkyl, ($C_{3-12}$)cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted;

$R_3$ is selected from the group consisting of perhalo($C_{1-10}$) alkyl, amino, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$) alkyl, imino ($C_{1-3}$)alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;

L is a linker providing 1, 2 or 3 atom separation between X and the ring to which L is attached, wherein the atoms of the linker providing the separation are selected from the group consisting of carbon, oxygen, nitrogen, and sulfur; and X is selected from the group consisting of ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

Substituent L:

In one variation of the present invention, there is provided compounds wherein the 1, 2 or 3 atoms of L providing the separation consist of carbon atoms. In another variation, the 1, 2 or 3 atoms of L providing the separation are selected from the group of linkers consisting of at least one oxygen or at least one nitrogen atom. In one particular variation, L separates X from the ring atom by one atom.

In regard to particular variation of the present invention, L is selected from the group consisting of —$CH_2$—, —$CH_2CH_2$—, —$CH_2CH_2CH_2$—, —C(O)—, —$CH_2$C(O)—, —C(O)$CH_2$—, —$CH_2$—C(O)$CH_2$—, —C(O)$CH_2CH_2$—, —$CH_2CH_2$C(O)—, —O—, —O$CH_2$—, —$CH_2$O—, —$CH_2$O$CH_2$—, —O$CH_2CH_2$—, —$CH_2CH_2$O—, —N($CH_3$)—, —NH$CH_2$—, —$CH_2$NH—, —$CH_2$NH$CH_2$—, —NH$CH_2CH_2$—, —$CH_2CH_2$NH—, —NH—C(O)—, —N$CH_3$—C(O)—, —C(O)NH—, —C(O)N$CH_3$—, —NHC(O)$CH_2$—, —C(O)NH$CH_2$—, —C(O)$CH_2$NH—, —$CH_2$NHC(O)—, —$CH_2$C(O)NH—, —NH$CH_2$C(O)—, —S—, —S$CH_2$—, —$CH_2$S—, —S$CH_2CH_2$—, —$CH_2$S$CH_2$—, —$CH_2CH_2$S—, —C(O)S—, —C(O)S$CH_2$—, —$CH_2$C(O)S—, —C(O)$CH_2$S—, and —$CH_2$SC(O)—, each substituted or unsubstituted.

In regard to another variation of the above compounds, L is selected from the group consisting of —$CH_2$—, —C(O)—, —$CH_2$C(O)—, —C(O)$CH_2$—, —$CH_2$—C(O)$CH_2$—, —C(O)$CH_2CH_2$—, and —$CH_2CH_2$C(O)—, each substituted or unsubstituted.

In another variation of the above compounds, -L-X taken together is selected from the group consisting of —($CH_2$)-(2-cyano)phenyl; —($CH_2$)-(3-cyano)phenyl; —($CH_2$)-(2-hydroxy)phenyl; —($CH_2$)-(3-hydroxy)phenyl; —($CH_2$)-(2-alkenyl)phenyl; —($CH_2$)-(3-alkenyl)phenyl; —($CH_2$)-(2-alkynyl)phenyl; —($CH_2$)-(3-alkynyl)phenyl; —($CH_2$)-(2-methoxy)phenyl; —($CH_2$)-(3-methoxy)phenyl; —($CH_2$)-(2-nitro)phenyl; —($CH_2$)-(3-nitro)phenyl; —($CH_2$)-(2-carboxy)phenyl; —($CH_2$)-(3-carboxy)phenyl; —($CH_2$)-(2-carboxamido)phenyl; —($CH_2$)-(3-carboxamido)phenyl; —($CH_2$)-(2-sulfonamido)phenyl; —($CH_2$)-(3-sulfonamido)phenyl; —($CH_2$)-(2-tetrazolyl)phenyl; —($CH_2$)-(3-tetrazolyl)phenyl; —($CH_2$)-(2-aminomethyl)phenyl; —($CH_2$)-(3-aminomethyl)phenyl; —($CH_2$)-(2-hydroxymethyl)phenyl; —($CH_2$)-(3-hydroxymethyl)phenyl; —($CH_2$)-(2-phenyl)phenyl; —($CH_2$)-(3-phenyl)phenyl; —($CH_2$)-(2-halo)phenyl; —($CH_2$)-(3-halo)phenyl; —($CH_2$)-(2-$CONH_2$)phenyl; —($CH_2$)-(3-$CONH_2$)phenyl; —($CH_2$)-(2-CONH($C_{1-7}$)alkyl)phenyl; —($CH_2$)-(3-CONH($C_{1-7}$)alkyl)phenyl; —($CH_2$)-(2-$CO_2$($C_{1-7}$)alkyl)phenyl; —($CH_2$)-(3-$CO_2$($C_{1-7}$)alkyl)phenyl; —($CH_2$)-(2-$NH_2$)phenyl; —($CH_2$)-(3-$NH_2$)phenyl; —($CH_2$)-(2-($C_{3-7}$)alkyl)phenyl; —($CH_2$)-(3-($C_{3-7}$)alkyl)phenyl; —($CH_2$)-(2-($C_{3-7}$)cycloalkyl)phenyl; —($CH_2$)-(3-($C_{3-7}$)cycloalkyl)phenyl; —($CH_2$)-(2-aryl)phenyl; —($CH_2$)-(3-aryl)phenyl; —($CH_2$)-(2-heteroaryl)phenyl; —($CH_2$)-(3-heteroaryl)phenyl; —($CH_2$)-2-bromo-5-fluoro phenyl; —($CH_2$)-2-chloro-5-fluoro phenyl; —($CH_2$)-2-cyano-5-fluoro phenyl; —($CH_2$)-2,5-dichloro phenyl; —($CH_2$)-2,5-difluoro phenyl; —($CH_2$)-2,5-dibromo phenyl; —($CH_2$)-2-bromo-3,5-difluoro phenyl; —($CH_2$)-2-chloro-3,5-difluoro phenyl; —($CH_2$)-2,3,5-trifluoro phenyl; —($CH_2$)-2,3,5,6-tetrafluorophenyl; —($CH_2$)-2-bromo-3,5,6-trifluoro phenyl; —($CH_2$)-2-chloro-3,5,6-trifluoro phenyl; —($CH_2$)-2-cyano-3,5-difluoro phenyl; —($CH_2$)-2-cyano-3,5,6-trifluoro phenyl; —($CH_2$)-(2-heterocycloalkyl)phenyl; and —($CH_2$)-(3-heterocycloalkyl)phenyl, each substituted or unsubstituted.

In another embodiment, DPP-IV inhibitors of the present invention include compounds comprising:

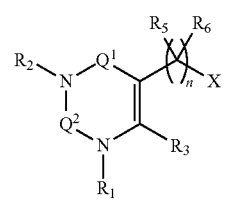

wherein
n is 1, 2, or 3;
$Q^1$ and $Q^2$ are each independently selected from the group consisting of CO, CS, SO, $SO_2$, and $C=NR_9$;
$R_1$ is hydrogen or is selected from the group consisting of halo, perhalo($C_{1-10}$)alkyl, amino, cyano, thio, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, hydroxy, alkoxy, aryloxy, heteroaryloxy, carbonyl group, imino group, sulfonyl group and sulfinyl group, each substituted or unsubstituted;
$R_2$ is hydrogen or selected from the group consisting of ($C_{1-10}$)alkyl, ($C_{3-12}$)cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted;
$R_3$ is selected from the group consisting of perhalo($C_{1-10}$)alkyl, amino, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;
each $R_5$ and $R_6$ is independently hydrogen or is selected from the group consisting of a substituted or unsubstituted ($C_{1-10}$)alkyl, a substituted or unsubstituted ($C_{1-10}$)alkoxy, cyano, and halo, or where $R_5$ and $R_6$ are taken together to form a ring;
$R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted; and
X is selected from the group consisting of ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

Substituent X:
According to the above variations, the invention provides compounds wherein X is a substituted or unsubstituted ($C_{3-7}$)cycloalkyl. In another particular variation of the above compounds, wherein X is a substituted or unsubstituted ($C_{3-7}$)heterocycloalkyl, wherein X is a substituted or unsubstituted aryl, or wherein X is a substituted or unsubstituted phenyl. In another particular variation, X is a substituted or unsubstituted heteroaryl.

In one particular variation of the above compounds, X is a ring having a non-hydrogen substituent at a 2 or 3 position of the ring. In one variation of the above compounds, X is a ring having a non-hydrogen substituent at a 2 or 3 position of the ring selected from the group consisting of ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, amino, aryl, heteroaryl, hydroxy, alkoxy, aryloxy, heteroaryloxy, carbonyl group, cyano, nitro, halo, imino group, sulfonyl group and sulfinyl group, each substituted or unsubstituted.

In another particular variation, X is a substituted or unsubstituted halophenyl or dihalophenyl. In yet another particular variation, there is provided compounds wherein X is a substituted or unsubstituted haloaryl, haloheteroaryl, dihaloaryl or dihaloheteroaryl.

In regard to particular variations, the present invention provides compounds wherein X is selected from the group consisting of (2-cyano)phenyl; (3-cyano)phenyl; (2-hydroxy)phenyl; (3-hydroxy)phenyl; (2-alkenyl)phenyl; (3-alkenyl)phenyl; (2-alkynyl)phenyl; (3-alkynyl)phenyl; (2-methoxy)phenyl; (3-methoxy)phenyl; (2-nitro)phenyl; (3-nitro)phenyl; (2-carboxy)phenyl; (3-carboxy)phenyl; —($CH_2$)-(2-carboxamido)phenyl; (3-carboxamido)phenyl; (2-sulfonamido)phenyl; (3-sulfonamido)phenyl; (2-tetrazolyl)phenyl; (3-tetrazolyl)phenyl; (2-aminomethyl)phenyl; (3-aminomethyl)phenyl; (2-hydroxymethyl)phenyl; (3-hydroxymethyl)phenyl; (2-phenyl)phenyl; (3-phenyl)phenyl; (2-halo)phenyl; (3-halo)phenyl; (2-$CONH_2$)phenyl; (3-$CONH_2$)phenyl; (2-CONH($C_{1-7}$)alkyl)phenyl; (3-CONH($C_{1-7}$)alkyl)phenyl; (2-$CO_2$($C_{1-7}$)alkyl)phenyl; (3-$CO_2$($C_{1-7}$)alkyl)phenyl; (2-$NH_2$)phenyl; (3-$NH_2$)phenyl; (2-($C_{3-7}$)alkyl)phenyl; (3-($C_{3-7}$)alkyl)phenyl; (2-($C_{3-7}$)cycloalkyl)phenyl; (3-($C_{3-7}$)cycloalkyl)phenyl; (2-aryl)phenyl; (3-aryl)phenyl; (2-heteroaryl)phenyl; (3-heteroaryl)phenyl; 2-bromo-5-fluoro phenyl; 2-chloro-5-fluoro phenyl; 2-cyano-5-fluoro phenyl; 2,5-dichloro phenyl; 2,5-difluoro phenyl; 2,5-dibromo phenyl; 2-bromo-3,5-difluoro phenyl; 2-chloro-3,5-difluoro phenyl; 2,3,5-trifluoro phenyl; 2,3,5,6-tetrafluorophenyl; 2-bromo-3,5,6-trifluoro phenyl; 2-chloro-3,5,6-trifluoro phenyl; 2-cyano-3,5-difluoro phenyl; 2-cyano-3,5,6-trifluoro phenyl; (2-heterocycloalkyl)phenyl; and (3-heterocycloalkyl)phenyl, each substituted or unsubstituted.

In one variation of the above compounds, X is selected from the group consisting of

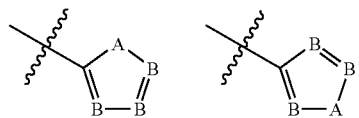

wherein
A is S, O or $NR_{24}$;
B is $CR_{23}$ or N;
$R_{23}$ is independently selected from the group consisting of hydrogen, halo, perhalo($C_{1-10}$)alkyl, amino, thio, cyano, $CF_3$, nitro, ($C_{1-10}$)alkyl, ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloaryl, hetero($C_{8-12}$)bicycloaryl, carbonyl ($C_{1-3}$)alkyl, thiocarbonyl ($C_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted; and
$R_{24}$ is independently selected from the group consisting of hydrogen, perhalo($C_{1-10}$)alkyl, amino, ($C_{1-10}$)alkyl, ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloaryl, hetero($C_{8-12}$)bicycloaryl, carbonyl ($C_{1-3}$)alkyl, thiocarbonyl ($C_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted.

In another particular variation of the above compounds, X is selected from the group consisting of

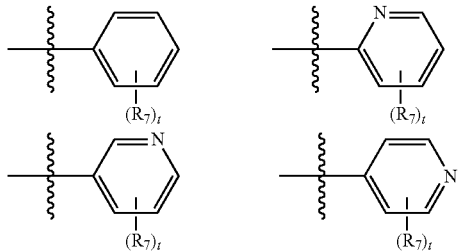

wherein t is 0, 1, 2, 3, 4, or 5; and each $R_7$ is independently selected from the group consisting of halo, perhalo($C_{1-10}$)alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted.

In yet another variation, X is selected from the group consisting of

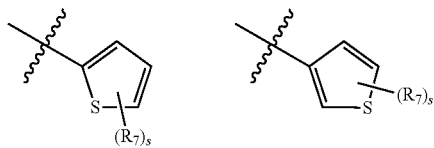

wherein s is 0, 1, 2, or 3; and each $R_7$ is independently selected from the group consisting of halo, perhalo($C_{1-10}$)alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted.

In one particular variation of the above compounds, $R_7$ is independently selected from the group consisting of -cyano, -methoxy, -nitro, -carboxy, -sulfonamido, -tetrazolyl, -aminomethyl, -hydroxymethyl, -phenyl, -halo, —$CONH_2$, —$CONH(C_{1-7})$alkyl, —$CO_2(C_{1-7})$alkyl, —$NH_2$, —OH, —($C_{1-5}$)alkyl, -alkenyl, -alkynyl, ($C_{1-5}$)cycloalkyl, aryl, heteroaryl, and heterocycloalkyl, each substituted or unsubstituted.

In another embodiment, DPP-IV inhibitors of the present invention include compounds comprising:

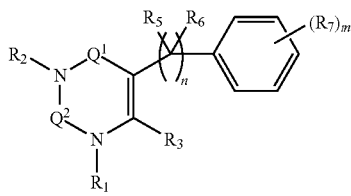

wherein m is 0, 1, 2, 3, 4 or 5;

n is 1, 2, or 3;

$Q^1$ and $Q^2$ are each independently selected from the group consisting of CO, CS, SO, $SO_2$, and C=$NR_9$;

$R_1$ is hydrogen or is selected from the group consisting of halo, perhalo($C_{1-10}$)alkyl, amino, cyano, thio, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, hydroxy, alkoxy, aryloxy, heteroaryloxy, carbonyl group, imino group, sulfonyl group and sulfinyl group, each substituted or unsubstituted;

$R_2$ is hydrogen or selected from the group consisting of ($C_{1-10}$)alkyl, ($C_{3-12}$)cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted;

$R_3$ is selected from the group consisting of perhalo($C_{1-10}$)alkyl, amino, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$) alkyl, imino ($C_{1-3}$)alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;

each $R_5$ and $R_6$ is independently hydrogen or is selected from the group consisting of a substituted or unsubstituted ($C_{1-10}$)alkyl, a substituted or unsubstituted ($C_{1-10}$)alkoxy, cyano, and halo, or where $R_5$ and $R_6$ are taken together to form a ring;

each $R_7$ is independently selected from the group consisting of halo, perhalo($C_{1-10}$)alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted; and $R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted.

In another embodiment, DPP-IV inhibitors of the present invention include compounds comprising:

a member selected from the group consisting of

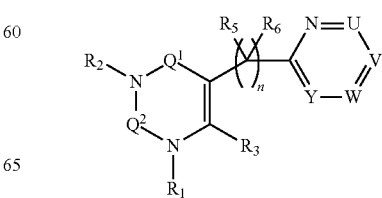

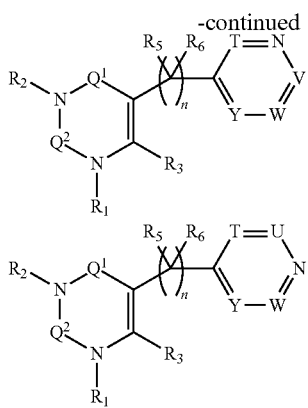

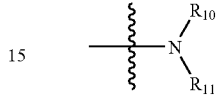

wherein n is 1, 2, or 3;

$Q^1$ and $Q^2$ are each independently selected from the group consisting of CO, CS, SO, $SO_2$, and $C=NR_9$;

each of T, U, V, W and Y is independently nitrogen or $CR_{16}$, provided that no more than two of T, U, V, W and Y are nitrogen;

$R_1$ is hydrogen or is selected from the group consisting of halo, perhalo($C_{1-10}$)alkyl, amino, cyano, thio, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, hydroxy, alkoxy, aryloxy, heteroaryloxy, carbonyl group, imino group, sulfonyl group and sulfinyl group, each substituted or unsubstituted;

$R_2$ is hydrogen or selected from the group consisting of ($C_{1-10}$)alkyl, ($C_{3-12}$)cycloalkyl, ($C_{3-12}$)cycloalkyl($C_{1-5}$)alkyl, hetero($C_{3-12}$)cycloalkyl($C_{1-5}$)alkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, hetero($C_{4-12}$)bicycloaryl($C_{1-5}$)alkyl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted;

$R_3$ is selected from the group consisting of perhalo($C_{1-10}$) alkyl, amino, ($C_{1-10}$)alkyl, cycloalkyl, heterocycloalkyl, arylalkyl, heteroarylalkyl, aryl, heteroaryl, carbonyl ($C_{1-3}$)alkyl, thiocarbonyl ($C_{1-3}$)alkyl, sulfonyl ($C_{1-3}$)alkyl, sulfinyl ($C_{1-3}$) alkyl, imino ($C_{1-3}$)alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;

each $R_5$ and $R_6$ is independently hydrogen or is selected from the group consisting of a substituted or unsubstituted ($C_{1-10}$)alkyl, a substituted or unsubstituted ($C_{1-10}$)alkoxy, cyano, and halo, or where $R_5$ and $R_6$ are taken together to form a ring;

$R_9$ is hydrogen or is selected from the group consisting of alkyl, cycloalkyl, heterocycloalkyl, arylalkyl, heteroarylalkyl, bicycloaryl, and heterobicycloaryl, each substituted or unsubstituted; and each $R_{16}$ is independently selected from the group consisting of halo, perhalo($C_{1-10}$)alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imino group, sulfonyl group and sulfinyl group, each substituted or unsubstituted.

Substituent $R_3$:

In regard to each of the above embodiments and variations, the present invention provides compounds wherein $R_3$ is selected from the group consisting of amino, ($C_{1-10}$)alkyl, cycloalkyl, heterocycloalkyl, arylalkyl, heteroarylalkyl, aryl, and heteroaryl, each substituted or unsubstituted, and a substituted or unsubstituted 3, 4, 5, 6 or 7 membered ring.

Further, according to each of the above embodiments and variations, the present invention also provides compounds wherein $R_3$ comprises the formula

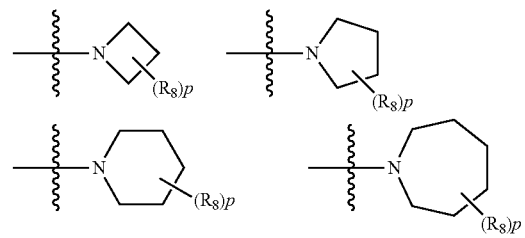

wherein $R_{10}$ and $R_{11}$ are each independently selected from the group consisting of hydrogen, perhalo($C_{1-10}$)alkyl, amino, ($C_{1-10}$)alkyl, ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloaryl, hetero($C_{4-12}$)bicycloaryl, carbonyl ($C_{1-3}$)alkyl, thiocarbonyl ($C_{1-3}$)alkyl, aryl, heteroaryl, hydroxy, alkoxy, aryloxy, heteroaryloxy, carbonyl group, sulfonyl group, and sulfinyl group, each substituted or unsubstituted, or $R_{10}$ and $R_{11}$ are taken together to form a 4, 5, 6, or 7 membered ring, each substituted or unsubstituted.

According to another variation of each of the above embodiments and variations, $R_3$ is a substituted or unsubstituted 3, 4, 5, 6, or 7 membered ring, wherein $R_3$ is a substituted or unsubstituted 3, 4, 5, 6, or 7 membered cycloalkyl, or wherein $R_3$ is a substituted or unsubstituted 4, 5, 6, or 7 membered heterocycloalkyl. In another variation of the above, $R_3$ is a substituted or unsubstituted aryl, or wherein $R_3$ is a substituted or unsubstituted heteroaryl.

In one particular variation of the above embodiments and variations, $R_3$ is selected from the group consisting of

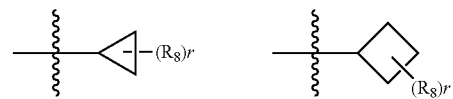

wherein p is 0-12 and each $R_8$ is independently selected from the group consisting of halo, perhalo($C_{1-10}$)alkyl, $CF_3$, cyano, nitro, hydroxy, alkyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, alkoxy, carbonyl group, imino group, sulfonyl group and sulfinyl group, each substituted or unsubstituted.

In another particular variation of the above embodiments and variations, $R_3$ is selected from the group consisting of

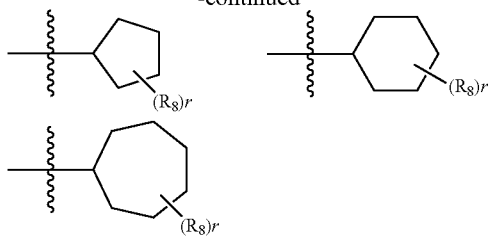

wherein r is 0-13 and each $R_8$ is independently selected from the group consisting of halo, perhalo($C_{1-10}$)alkyl, $CF_3$, cyano, nitro, hydroxy, alkyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, alkoxy, carbonyl group, imino group, sulfonyl group and sulfinyl group, each substituted or unsubstituted.

According to each of the above embodiments and variations, DPP-IV inhibitors of the present invention may comprise compounds wherein $R_3$ is a substituted or unsubstituted heteroaryl selected from the group consisting of furan, thiophene, pyrrole, pyrazole, triazole, isoxazole, oxazole, thiazole, isothiazole, oxadiazole, pyridine, pyridazine, pyrimidine, pyrazine, triazine, benzofuran, isobenzofuran, benzothiophene, isobenzothiophene, imidazole, benzimidazole, indole, isoindole, quinoline, isoquinoline, cinnoline, quinazoline, naphthyridine, pyridopyridine, quinoxaline, phthalazine, and benzothiazole, each substituted or unsubstituted.

Further, according to the above embodiments and variations, $R_3$ may be selected from the group consisting of ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloaryl, and hetero($C_{4-12}$) bicycloaryl, each substituted or unsubstituted. In another variation, $R_3$ is a substituted or unsubstituted ($C_{3-7}$)cycloalkyl ring, optionally comprising O, N(O), N, S, SO, $SO_2$ or a carbonyl group in the ring.

According to each of the above embodiments and variations, $R_3$ may also be substituted such that $R_3$ comprises a substituent selected from the group consisting of a primary, secondary or tertiary amine, a heterocycloalkyl comprising a nitrogen ring atom, and a heteroaryl comprising a nitrogen ring atom.

In particular variations of the present invention, $R_3$ comprises a basic nitrogen atom that is capable of interacting with a carboxylic acid side chain of an active site residue of a protein. In one variation, the basic nitrogen of $R_3$ is separated from the ring atom to which $R_3$ is attached by between 1-5 atoms. In another variation, the basic nitrogen atom forms part of a primary, secondary or tertiary amine. In yet another variation, the basic nitrogen atom is a nitrogen ring atom of a heterocycloalkyl or a heteroaryl.

In one variation of each of the embodiments of the present invention, $R_3$ includes a basic nitrogen that is capable of interacting with a carboxylic acid side chain of a residue in the DP-4 active site and thus contributes to the binding affinity of the compound to DP-4. Based on co-crystal structures obtained by Applicants, the observed interaction between the basic nitrogen substituent and the carboxylic acid appears to be via hydrogen bonding or by the formation of a salt bridge.

The basic nitrogen of $R_3$ in this variation that provides the desired carboxylic acid side chain interaction is not typically directly attached to the ring atom to which $R_3$ is attached. In this regard, the basic nitrogen may be viewed as a substituent of the overall $R_3$ moiety. For example, in the case where $R_3$ is 3-amino-piperidinyl-1-yl, the basic nitrogen is the 3-amino group and not the nitrogen of the piperidine ring. Thus, $R_3$ may be viewed as a substituted piperidine ring further comprising an amine as a basic nitrogen substituent. In a particular variation, the basic nitrogen of $R_3$ is optionally separated from the ring atom to which $R_3$ is attached by between 1-5 atoms.

The basic nitrogen atom moiety of $R_3$ may optionally be selected from the group consisting of a primary, secondary or tertiary amine, a heterocycloalkyl comprising a nitrogen ring atom, a heteroaryl comprising a nitrogen ring atom, as well as other nitrogen containing moieties where the nitrogen can act as a Lewis base. In addition to basic nitrogen containing moieties, it is envisioned that other Lewis bases, such as oxygen with basic lone pairs, may be capable of interacting with a carboxylic acid side chain of a residue in the DP-4 active site.

In certain embodiments, $R_3$ is said to be further substituted with one or more $R_8$ substituents. It is noted that at least one of the $R_8$ substituents may comprise the basic nitrogen atom capable of providing the interaction with the carboxylic acid side chain. In this regard, $R_8$ may optionally comprise a moiety selected from the group consisting of a primary, secondary or tertiary amine, a heterocycloalkyl comprising a nitrogen ring atom, a heteroaryl comprising a nitrogen ring atom, as well as other nitrogen containing moieties where the nitrogen can act as a Lewis base.

Particular examples of moieties with basic nitrogens according to this variation include, but are not limited to —$NH_2$, —NH($C_{1-5}$ alkyl), —N($C_{1-5}$ alkyl)$_2$, piperazine, imidazole, and pyridine. Additional particular $R_3$ groups that comprise a basic nitrogen include, but are not limited to 3-amino-piperidinyl-1-yl, 3-aminomethyl-pyrrolidin-1-yl, 3-aminoazetidin-1-yl, 3-amino-3-methylpiperidin-1-yl, 3-aminocyclopent-1-yl, 3-aminomethylcyclopent-1-yl, 3-aminomethylcyclohex-1-yl, 3-aminohexahydroazepin-1-yl, 3-amino-cyclohex-1-yl, piperazin-1-yl, homopiperazin-1-yl, 3-amino-pyrrolidin-1-yl, R-3-aminopiperidin-1-yl, R-3-amino-3-methylpiperidin-1-yl, 3-amino-cyclohex-1-yl, 3-amino-cyclopent-1-yl, and 3-amino-pyrrolidin-1-yl, each optionally further substituted.

In regard to a particular variation, at least one $R_8$ comprises a basic nitrogen atom that is capable of interacting with a carboxylic acid side chain of an active site residue of a protein. In another particular variation, the basic nitrogen atom forms part of a primary, secondary or tertiary amine. In another variation of the above compounds, the basic nitrogen atom is a nitrogen ring atom of a heterocycloalkyl comprising a nitrogen ring atom or a heteroaryl comprising a nitrogen ring atom.

In one variation of each of the embodiments of the present invention, at least one $R_8$ is a primary, secondary or tertiary amine. In another variation, at least one $R_8$ is a substituted or unsubstituted heterocycloalkyl comprising a nitrogen ring atom or a substituted or unsubstituted heteroaryl comprising a nitrogen ring atom. In yet another particular variation, at least one $R_8$ is selected from the group consisting of —$NH_2$, —NH($C_{1-5}$ alkyl), —N($C_{1-5}$ alkyl)$_2$, piperazine, imidazole, and pyridine.

According to each of the above embodiments and variations, $R_3$ is selected from the group consisting of 3-amino-piperidinyl-1-yl, 3-aminomethyl-pyrrolidin-1-yl, 3-aminoazetidin-1-yl, 3-amino-3-methylpiperidin-1-yl, 3-aminocyclopent-1-yl, 3-aminomethylcyclopent-1-yl, 3-aminomethylcyclohex-1-yl, 3-aminohexahydroazepin-1-yl, 3-amino-cyclohex-1-yl, piperazin-1-yl, homopiperazin-1- yl, 3-amino-pyrrolidin-1-yl, R-3-aminopiperidin-1-yl, R-3-amino-3-methylpiperidin-1-yl, 3-amino-cyclohex-1-yl, 3-amino-cyclopent-1-yl, and 3-amino-pyrrolidin-1-yl, each substituted or unsubstituted.

In one particular variation, at least one of $Q^1$ and $Q^2$ is CO. In another variation of the above compounds, $Q^1$ and $Q^2$ are CO.

Substituent M:

In another particular variation, the present invention provides compounds wherein M is nitrogen. In yet another particular variation, M is $CR_4$ and where $R_4$ is selected from the group consisting of

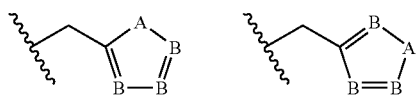

wherein
A is S, O or $NR_{24}$;
B is $CR_{23}$ or N;
$R_{23}$ is independently selected from the group consisting of hydrogen, halo, perhalo($C_{1-10}$)alkyl, amino, thio, cyano, $CF_3$, nitro, ($C_{1-10}$)alkyl, ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloalkyl, hetero($C_{8-12}$)bicycloaryl, carbonyl ($C_{1-3}$)alkyl, thiocarbonyl ($C_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted; and $R_{24}$ is independently selected from the group consisting of hydrogen, perhalo($C_{1-10}$)alkyl, amino, ($C_{1-10}$)alkyl, ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloaryl, hetero($C_{8-12}$)bicycloaryl, carbonyl ($C_{1-3}$)alkyl, thiocarbonyl ($C_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted.

In another particular variation, the present invention provides compounds wherein M is $CR_4$ and where $R_4$ is selected from the group consisting of

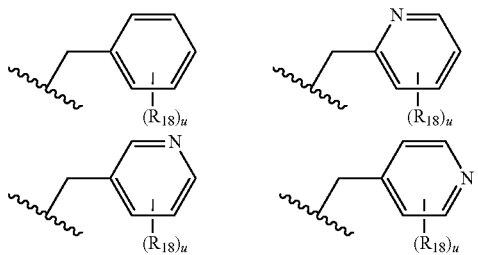

wherein u is 0, 1, 2, 3, 4, or 5; and each $R_{18}$ is independently selected from the group consisting of halo, perhalo($C_{1-10}$) alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imine group, sulfonyl group and sulfinyl group, each substituted or unsubstituted.

In yet another variation, there is provided compounds wherein M is $CR_4$ and where $R_4$ is selected from the group consisting of

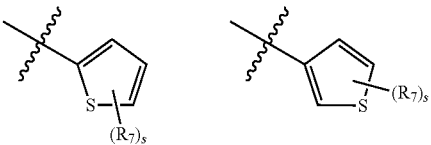

wherein s is 0, 1, 2, or 3; and each $R_7$ is independently selected from the group consisting of halo, perhalo($C_{1-10}$)alkyl, $CF_3$, ($C_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, amino, thio, cyano, nitro, hydroxy, alkoxy, carbonyl group, imino group, sulfonyl group and sulfinyl group, each substituted or unsubstituted.

Substituent $R_5$ and $R_6$:

In particular variations of the present invention, there is provided compounds wherein $R_5$ and $R_6$ are hydrogen. In yet another variation, $R_5$ and $R_6$ are taken together to form a ring. In yet another variation, at least one of $R_5$ and $R_6$ is a halide, such as fluorine.

In another variation of the invention, there is provided compounds wherein at least one of $R_5$ and $R_6$ is a substituted or unsubstituted —($C_{1-8}$)alkylene$R_{13}$, wherein $R_{13}$ is selected from the group consisting of ($C_{3-12}$)cycloalkyl, hetero($C_{4-12}$)cycloalkyl, ($C_{6-12}$)aryl, hetero($C_{5-12}$)aryl, ($C_{9-12}$) bicycloalkyl, hetero($C_{9-12}$)bicycloalkyl, ($C_{9-12}$)bicycloaryl and hetero($C_{4-12}$)bicycloaryl, each substituted or unsubstituted.

In another particular variation of the above compounds, $R_5$ and $R_6$ are hydrogen, m is 1 or 2, and each $R_7$ is independently selected from the group consisting of halo, perhalo($C_{1-10}$) alkyl, $CF_3$, cyano, nitro, hydroxy, alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, alkoxy, carbonyl group, imino group, sulfonyl group and sulfinyl group, each substituted or unsubstituted.

In regard to particular variations of the invention, there is provided compounds wherein two $R_7$ are taken together to form a substituted or unsubstituted fused or bridged ring.

In yet another particular variation, there is provided compounds wherein n is 1, 2 or 3; and $R_5$ and $R_6$ are hydrogen. In another variation, n is 1 or 2; $R_3$ is selected from the group consisting of amino, alkoxy, aryloxy, heteroaryloxy, carbonyl group, imino group, sulfonyl group and sulfinyl group, and a substituted or unsubstituted 4, 5, 6 or 7 membered ring; and $R_5$ and $R_6$ are hydrogen.

In one particular variation of the above compounds, $R_5$ and $R_6$ are hydrogen and $R_7$ is 2-cyano. In another variation of the above compound, n is 1. In yet another particular variation of the above compounds, n is 1, 2 or 3; $R_5$ and $R_6$ are hydrogen; and $R_3$ is selected from the group consisting of ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloaryl, and hetero($C_{4-12}$)bicycloaryl, each substituted or unsubstituted.

According to particular variation of the above compounds, n is 1, 2 or 3; $R_5$ and $R_6$ are hydrogen; and each $R_7$ is independently selected from the group consisting of halo, perhalo ($C_{1-10}$)alkyl, alkenyl, alkynyl, $CF_3$, cyano, nitro, hydroxy, heteroaryl, aryloxy, heteroaryloxy, alkoxy, carbonyl group, imino group, sulfonyl group and sulfinyl group, each substituted or unsubstituted.

Substituent R$_7$:

In particular variations of the above, there is provided compounds wherein two R$_7$ are taken together to form a substituted or unsubstituted fused ring. In another particular variation, two R$_7$ are taken together to form a substituted or unsubstituted bridged ring.

According to particular variations of the above compounds, two of T, U, V, W and Y are taken together and substituted through available valencies to form a substituted or unsubstituted ring fused or bridged to the ring formed by T U, V, W and Y.

Substituent R$_2$:

According to each of the above embodiments and variations, the present invention provides compounds wherein R$_2$ is a substituted or unsubstituted (C$_{1-10}$)alkyl. In another variation, R$_2$ is a substituted or unsubstituted (C$_{1-4}$)alkyl. In yet another variation, R$_2$ is —Y-Z wherein Y a linker providing 1, 2 or 3 atom separation between Z and the ring to which Y is attached, wherein the atoms of the linker providing the separation are selected from the group consisting of carbon, oxygen, nitrogen, and sulfur; and Z is hydrogen or selected from the group consisting of (C$_{1-10}$)alkyl, (C$_{3-12}$)cycloalkyl, hetero (C$_{3-12}$)cycloalkyl, aryl(C$_{1-10}$)alkyl, heteroaryl(C$_{1-5}$)alkyl, (C$_{9-12}$)bicycloaryl, hetero(C$_{4-12}$)bicycloaryl, carbonyl (C$_{1-3}$) alkyl, thiocarbonyl (C$_{1-3}$)alkyl, sulfonyl (C$_{1-3}$)alkyl, sulfinyl (C$_{1-3}$)alkyl, imino (C$_{1-3}$)alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

In yet another variation, R$_2$ is selected from the group consisting of

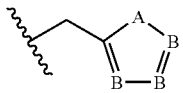 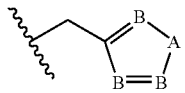

wherein A is S, O or NR$_{24}$; B is CR$_{23}$ or N; R$_{23}$ is independently selected from the group consisting of hydrogen, halo, perhalo(C$_{1-10}$)alkyl, amino, thio, cyano, CF$_3$, nitro, (C$_{1-10}$) alkyl, (C$_{3-12}$)cycloalkyl, hetero(C$_{3-12}$)cycloalkyl, aryl(C$_{1-10}$) alkyl, heteroaryl (C$_{1-5}$)alkyl, (C$_{9-12}$)bicycloaryl, hetero (C$_{8-12}$)bicycloaryl, carbonyl (C$_{1-3}$)alkyl, thiocarbonyl (C$_{1-3}$) alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted; and R$_{24}$ is independently selected from the group consisting of hydrogen, perhalo (C$_{1-10}$)alkyl, amino, (C$_{1-10}$)alkyl, (C$_{3-12}$)cycloalkyl, hetero (C$_{3-12}$)cycloalkyl, aryl(C$_{1-10}$)alkyl, heteroaryl (C$_{1-5}$)alkyl, (C$_{9-12}$)bicycloaryl, hetero(C$_{8-12}$)bicycloaryl, carbonyl (C$_{1-3}$) alkyl, thiocarbonyl (C$_{1-3}$)alkyl, aryl, heteroaryl, hydroxy, alkoxy, aryloxy, heteroaryloxy, imino group, carbonyl group, aminosulfonyl, alkylsulfonyl, arylsulfonyl, heteroarylsulfonyl, and sulfinyl group, each substituted or unsubstituted.

In yet another variation, R$_2$ is selected from the group consisting of

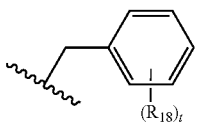 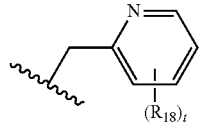

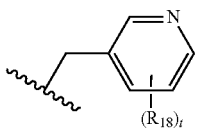 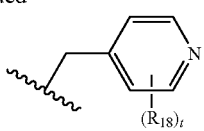

wherein t is 0, 1, 2, 3, 4, or 5; and each R$_{18}$ is independently selected from the group consisting of halo, perhalo(C$_{1-10}$) alkyl, CF$_3$, (C$_{1-10}$)alkyl, alkenyl, alkynyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, cyano, nitro, hydroxy, alkoxy, carbonyl group, imine group, sulfonyl group and sulfinyl group, each substituted or unsubstituted.

Particular examples of DPP-IV inhibitors according to the present invention include, but are not limited to:

2-(6-Chloro-2,4-dioxo-3,4-dihydro-2H-pyrimidin-1-ylmethyl)-benzonitrile;

(6-Chloro-3-methyl-2,4-dioxo-3,4-dihydro-2H-pyrimidin-1-ylmethyl)-benzonitrile;

2-{6-[3-Amino-piperidin-1-yl]-3-methyl-2,4-dioxo-3,4-dihydro-2H-pyrimidin-1-ylmethyl}-benzonitrile;

2-{6-[3-Amino-piperidin-1-yl]-3-ethyl-2,4-dioxo-3,4-dihydro-2H-pyrimidin-1-ylmethyl}-benzonitrile;

2-{6-[3-Amino-piperidin-1-yl]-2,4-dioxo-3,4-dihydro-2H-pyrimidin-1-ylmethyl}-benzonitrile;

2-{6-[3-Amino-piperidin-1-yl]-5-chloro-3-methyl-2,4-dioxo-3,4-dihydro-2H-pyrimidin-1-ylmethyl}-benzonitrile;

6-[3-Amino-piperidin-1-yl]-1-(2-bromo-benzyl)-1H-pyrimidine-2,4-dione;

6-[3-Amino-piperidin-1-yl]-1-(2-iodo-benzyl)-1H-pyrimidine-2,4-dione;

6-[3-Amino-piperidin-1-yl]-1-(2-bromo-5-fluoro-benzyl)-3-methyl-1H-pyrimidine-2,4-dione;

6-[3-Amino-piperidin-1-yl]-1-(2-chloro-5-fluoro-benzyl)-3-methyl-1H-pyrimidine-2,4-dione;

6-[3-Amino-piperidin-1-yl]-1-(2-chloro-4-fluoro-benzyl)-3-methyl-1H-pyrimidine-2,4-dione;

6-[3-Amino-piperidin-1-yl]-1-(2-bromo-benzyl)-3-methyl-1H-pyrimidine-2,4-dione;

2-{6-[Azepan-3(±)-ylamino]-3-methyl-2,4-dioxo-3,4-dihydro-2H-pyrimidin-1-ylmethyl}-benzonitrile (14);

2-{6-[3(±)-Amino-azepan-1-yl]-3-methyl-2,4-dioxo-3,4-dihydro-2H-pyrimidin-1-ylmethyl}-benzonitrile;

2-[6-(2-Amino-ethylamino)-3-ethyl-2,4-dioxo-3,4-dihydro-2H-pyrimidin-1-ylmethyl]-benzonitrile;

2-{6-[3-Amino-piperidin-1-yl]-3-(3-cyano-benzyl)-2,4-dioxo-3,4-dihydro-2H-pyrimidin-1-ylmethyl}-benzonitrile;

2-{6-[3-Amino-piperidin-1-yl]-3-(2-cyano-benzyl)-2,4-dioxo-3,4-dihydro-2H-pyrimidin-1-ylmethyl}-benzonitrile;

2-{6-[3-Amino-piperidin-1-yl]-3-(4-cyano-benzyl)-2,4-dioxo-3,4-dihydro-2H-pyrimidin-1-ylmethyl}-benzonitrile;

[6-(3-Amino-piperidin-1-yl)-3-(1H-benzoimidazol-2-ylmethyl)-2,4-dioxo-3,4-dihydro-2H-pyrimidin-1-ylmethyl]-benzonitrile;

2-{6-[3-Amino-piperidin-1-yl]-2,4-dioxo-3-(4-pyrazol-1-yl-benzyl)-3,4-dihydro-2H-pyrimidin-1-ylmethyl}-benzonitrile;

2-{6-[3-Amino-piperidin-1-yl]-2,4-dioxo-3-(3-pyrrol-1-yl-benzyl)-3,4-dihydro-2H-pyrimidin-1-ylmethyl}-benzonitrile;

6-[3-Amino-piperidin-1-yl]-3-(2-cyano-benzyl)-2,6-dioxo-3,6-dihydro-2H-pyrimidin-1-ylmethyl]-thiophene-3-carbonitrile;

3-{4-[3-Amino-piperidin-1-yl]-3-(2-cyano-benzyl)-2,6-dioxo-3,6-dihydro-2H-pyrimidin-1-ylmethyl}-benzoic acid methyl ester;

3-{4-[3-Amino-piperidin-1-yl]-3-(2-cyano-benzyl)-2,6-dioxo-3,6-dihydro-2H-pyrimidin-1-ylmethyl}-benzoic acid;

6-[3-Amino-piperidin-1-yl]-1,3-bis-(2-bromo-5-fluoro-benzyl)-1H-pyrimidine-2,4-dione;

2-{6-[3(R)-Amino-piperidin-1-yl]-5-chloro-2,4-dioxo-3,4-dihydro-2H-pyrimidin-1-ylmethyl}-benzonitrile;

6-[3(R)-Amino-piperidin-1-yl]-1-(2,5-di-chloro-benzyl)-3-methyl-1H-pyrimidine-2,4-dione;

6-[3(R)-Amino-piperidin-1-yl]-1-(2-chloro-3,6-di-fluoro-benzyl)-3-methyl-1H-pyrimidine-2,4-dione;

(R)-2-((6-(3-amino-3-methylpiperidin-1-yl)-3-methyl-2,4-dioxo-3,4-dihydropyrimidin-1(2H)-yl)methyl)-4-fluorobenzonitrile; and 2-[6-(3-Amino-piperidin-1-yl)-3-methyl-2,4-dioxo-3,4-dihydro-2H-pyrimidin-1-ylmethyl]-4-fluoro-benzonitrile.

Particular examples of DPP-IV inhibitors according to the present invention further include:

2-{6-[3(R)-Amino-piperidin-1-yl]-3-methyl-2,4-dioxo-3,4-dihydro-2H-pyrimidin-1-ylmethyl}-benzonitrile;

2-{6-[3(R)-Amino-piperidin-1-yl]-3-ethyl-2,4-dioxo-3,4-dihydro-2H-pyrimidin-1-ylmethyl}-benzonitrile;

2-{6-[3(R)-Amino-piperidin-1-yl]-2,4-dioxo-3,4-dihydro-2H-pyrimidin-1-ylmethyl}-benzonitrile;

{6-[3(R)-Amino-piperidin-1-yl]-5-chloro-3-methyl-2,4-dioxo-3,4-dihydro-2H-pyrimidin-1-ylmethyl}-benzonitrile;

6-[3(R)-Amino-piperidin-1-yl]-1-(2-bromo-benzyl)-1H-pyrimidine-2,4-dione;

6-[3(R)-Amino-piperidin-1-yl]-1-(2-iodo-benzyl)-1H-pyrimidine-2,4-dione;

6-[3(R)-Amino-piperidin-1-yl]-1-(2-bromo-5-fluoro-benzyl)-3-methyl-1H-pyrimidine-2,4-dione;

6-[3(R)-Amino-piperidin-1-yl]-1-(2-chloro-5-fluoro-benzyl)-3-methyl-1H-pyrimidine-2,4-dione;

6-[3(R)-Amino-piperidin-1-yl]-1-(2-chloro-4-fluoro-benzyl)-3-methyl-1H-pyrimidine-2,4-dione;

6-[3(R)-Amino-piperidin-1-yl]-1-(2-bromo-benzyl)-3-methyl-1H-pyrimidine-2,4-dione;

2-{6-[3(R)-Amino-piperidin-1-yl]-3-(3-cyano-benzyl)-2,4-dioxo-3,4-dihydro-2H-pyrimidin-1-ylmethyl}-benzonitrile;

2-{6-[3(R)-Amino-piperidin-1-yl]-3-(2-cyano-benzyl)-2,4-dioxo-3,4-dihydro-2H-pyrimidin-1-ylmethyl}-benzonitrile;

2-{6-[3(R)-Amino-piperidin-1-yl]-3-(4-cyano-benzyl)-2,4-dioxo-3,4-dihydro-2H-pyrimidin-1-ylmethyl}-benzonitrile;

2-[6-(3-Amino-piperidin-1-yl)-3-(1H-benzoimidazol-2-ylmethyl)-2,4-dioxo-3,4-dihydro-2H-pyrimidin-1-ylmethyl]-benzonitrile 2-{6-[3(R)-Amino-piperidin-1-yl]-2,4-dioxo-3-(4-pyrazol-1-yl-benzyl)-3,4-dihydro-2H-pyrimidin-1-ylmethyl}-benzonitrile;

2-{6-[3(R)-Amino-piperidin-1-yl]-2,4-dioxo-3-(3-pyrrol-1-yl-benzyl)-3,4-dihydro-2H-pyrimidin-1-ylmethyl}-benzonitrile;

6-[3(R)-Amino-piperidin-1-yl]-3-(2-cyano-benzyl)-2,6-dioxo-3,6-dihydro-2H-pyrimidin-1-ylmethyl]-thiophene-3-carbonitrile;

3-{4-[3(R)-Amino-piperidin-1-yl]-3-(2-cyano-benzyl)-2,6-dioxo-3,6-dihydro-2H-pyrimidin-1-ylmethyl}-benzoic acid methyl ester;

3-{4-[3(R)-Amino-piperidin-1-yl]-3-(2-cyano-benzyl)-2,6-dioxo-3,6-dihydro-2H-pyrimidin-1-ylmethyl}-benzoic acid;

6-[3(R)-Amino-piperidin-1-yl]-1,3-bis-(2-bromo-5-fluoro-benzyl)-1H-pyrimidine-2,4-dione; and

[6-(3(R)-Amino-piperidin-1-yl)-3-methyl-2,4-dioxo-3,4-dihydro-2H-pyrimidin-1-ylmethyl]-4-fluoro-benzonitrile.

In another embodiment, the present invention provides the compounds in the form of a pharmaceutically acceptable salt.

In yet another embodiment, the present invention provides the compounds present in a mixture of stereoisomers. In yet another embodiment, the present invention provides the compounds as a single stereoisomer.

In yet another embodiment, the present invention provides pharmaceutical compositions comprising the compound as an active ingredient. In yet another variation, the present invention provides pharmaceutical compositions wherein the composition is a solid formulation adapted for oral administration. In yet another particular variation, the present invention provides pharmaceutical composition wherein the composition is a tablet. In another particular variation, the present invention provides the pharmaceutical composition wherein the composition is a liquid formulation adapted for oral administration. In yet another particular variation, the present invention provides pharmaceutical composition wherein the composition is a liquid formulation adapted for parenteral administration.

In yet another particular variation, the present invention provides the pharmaceutical composition comprising the compound of the invention wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraocularly, via local delivery (for example by catheter or stent), subcutaneously, intraadiposally, intraarticularly, and intrathecally.

In another embodiment, the present invention provides a kit comprising a compound of the present invention and instructions which comprise one or more forms of information selected from the group consisting of indicating a disease state for which the compound is to be administered, storage information for the compound, dosing information and instructions regarding how to administer the compound. In another embodiment, the present invention provides the kit that comprises the compound in a multiple dose form.

In another embodiment, the present invention provides an article of manufacture comprising a compound of the present invention, and packaging materials. In another variation, the packaging material comprises a container for housing the compound. In yet another variation, the invention provides the article of manufacture wherein the container comprises a label indicating one or more members of the group consisting of a disease state for which the compound is to be administered, storage information, dosing information and/or instructions regarding how to administer the composition.

In another variation, the present invention provides the article of manufacture wherein the article of manufacture comprises the compound in a multiple dose form.

In another embodiment, the present invention provides a method of inhibiting DPP-IV comprising contacting DPP-IV with a compound according to the present invention.

In another embodiment, the present invention provides a method of inhibiting DPP-IV comprising causing a compound according to the present invention to be present in a subject in order to inhibit DPP-IV in vivo.

In another embodiment, the present invention provides a method of inhibiting DPP-IV comprising: administering a first compound to a subject that is converted in vivo to a second compound wherein the second compound inhibits DPP-IV in vivo, the second compound being a compound of the present invention.

In another embodiment, the present invention provides therapeutic method comprising: administering a compound according to the present invention to a subject.

In another embodiment, the present invention provides a method of treating a disease state for which DPP-IV possesses activity that contributes to the pathology and/or symptomology of the disease state, the method comprising causing a compound of the present invention to be present in a subject in a therapeutically effective amount for the disease state.

In another embodiment, the present invention provides a method of treating cancer in a patient in need thereof, comprising administering to said patient a therapeutically effective amount of a compound according to the present invention.

In another embodiment, the present invention provides a method of treating a disease where the disease is type I or type II diabetes.

In another embodiment, the present invention provides a method of treating autoimmune disorders such as, but not limited to, rheumatoid arthritis, psoriasis, and multiple sclerosis in a patient in need thereof, comprising administering to said patient a therapeutically effective amount of a compound according to the present invention.

In yet another embodiment, the present invention provides a method of treating cancer where the cancer treated is colorectal, prostate, breast, thyroid, skin, lung, or head and neck.

In another embodiment, the present invention provides a method of treating a condition characterized by inadequate lymphocyte or hemopoietic cell activation or concentration in a patient in need thereof, comprising administering to said patient a therapeutically effective amount of a compound according to the present invention.

In another embodiment, the present invention provides a method of treating HIV infection in a patient in need thereof, comprising administering to said patient a therapeutically effective amount of a compound according to the present invention.

In yet another embodiment, the present invention provides a method of treating a condition characterized by inadequate lymphocyte or hemopoietic cell activation or concentration in a patient in need thereof, wherein the condition is a side effect of chemotherapy or radiation therapy.

In yet another embodiment, the present invention provides a method of treating a condition characterized by inadequate lymphocyte or hemopoietic cell activation or concentration in a patient in need thereof, wherein the condition is a result of kidney failure.

In yet another embodiment, the present invention provides a method of treating a condition characterized by inadequate lymphocyte or hemopoietic cell activation or concentration in a patient in need thereof, wherein the condition is a result of a bone marrow disorder.

In another embodiment, the present invention provides a method of treating a condition characterized by immunodeficiency symptoms in a patient in need thereof, comprising administering to said patient a therapeutically effective amount of a compound according to the present invention.

In yet another embodiment, the present invention provides a process for producing a pyrimidin-dione of the formula:

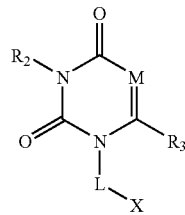

wherein
M is N or $CR_4$;
$R_2$ is hydrogen or selected from the group consisting of $(C_{1-10})$alkyl, $(C_{3-12})$cycloalkyl, $(C_{3-12})$cycloalkyl$(C_{1-5})$alkyl, hetero$(C_{3-12})$cycloalkyl$(C_{1-5})$alkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, hetero$(C_{4-12})$bicycloaryl$(C_{1-5})$alkyl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, carbonyl group, imino group, sulfonyl group and sulfinyl group, each substituted or unsubstituted;
$R_3$ is selected from the group consisting of perhalo$(C_{1-10})$alkyl, amino, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, hydroxy, alkoxy, aryloxy, heteroaryloxy, carbonyl group, imino group, sulfonyl group and sulfinyl group, each substituted or unsubstituted, and a substituted or unsubstituted 3, 4, 5, 6 or 7 membered ring;
$R_4$ is hydrogen or is selected from the group consisting of halo, perhalo$(C_{1-10})$alkyl, amino, cyano, thio, $(C_{1-10})$alkyl, cycloalkyl, heterocycloalkyl, arylalkyl, heteroarylalkyl, aryl, heteroaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, hydroxy, alkoxy, aryloxy, heteroaryloxy, carbonyl group, imino group, sulfonyl group and sulfinyl group, each substituted or unsubstituted;
L is a linker providing 1, 2 or 3 atom separation between X and the ring to which L is attached, wherein the atoms of the linker providing the separation are selected from the group consisting of carbon, oxygen, nitrogen, and sulfur; and
X is selected from the group consisting of $(C_{1-10})$alkyl, $(C_{3-12})$cycloalkyl, hetero$(C_{3-12})$cycloalkyl, aryl$(C_{1-10})$alkyl, heteroaryl$(C_{1-5})$alkyl, $(C_{9-12})$bicycloaryl, hetero$(C_{4-12})$bicycloaryl, carbonyl $(C_{1-3})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted;
the process comprising the steps of:
(i) contacting a compound of the formula A

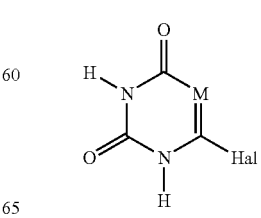

wherein Hal is halogen;
with a compound of the formula B

X-L-LG   B wherein LG is a leaving group;
L is a linker providing 1, 2 or 3 atom separation between X and the ring to which L is attached, wherein the atoms of the linker providing the separation are selected from the group consisting of carbon, oxygen, nitrogen, and sulfur; and
X is selected from the group consisting of $(C_{1-10})$alkyl, $(C_{3-12})$cycloalkyl, hetero$(C_{3-12})$cycloalkyl, aryl $(C_{1-10})$alkyl, heteroaryl$(C_{1-5})$alkyl, $(C_{9-12})$bicycloaryl, hetero$(C_{4-12})$bicycloaryl, carbonyl $(C_{1-3})$ alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted; under conditions sufficient to produce a compound of the formula C

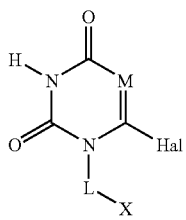

C (ii) contacting the compound of formula C with a compound of formula D $R_2$-LG'   D wherein LG' is a leaving group;
under conditions sufficient to produce a compound of the formula E;

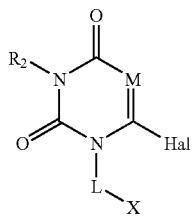

E wherein $R_2$ is selected from the group consisting of $(C_{1-10})$alkyl, $(C_{3-12})$cycloalkyl, $(C_{3-12})$cycloalkyl $(C_{1-5})$alkyl, hetero$(C_{3-12})$cycloalkyl$(C_{1-5})$alkyl, hetero$(C_{3-12})$cycloalkyl, aryl$(C_{1-10})$alkyl, heteroaryl $(C_{1-5})$alkyl, $(C_{9-12})$bicycloaryl, hetero$(C_{4-12})$bicycloaryl, hetero$(C_{4-12})$bicycloaryl$(C_{1-5})$alkyl, carbonyl $(C_{1-13})$alkyl, thiocarbonyl $(C_{1-3})$alkyl, sulfonyl $(C_{1-3})$alkyl, sulfinyl $(C_{1-3})$alkyl, imino $(C_{1-3})$alkyl, amino, aryl, heteroaryl, hydroxy, alkoxy, aryloxy, heteroaryloxy, carbonyl group, imino group, sulfonyl group and sulfinyl group, each substituted or unsubstituted; and
(iii) contacting the compound of formula E with a compound of formula $R_3$—H under conditions sufficient to produce the pyrimidin-dione.

In one variation the pyrimidin-dione product is further converted to an acid addition salt. In particular variations, the acid addition salt is selected from the group consisting of acetate, citrate, hydrochloride, L-lactate, succinate, sulfate, p-toluenesulfonate, benzenesulfonate, benzoate, methanesulfonate, naphthylene-2-sulfonate, propionate, p-toluenesulfonate, hydrobromate, hydroiodate, R-mandelate, and L-tartrate.

In another variation of each of the above embodiments and variations, Hal is selected from the group consisting of Br, Cl and F in the compound of formula A.

In yet another variation of each of the above embodiments and variations, the leaving group LG is selected from the group consisting of Br, Cl and I.

In a further variation of each of the above embodiments and variations, step (ii) further comprises the addition of a base. In particular variations, the base is potassium carbonate.

In still another variation of each of the above embodiments and variations, product E is further purified before subjecting it to step (iii). In a particular variation, the purification of product E is performed by solvent washes and/or by chromatography.

In another variation of each of the above embodiments and variations, $R_3$—H is a secondary amine or an amine hydrochloride. In a particular variation, $R_3$—H is selected from the group consisting of

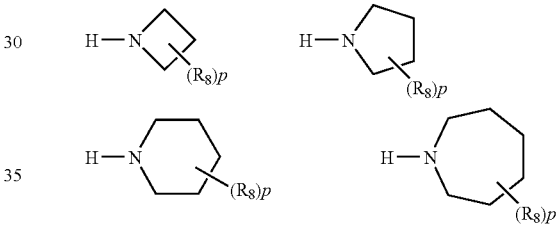

wherein p is 0-12 and each $R_8$ is independently selected from the group consisting of halo, perhalo$(C_{1-10})$alkyl, $CF_3$, cyano, nitro, hydroxy, alkyl, aryl, heteroaryl, aminosulfonyl, alkylsulfonyl, arylsulfonyl, heteroarylsulfonyl, aryloxy, heteroaryloxy, arylalkyl, heteroarylalkyl, cycloalkyl, heterocycloalkyl, amino, thio, alkoxy, carbonyl group, imino group, sulfonyl group and sulfinyl group, each substituted or unsubstituted, or the mono- or di-hydrochloride salt.

In yet another variation of each of the above embodiments and variations, step iii) further comprises purifying the product by washing the product with one or more organic solvents or mixtures of solvents and/or by column chromatography.

In a further variation of each of the above embodiments and variations, L is selected from the group consisting of —CH$_2$—, —CH$_2$CH$_2$—, —CH$_2$CH$_2$CH$_2$—, —C(O)—, —CH$_2$C(O)—, —C(O)CH$_2$—, —CH$_2$—C(O)CH$_2$—, —C(O)CH$_2$CH$_2$—, —CH$_2$CH$_2$C(O)—, —O—, —OCH$_2$—, —CH$_2$O—, —CH$_2$OCH$_2$—, —OCH$_2$CH$_2$—, —CH$_2$CH$_2$O—, —N(CH$_3$)—, —NHCH$_2$—, —CH$_2$NH—, —CH$_2$NHCH$_2$—, —NHCH$_2$CH$_2$—, —CH$_2$CH$_2$NH—, —NH—C(O)—, —NCH$_3$—C(O)—, —C(O)NH—, —C(O)NCH$_3$—, —NHC(O)CH$_2$—, —C(O)NHCH$_2$—, —C(O)CH$_2$NH—, —CH$_2$NHC(O)—, —CH$_2$C(O)NH—, —NHCH$_2$C(O)—, —S—, —SCH$_2$—, —CH$_2$S—, —SCH$_2$CH$_2$—, —CH$_2$SCH$_2$—, —CH$_2$CH$_2$S—, —C(O)S—, —C(O)SCH$_2$—, —CH$_2$C(O)S—, —C(O)CH$_2$S—, and —CH$_2$SC(O)—, each substituted or unsubstituted. In a particular variation, L is selected from the group consisting of —CH$_2$—, —C(O)—, —CH$_2$C(O)—, —C(O)CH$_2$—, —CH$_2$—C(O)CH$_2$—, —C(O)CH$_2$CH$_2$—, and —CH$_2$CH$_2$C(O)—, each substituted or unsubstituted.

In still another variation of each of the above embodiments and variations, -L-X taken together is selected from the group consisting of —(CH$_2$)-(2-cyano)phenyl; —(CH$_2$)-(3-cyano)phenyl; —(CH$_2$)-(2-hydroxy)phenyl; —(CH$_2$)-(3-hydroxy)phenyl; —(CH$_2$)-(2-alkenyl)phenyl; —(CH$_2$)-(3-alkenyl)phenyl; —(CH$_2$)-(2-alkynyl)phenyl; —(CH$_2$)-(3-alkynyl)phenyl; —(CH$_2$)-(2-methoxy)phenyl; —(CH$_2$)-(3-methoxy)phenyl; —(CH$_2$)-(2-nitro)phenyl; —(CH$_2$)-(3-nitro)phenyl; —(CH$_2$)-(2-carboxy)phenyl; —(CH$_2$)-(3-carboxy)phenyl; —(CH$_2$)-(2-carboxamido)phenyl; —(CH$_2$)-(3-carboxamido)phenyl; —(CH$_2$)-(2-sulfonamido)phenyl; —(CH$_2$)-(3-sulfonamido)phenyl; —(CH$_2$)-(2-tetrazolyl)phenyl; —(CH$_2$)-(3-tetrazolyl)phenyl; —(CH$_2$)-(2-aminomethyl)phenyl; —(CH$_2$)-(3-aminomethyl)phenyl; —(CH$_2$)-(2-hydroxymethyl)phenyl; —(CH$_2$)-(3-hydroxymethyl)phenyl; —(CH$_2$)-(2-phenyl)phenyl; —(CH$_2$)-(3-phenyl)phenyl; —(CH$_2$)-(2-halo)phenyl; —(CH$_2$)-(3-halo)phenyl; —(CH$_2$)-(2-CONH$_2$)phenyl; —(CH$_2$)-(3-CONH$_2$)phenyl; —(CH$_2$)-(2-CONH(C$_{1-7}$)alkyl)phenyl; —(CH$_2$)-(3-CONH(C$_{1-7}$)alkyl)phenyl; —(CH$_2$)-(2-CO$_2$(C$_{1-7}$)alkyl)phenyl; —(CH$_2$)-(3-CO$_2$(C$_{1-7}$)alkyl)phenyl; —(CH$_2$)-(2-NH$_2$)phenyl; —(CH$_2$)-(3-NH$_2$)phenyl; —(CH$_2$)-(2-(C$_{3-7}$)alkyl)phenyl; —(CH$_2$)-(3-(C$_{3-7}$)alkyl)phenyl; —(CH$_2$)-(2-(C$_{3-7}$)cycloalkyl)phenyl; —(CH$_2$)-(3-(C$_{3-7}$)cycloalkyl)phenyl; —(CH$_2$)-(2-aryl)phenyl; —(CH$_2$)-(3-aryl)phenyl; —(CH$_2$)-(2-heteroaryl)phenyl; —(CH$_2$)-(3-heteroaryl)phenyl; —(CH$_2$)-2-bromo-5-fluoro phenyl; —(CH$_2$)-2-chloro-5-fluoro phenyl; —(CH$_2$)-2-cyano-5-fluoro phenyl; —(CH$_2$)-2,5-dichloro phenyl; —(CH$_2$)-2,5-difluoro phenyl; —(CH$_2$)-2,5-dibromo phenyl; —(CH$_2$)-2-bromo-3,5-difluoro phenyl; —(CH$_2$)-2-chloro-3,5-difluoro phenyl; —(CH$_2$)-2,3,5-trifluoro phenyl; —(CH$_2$)-2,3,5,6-tetrafluorophenyl; —(CH$_2$)-2-bromo-3,5,6-trifluoro phenyl; —(CH$_2$)-2-chloro-3,5,6-trifluoro phenyl; —(CH$_2$)-2-cyano-3,5-difluoro phenyl; —(CH$_2$)-2-cyano-3,5,6-trifluoro phenyl; —(CH$_2$)-(2-heterocycloalkyl)phenyl; and —(CH$_2$)-(3-heterocycloalkyl)phenyl, each substituted or unsubstituted.

In a further variation of each of the above embodiments and variations, M is CH, and R$_3$ comprises the formula

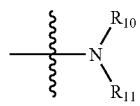

wherein R$_{10}$ and R$_{11}$ are each independently selected from the group consisting of hydrogen, perhalo(C$_{1-10}$)alkyl, amino, (C$_{1-10}$)alkyl, (C$_{3-12}$)cycloalkyl, hetero(C$_{3-12}$)cycloalkyl, aryl(C$_{1-10}$)alkyl, heteroaryl (C$_{1-5}$)alkyl, (C$_{9-12}$)bicycloaryl, hetero(C$_{4-12}$)bicycloaryl, carbonyl (C$_{1-3}$)alkyl, thiocarbonyl (C$_{1-3}$)alkyl, aryl, heteroaryl, hydroxy, alkoxy, aryloxy, heteroaryloxy, carbonyl group, sulfonyl group, and sulfinyl group, each substituted or unsubstituted, or R$_{10}$ and R$_{11}$ are taken together to form a 4, 5, 6, or 7 membered ring, each substituted or unsubstituted.

In yet a further variation, M is CH and R$_3$ is selected from the group consisting of 3-amino-piperidinyl-1-yl, 3-aminomethyl-pyrrolidin-1-yl, 2-aminoazetidin-1-yl, 3-amino-3-methylpiperidin-1-yl, 3-aminocyclopent-1-yl, 3-aminomethylcyclopent-1-yl, 3-aminomethylcyclohex-1-yl, 3-aminohexahydroazepin-1-yl, 3-amino-cyclohex-1-yl, piperazin-1-yl, homopiperazin-1-yl, 3-amino-pyrrolidin-1-yl, R-3-aminopiperidin-1-yl, R-3-amino-3-methylpiperidin-1-yl, 3-amino-cyclohex-1-yl, 3-amino-cyclopent-1-yl, and 3-amino-pyrrolidin-1-yl, each substituted or unsubstituted.

In still a further variation, M is CH and R$_2$ is a substituted or unsubstituted (C$_{1-10}$)alkyl.

In another of its embodiments, the present invention provides a process for producing a pyrimidin-dione of the formula

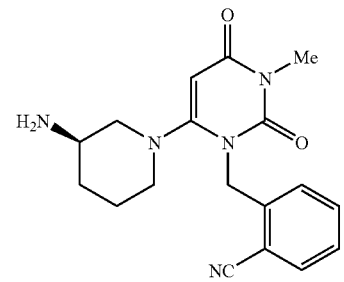

comprising:

(i) admixing 6-chloro-1H-pyrimidine-2,4-dione with an aryl halide of the formula

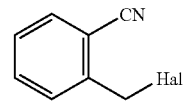

where Hal is Br, Cl, or I, under conditions sufficient to produce a compound of the formula

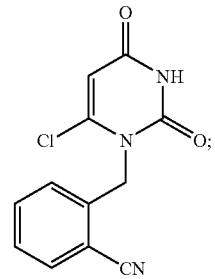

(ii) alkylating the above product with a methyl halide under conditions sufficient to form a compound of the formula

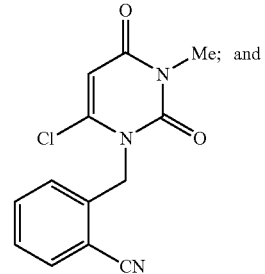

(iii) condensing the above product with a compound of the formula

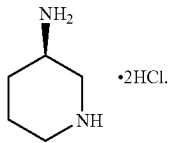

·2HCl.

In one variation of the above embodiment, the process for producing a pyrimidin-dione further comprises the formation of an acid addition salt. In one particular variation, the acid addition salt is a benzoate salt.

In another variation of each of the above embodiments and variations, the pyrimidin-dione is selected from the group consisting of:

2-(6-Chloro-2,4-dioxo-3,4-dihydro-2H-pyrimidin-1-ylmethyl)-benzonitrile;
2-(6-Chloro-3-methyl-2,4-dioxo-3,4-dihydro-2H-pyrimidin-1-ylmethyl)-benzonitrile;
2-{6-[3-Amino-piperidin-1-yl]-3-methyl-2,4-dioxo-3,4-dihydro-2H-pyrimidin-1-ylmethyl}-benzonitrile;
2-{6-[3-Amino-piperidin-1-yl]-3-ethyl-2,4-dioxo-3,4-dihydro-2H-pyrimidin-1-ylmethyl}-benzonitrile;
2-{6-[3-Amino-piperidin-1-yl]-2,4-dioxo-3,4-dihydro-2H-pyrimidin-1-ylmethyl}-benzonitrile;
2-{6-[3-Amino-piperidin-1-yl]-5-chloro-3-methyl-2,4-dioxo-3,4-dihydro-2H-pyrimidin-1-ylmethyl}-benzonitrile;
6-[3-Amino-piperidin-1-yl]-1-(2-bromo-benzyl)-1H-pyrimidine-2,4-dione;
6-[3-Amino-piperidin-1-yl]-1-(2-iodo-benzyl)-1H-pyrimidine-2,4-dione;
6-[3-Amino-piperidin-1-yl]-1-(2-bromo-5-fluoro-benzyl)-3-methyl-1H-pyrimidine-2,4-dione;
6-[3-Amino-piperidin-1-yl]-1-(2-chloro-5-fluoro-benzyl)-3-methyl-1H-pyrimidine-2,4-dione;
6-[3-Amino-piperidin-1-yl]-1-(2-chloro-4-fluoro-benzyl)-3-methyl-1H-pyrimidine-2,4-dione;
6-[3-Amino-piperidin-1-yl]-1-(2-bromo-benzyl)-3-methyl-1H-pyrimidine-2,4-dione;
2-{6-[Azepan-3(±)-ylamino]-3-methyl-2,4-dioxo-3,4-dihydro-2H-pyrimidin-1-ylmethyl}-benzonitrile (14);
2-{6-[3(±)-Amino-azepan-1-yl]-3-methyl-2,4-dioxo-3,4-dihydro-2H-pyrimidin-1-ylmethyl}-benzonitrile;
[6-(2-Amino-ethylamino)-3-ethyl-2,4-dioxo-3,4-dihydro-2H-pyrimidin-1-ylmethyl]-benzonitrile;
2-{6-[3-Amino-piperidin-1-yl]-3-(3-cyano-benzyl)-2,4-dioxo-3,4-dihydro-2H-pyrimidin-1-ylmethyl}-benzonitrile;
2-{6-[3-Amino-piperidin-1-yl]-3-(2-cyano-benzyl)-2,4-dioxo-3,4-dihydro-2H-pyrimidin-1-ylmethyl}-benzonitrile;
2-{6-[3-Amino-piperidin-1-yl]-3-(4-cyano-benzyl)-2,4-dioxo-3,4-dihydro-2H-pyrimidin-1-ylmethyl}-benzonitrile;
2-[6-(3-Amino-piperidin-1-yl)-3-(1H-benzoimidazol-2-ylmethyl)-2,4-dioxo-3,4-dihydro-2H-pyrimidin-1-ylmethyl]-benzonitrile;
2-{6-[3-Amino-piperidin-1-yl]-2,4-dioxo-3-(4-pyrazol-1-yl-benzyl)-3,4-dihydro-2H-pyrimidin-1-ylmethyl}-benzonitrile;
2-{6-[3-Amino-piperidin-1-yl]-2,4-dioxo-3-(3-pyrrol-1-yl-benzyl)-3,4-dihydro-2H-pyrimidin-1-ylmethyl}-benzonitrile;
6-[3-Amino-piperidin-1-yl]-3-(2-cyano-benzyl)-2,6-dioxo-3,6-dihydro-2H-pyrimidin-1-ylmethyl]-thiophene-3-carbonitrile;
3-{4-[3-Amino-piperidin-1-yl]-3-(2-cyano-benzyl)-2,6-dioxo-3,6-dihydro-2H-pyrimidin-1-ylmethyl}-benzoic acid methyl ester;
3-{4-[3-Amino-piperidin-1-yl]-3-(2-cyano-benzyl)-2,6-dioxo-3,6-dihydro-2H-pyrimidin-1-ylmethyl}-benzoic acid;
2-{6-[3(R)-Amino-piperidin-1-yl]-5-chloro-2,4-dioxo-3,4-dihydro-2H-pyrimidin-1-ylmethyl}-benzonitrile;
6-[3(R)-Amino-piperidin-1-yl]-1-(2,5-di-chloro-benzyl)-3-methyl-1H-pyrimidine-2,4-dione;
6-[3(R)-Amino-piperidin-1-yl]-1-(2-chloro-3,6-di-fluoro-benzyl)-3-methyl-1H-pyrimidine-2,4-dione;
(R)-2-((6-(3-amino-3-methylpiperidin-1-yl)-3-methyl-2,4-dioxo-3,4-dihydropyrimidin-1(2H)-yl)methyl)-4-fluorobenzonitrile; and
6-[3-Amino-piperidin-1-yl]-1,3-bis-(2-bromo-5-fluoro-benzyl)-1H-pyrimidine-2,4-dione.

The process of Claim 133, wherein the pyrimidin-dione is selected from the group consisting of:
{6-[3(R)-Amino-piperidin-1-yl]-3-methyl-2,4-dioxo-3,4-dihydro-2H-pyrimidin-1-ylmethyl}-benzonitrile;
2-{6-[3(R)-Amino-piperidin-1-yl]-3-ethyl-2,4-dioxo-3,4-dihydro-2H-pyrimidin-1-ylmethyl}-benzonitrile;
2-{6-[3(R)-Amino-piperidin-1-yl]-2,4-dioxo-3,4-dihydro-2H-pyrimidin-1-ylmethyl}-benzonitrile;
2-{6-[3(R)-Amino-piperidin-1-yl]-5-chloro-3-methyl-2,4-dioxo-3,4-dihydro-2H-pyrimidin-1-ylmethyl}-benzonitrile;
6-[3(R)-Amino-piperidin-1-yl]-1-(2-bromo-benzyl)-1H-pyrimidine-2,4-dione;
6-[3(R)-Amino-piperidin-1-yl]-1-(2-iodo-benzyl)-1H-pyrimidine-2,4-dione;
6-[3(R)-Amino-piperidin-1-yl]-1-(2-bromo-5-fluoro-benzyl)-3-methyl-1H-pyrimidine-2,4-dione;
6-[3(R)-Amino-piperidin-1-yl]-1-(2-chloro-5-fluoro-benzyl)-3-methyl-1H-pyrimidine-2,4-dione;
6-[3(R)-Amino-piperidin-1-yl]-1-(2-chloro-4-fluoro-benzyl)-3-methyl-1H-pyrimidine-2,4-dione;
6-[3(R)-Amino-piperidin-1-yl]-1-(2-bromo-benzyl)-3-methyl-1H-pyrimidine-2,4-dione;
2-{6-[3(R)-Amino-piperidin-1-yl]-3-(3-cyano-benzyl)-2,4-dioxo-3,4-dihydro-2H-pyrimidin-1-ylmethyl}-benzonitrile;
2-{6-[3(R)-Amino-piperidin-1-yl]-3-(2-cyano-benzyl)-2,4-dioxo-3,4-dihydro-2H-pyrimidin-1-ylmethyl}-benzonitrile;
2-{6-[3(R)-Amino-piperidin-1-yl]-3-(4-cyano-benzyl)-2,4-dioxo-3,4-dihydro-2H-pyrimidin-1-ylmethyl}-benzonitrile;
2-{6-[3(R)-Amino-piperidin-1-yl]-2,4-dioxo-3-(4-pyrazol-1-yl-benzyl)-3,4-dihydro-2H-pyrimidin-1-ylmethyl}-benzonitrile;
2-{6-[3(R)-Amino-piperidin-1-yl]-2,4-dioxo-3-(3-pyrrol-1-yl-benzyl)-3,4-dihydro-2H-pyrimidin-1-ylmethyl}-benzonitrile;
6-[3(R)-Amino-piperidin-1-yl]-3-(2-cyano-benzyl)-2,6-dioxo-3,6-dihydro-2H-pyrimidin-1-ylmethyl]-thiophene-3-carbonitrile;
3-{4-[3(R)-Amino-piperidin-1-yl]-3-(2-cyano-benzyl)-2,6-dioxo-3,6-dihydro-2H-pyrimidin-1-ylmethyl}-benzoic acid methyl ester;
{4-[3(R)-Amino-piperidin-1-yl]-3-(2-cyano-benzyl)-2,6-dioxo-3,6-dihydro-2H-pyrimidin-1-ylmethyl}-benzoic acid; and
6-[3(R)-Amino-piperidin-1-yl]-1,3-bis-(2-bromo-5-fluoro-benzyl)-1H-pyrimidine-2,4-dione.

In still another variation of each of the above embodiments and variations, the pyrimidin-dione is present as a mixture of stereoisomers. In yet another variation, the pyrimidin-dione comprises a single stereoisomer.

It is noted in regard to all of the embodiments, and any further embodiments, variations, or individual compounds described or claimed herein that all such embodiments, variations, and/or individual compounds are intended to encompass all pharmaceutical acceptable salt forms whether in the form of a single stereoisomer or mixture of stereoisomers unless it is specifically specified otherwise. Similarly, when one or more potentially chiral centers are present in any of the embodiments, variations, and/or individual compounds specified or claimed herein, both possible chiral centers are intended to be encompassed unless it is specifically specified otherwise.

A. Salts, Hydrates, and Prodrugs of DPP-IV Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine(tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as $(C_{1-4})$alkyl halides, e.g., methyl, ethyl, iso-propyl and tert-butyl chlorides, bromides and iodides; di $(C_{1-4})$alkyl sulfates, e.g., dimethyl, diethyl and diamyl sulfates; $(C_{10-18})$ alkyl halides, e.g., decyl, dodecyl, lauryl, myristyl and stearyl chlorides, bromides and iodides; and aryl $(C_{1-4})$alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, *Protecting Groups in Organic Synthesis*, $3^{rd}$ edition, John Wiley & Sons, Inc. 1999.

Compounds of the present invention may also be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid adsorption of the compound.

3. Indications for Use of DPP-IV Inhibitors

DPP-IV is believed to contribute to the pathology and/or symptomology of several different diseases such that reduction of the activity of DPP-IV in a subject through inhibition may be used to therapeutically address these disease states. Examples of various diseases that may be treated using the DPP-IV inhibitors of the present invention are described herein. It is noted that additional diseases beyond those disclosed herein may be later identified as the biological roles that DPP-IV plays in various pathways becomes more fully understood.

One set of indications that DPP-IV inhibitors of the present invention may be used to treat are those involving the prevention and treatment of diabetes and obesity, in particular type 2 diabetes mellitus, diabetic dislipidemia, conditions of impaired glucose tolerance (IGT), conditions of impaired fasting plasma glucose (IFG), metabolic acidosis, ketosis, appetite regulation and obesity.

DPP-IV inhibitors of the present invention may also be used as immunosuppressants (or cytokine release suppressant drugs) for the treatment of among other things: organ transplant rejection; autoimmune diseases such as inflammatory bowel disease, multiple sclerosis and rheumatoid arthritis; and the treatment of AIDS.

DPP-IV inhibitors of the present invention may also be used for treating various cancers including breast cancer, lung cancer and prostate cancer.

DPP-IV inhibitors of the present invention may also be used to treat dermatological diseases such as psoriasis, rheumatoid arthritis (RA) and lichen planus.

DPP-IV inhibitors of the present invention may also be used to treat infertility and amenorrhea.

DPP-IV inhibitors of the present invention may also be used to modulate cleavage of various cytokines (stimulating hematopoietic cells), growth factors and neuropeptides. For example, such conditions occur frequently in patients who are immunosuppressed, for example, as a consequence of chemotherapy and/or radiation therapy for cancer.

DPP-IV inhibitors of the present invention may also be used prevent or reduce cleavage of N-terminal Tyr-Ala from growth hormone-releasing factor. Accordingly, these inhibitors may be used in the treatment of short stature due to growth hormone deficiency (Dwarfism) and for promoting GH-dependent tissue growth or re-growth.

DPP-IV inhibitors of the present invention may also be used to address disease states associated with cleavage of neuropeptides and thus may be useful for the regulation or normalization of neurological disorders.

For oncology indications, DPP-IV inhibitors of the present invention may be used in conjunction with other agents to inhibit undesirable and uncontrolled cell proliferation. Examples of other anti-cell proliferation agents that may be used in conjunction with the DPP-IV inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA)), cishydroxyproline, d,l-3,4-dehydroproline, thiaproline, beta.-aminopropionitrile fumarate, 4-propyl-5-(4-pyridinyl)-2(3H)-oxazolone, methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

4. Compositions Comprising DPP-IV Inhibitors

A wide variety of compositions and administration methods may be used in conjunction with the DPP-IV inhibitors of the present invention. Such compositions may include, in addition to the DPP-IV inhibitors of the present invention, conventional pharmaceutical excipients, and other conventional, pharmaceutically inactive agents. Additionally, the compositions may include active agents in addition to the DPP-IV inhibitors of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising DPP-IV inhibitors of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraocularly, via local delivery (for example by catheter or stent), subcutaneously, intraadiposally, intraarticularly, or intrathecally. The compounds and/or compositions according to the invention may also be administered or coadministered in slow release dosage forms.

The DPP-IV inhibitors and compositions comprising them may be administered or coadministered in any conventional dosage form. Co-administration in the context of this invention is intended to mean the administration of more than one therapeutic agent, one of which includes a DPP-IV inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When DPP-IV inhibitors according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding DPP-IV inhibitors according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof.

A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more DPP-IV inhibitors according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a DPP-IV inhibitor of the present invention to reduce DPP-IV activity in vivo, thereby treating the disease state of the subject.

Dosage forms or compositions may optionally comprise one or more DPP-IV inhibitors according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium croscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more DPP-IV inhibitors, optionally 0.1-95%, and optionally 1-95%.

Salts, preferably sodium salts, of the DPP-IV inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, DPP-IV inhibitors according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, croscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The DPP-IV inhibitors of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising DPP-IV inhibitors of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

B. Injectables, Solutions and Emulsions

The present invention is also directed to compositions designed to administer the DPP-IV inhibitors of the present invention by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of a DPP-IV inhibitor in the parenteral formulation may be adjusted so that an injection administers a pharmaceutically effective amount sufficient to produce the desired pharmacological effect. The exact concentration of a DPP-IV inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the DPP-IV inhibitor to the treated tissue(s). The DPP-IV inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The DPP-IV inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The DPP-IV inhibitors of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a DPP-IV inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the DPP-IV inhibitor.

D. Topical Administration

The DPP-IV inhibitors of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irritations, sprays, suppositories, bandages, dermal patches or any other formulations suitable for topical administration.

The DPP-IV inhibitors may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The DPP-IV inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the DPP-IV inhibitor alone or in combination with other pharmaceutically acceptable excipients can also be administered.

E. Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

Oral Formulation

| | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

Intravenous Formulation

| | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| | |
|---|---|
| Compound of the Present Invention | 1% |
| Microcrystalline Cellulose | 73% |
| Stearic Acid | 25% |
| Colloidal Silica | 1%. |

5. Kits Comprising DPP-IV Inhibitors

The invention is also directed to kits and other articles of manufacture for treating diseases associated with DPP-IV. It is noted that diseases are intended to cover all conditions for which the DPP-IV possesses activity that contributes to the pathology and/or symptomology of the condition.

In one embodiment, a kit is provided that comprises a composition comprising at least one DPP-IV inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one DPP-IV inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

1. Preparation of DPP-IV Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999.

Compounds according to the present invention may be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i.v. (intravenous); Hz (Hertz);
MHz (megahertz); mol (moles);
mmol (millimoles); RT (ambient temperature);
min (minutes); h (hours);
mp (melting point); TLC (thin layer chromatography);
Tr (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimino); HOBT (1-hydroxybenzotriazole);
Et$_2$O (diethyl ether); EDCI (ethylcarbodiimino hydrochloride);
BOC (tert-butyloxycarbonyl); FMOC (9-fluorenylmethoxycarbonyl);
DCC (dicyclohexylcarbodiimino); CBZ (benzyloxycarbonyl);

Ac (acetyl); atm (atmosphere);

TMSE (2-(trimethylsilyl)ethyl); TMS (trimethylsilyl);

TIPS (triisopropylsilyl); TBS (t-butyldimethylsilyl);

DMAP (4-dimethylaminopyridine); Me (methyl);

OMe (methoxy); Et (ethyl);

Et (ethyl); tBu (tert-butyl);

HPLC (high pressure liquid chromatography);

BOP (bis(2-oxo-3-oxazolidinyl)phosphinic chloride);

TBAF (tetra-n-butylammonium fluoride);

mCPBA (meta-chloroperbenzoic acid.

All references to ether or $Et_2O$ are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR spectra were recorded on a Bruker Avance 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

2. Synthetic Schemes for DPP-IV Inhibitors of the Present Invention

DPP-IV inhibitors according to the present invention may be synthesized according to a variety of reaction schemes. Some illustrative schemes are provided herein in the examples. Other reaction schemes could be readily devised by those skilled in the art.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

By varying the $Q^1$ and $Q^2$, $R_1$, $R_2$, and $R_3$ groups, a wide variety of different DPP-IV inhibitors according to the present invention may be synthesized.

In each of the above reaction schemes, the various substituents may be selected from among the various substituents otherwise taught herein.

Descriptions of the syntheses of particular compounds according to the present invention based on the above reaction schemes are set forth herein.

3. Examples of DPP-IV Inhibitors

The present invention is further exemplified, but not limited by, the following examples that describe the synthesis of particular compounds according to the invention.

Experimental Methods

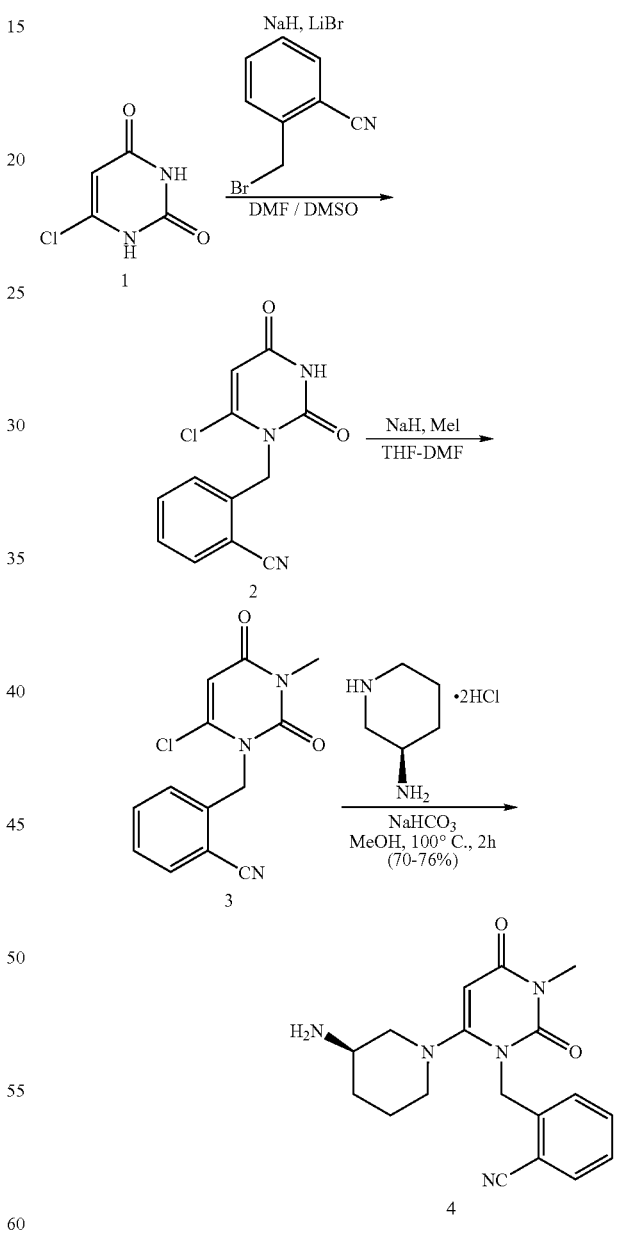

2-(6-Chloro-2,4-dioxo-3,4-dihydro-2H-pyrimidin-1-ylmethyl)-benzonitrile (2). To a solution of 6-chlorouracil (20 g, 122 mmol) in a mixture of DMF-DMSO (6:1, 600 mL) under nitrogen at 0° C., was added sodium hydride (60%, 5.5 g, 137 mmol) in portions. After 0.5 h, lithium bromide (8 g, 96 mmol) was added into the mixture and stirred for 15 min at 0°

C. A solution of α-Bromo-o-tolunitrile (25.1 g, 128 mmol) in DMF (30 mL) was added dropwise, and stirred at this temperature for 1 h, and then RT overnight. It will be understood that alkylation of the amine may be performed under standard conditions known in the art, including the use of a base such as NaH, LiH or the like in an organic solvent or mixture of solvents. The solvent may include DMSO, THF, DMF and the like, or mixtures thereof. In addition, additives may be used, including LiBr, LiI, NaI and the like. The mixture was evaporated and co-evaporated with water in vacuo to remove most of the DMF, and then poured into ice water (1 L). The precipitate was collected by filtration. The crude product was suspended in hot AcOEt-CHCl$_3$ and sonicated for 5 min, allowed to stand at 0° C. for 1 h, and then filtered to give a white solid of the title compound (19 g) in 54% yield. It will also be understood by those skilled in the art that purification may be accomplished using various methods known in the art, including washing with an aqueous/organic solvent or mixture of solvents, recrystallization and/or column chromatography. Non-limiting examples of organic solvents and solvent mixtures may include ethyl acetate, isopropyl acetate, acetone, THF and the like. $^1$H-NMR (400 MHz, DMSO): δ 11.82 (s, 1H), 7.87 (d, 1H, J=7.6 Hz), 7.71 (t, 1H, J=7.6 Hz), 7.51 (t, 1H, J=7.6 Hz), 7.37 (d, H, J=8 Hz), 6.06 (s, 1H), 5.31 (s, 2H). MS (ES) [m+H] calc'd for $C_{12}H_9ClN_3O_2$, 262.0; found 262.0.

2-(6-Chloro-3-methyl-2,4-dioxo-3,4-dihydro-2H-pyrimidin-1-ylmethyl)-benzonitrile (3). To a cold (0° C.) solution of benzylated 6-chlorouracil 2 (10 g, 38 mmol) in DMF-THF (1:1, 300 mL) under nitrogen, was added NaH (60%, 1.6 g, 39.9 mmol) in portions, followed by adding LiBr (2 g). The mixture was stirred at r.t for 20 min. After adding iodomethane (5.4 mL, 76 mmol), the flask was sealed and stirred at this temperature for 10 min, rt for 2 h, and 35° C. overnight, and then concentrated in vacuo. It will be understood that alkylation of the amine may be performed under standard conditions known in the art, including the use of a base such as NaH, LiH or the like in an organic solvent or mixture of solvents. The solvent may include DMSO, THF, DMF and the like, or mixtures thereof. In addition, additives may be used, including LiBr, LiI, NaI and the like. For example, the alkylation can be performed using methyliodide and KSCO$_3$ in acetone. The reaction may be performed at about 15-45° C., preferably at about 20-43° C., and more preferably at about 35-41° C. until the reaction is complete. The residue was dissolved in CHCl$_3$ and washed with water and brine, dried (Na$_2$SO$_4$), and filtered then concentrated in vacuo. The crude product was crystallized from THF-Hexanes to give 7.6 g (72%) of the title compound 3. It will also be understood by those skilled in the art that the benzonitrile may be purified in a variety of organic solvents or solvent mixtures. For example, the benzonitrile can be purified by adding a mixture of dichloromethane and heptane. Optionally, the benzonitrile may be further purified in an organic solvent or mixture of solvents such as dichloromethane, chloroform, acetonitrile, THF, ethyl acetate, isopropyl acetate and the like. Preferably, the product is purified and washed with ethyl acetate. $^1$H NMR (400 MHz, DMSO): δ 7.87 (d, 1H, J=7.6 Hz), 7.70 (t, 1H, J=7.6 Hz), 7.51 (t, 1H, J=7.6 Hz), 7.40 (d, 1H, J=8 Hz), 6.21 (s, 1H), 5.38 (s, 2H), 3.28 (s, 3H). MS (ES) [m+H] calc'd for $C_{13}H_{11}ClN_3O_2$, 276.1; found 276.1.

2-{6-[3(R)-Amino-piperidin-1-yl]-3-methyl-2,4-dioxo-3,4-dihydro-2H-pyrimidin-1-ylmethyl}-benzonitrile (4). 2-(6-Chloro-3-methyl-2,4-dioxo-3,4-dihydro-2-H-pyrimidin-1-ylmethyl)-benzonitrile (330 mg, 1.08 mmol), (R)-3-amino-piperidine dihydrochloride (246 mg, 1.4 mmol) and sodium bicarbonate (500 mg, 5.4 mmol) were stirred with 200 mg activated molecular sieves (4A) in dry MeOH (5 mL) at 100° C. for 2 h. The reaction was filtered through Celite, concentrated in vacuo, and then diluted with CHCl$_3$, and washed with water. The water phase was extracted with CHCl$_3$ and the combined organic phases were washed with water, dried (Na$_2$SO$_4$), and filtered. TFA (1 mL) was added into the solution which was then concentrated in vacuo. The residue was dissolved in a small amount of MeOH, and Et$_2$O was added to force precipitation. The mixture was allowed to stand at RT overnight. It will be understood by those skilled in the art that condensation with the amine or amine hydrochloride may be performed in a solvent or mixture of solvents with a base, such as potassium carbonate, sodium bicarbonate and the like, or mixtures thereof. The solvent may comprise both protic or aprotic solvents, or mixtures thereof. For example, the solvent may comprise a mixture of isopropyl alcohol and water. Further, the reaction may be heated to about 30-100° C., preferably about 35-55° C., and more preferably about 45-50° C. until the reaction is complete. Solvents were decanted, and the solid was washed with Et$_2$O two times to give 270 mg TFA salt of product 4 as off-white powder. It will also be understood that the product may be further purified by washing with an organic solvent or mixture of solvents. Non-limiting examples of solvent or solvent mixtures include isopropyl acetate, ethyl acetate, dichloromethane, heptane, and the like. Further, the product may optionally be purified by column chromatography. The TFA salt of 4 has $^1$H-NMR (400 MHz, CDCl$_3$-CD$_3$OD 10:1): δ 7.82 (d, 1H, J=7.6 Hz), 7.65 (t, 1H, J=7.6 Hz), 7.46 (t, 1H, J=7.6 Hz), 7.23 (d, 1H, J=8.0 Hz), 5.42 (s, 1H), 5.50-5.00 (ABq, 2H, J=41.6, 15.2 Hz), 3.30 (m, 2H), 3.16 (s, 3H), 2.91 (m, 1H), 2.76 (m, 2H), 1.93 (m, 1H), 1.79 (m, 1H), 1.51 (m, 2H). MS (ES) [m+H] calc'd for $C_{18}H_{22}N_5O_2$, 340.2; found, 340.2.

The benzonitrile product may be isolated as the free base if desired, but preferably, the product may be further converted to a corresponding acid addition salt. For example, the benzoic acid salt was formed by treating the benzonitrile product with benzoic acid to form 2-[6-(3-amino-piperidin-1-yl)-3-methyl-2,4-dioxo-3,4-dihydro-2H-pyrimidin-1-ylmethyl]-benzonitrile benzoate (4). Preparation and isolation of the benzoate salt was performed by conventional methods for the formation of acid addition salts. $^1$H-NMR (400 MHz, CDCl$_3$—CD$_3$OD 10:1): δ 7.82 (d, 1H, J=7.6 Hz), 7.65 (t, 1H, J=7.6 Hz), 7.46 (t, 1H, J=7.6 Hz), 7.23 (d, 1H, J=8.0 Hz), 5.42 (s, 1H), 5.50-5.00 (ABq, 2H, J=41.6, 15.2 Hz), 3.30 (m, 2H), 3.16 (s, 3H), 2.91 (m, 1H), 2.76 (m, 2H), 1.93 (m, 1H), 1.79 (m, 1H), 1.51 (m, 2H). MS (ES) [m+H] calc'd for $C_{18}H_{22}N_5O_2$, 340.2; found, 340.2.

Following the same procedure described above, HCl addition salt was prepared as follows. A free base form of 4 was isolated after the crude product was washed with water, dried over Na$_2$SO$_4$, filtered and concentrated. The free base product was then dissolved in THF. Alternatively, the free base could be dissolved in other solvents, such as dioxane, acetonitrile, ethyl acetate, dichloromethane, etc., or mixtures thereof. The solution was then stirred and 1.2 equivalents of 4M HCl in dioxane was added dropwise. After 10 min stirring, the suspended mixture was allowed to stand at rt for 1 h, and then filtered to give the solid HCl salt form of 4. $^1$H-NMR (400 MHz, DMSO-D6): δ 7.82 (d, 1H, J=7.6 Hz), 7.65 (t, 1H, J=7.6 Hz), 7.46 (t, 1H, J=7.6 Hz), 7.23 (d, 1H, J=8.0 Hz), 5.42 (s, 1H), 5.20, 5.08 (ABq, 2H, J=41.6, 15.2 Hz), 3.30 (m, 2H), 3.16 (s, 3H), 2.91 (m, 1H), 2.76 (m, 2H), 2.50 (bs, 2H), 1.93 (m, 1H), 1.79 (m, 1H), 1.51 (m, 2H). MS (ES) [m+H] calc'd for $C_{18}H_{22}N_5O_2$, 340.2; found, 340.2.

Further, the toluenesulfonate salt was prepared as follows. A 200 μL aliquot of a 0.03M stock solution of free base was dissolved in dichloromethane and concentrated under a slow stream of nitrogen. The resulting free base was dissolved in 150 μL of solvent (e.g., acetic acid, acetone, ethanol, THF or dichlormethane) and the solution shaken for 10 minutes. The shaken solution was then charged with 50 μL of a 0.126M solution of toluenesulfonic acid (1.05 eq.) in dioxane. The solution was shaken for 3 hours, followed by removal of the solvents under a stream of nitrogen to provide the toluenesulfonate salt.

The toluenesulfonate salt was also prepared by dissolving 2 g of the free base in 10 volumes of acetonitrile and heating the solution to 75° C. for 10 minutes. Then p-toluenesulfonic acid (1.05 equivalents) was added and the solution held at 75° C. for 5 minutes. The temperature was ramped down (at about 25° C./hr) and stirred at room temperature overnight. The product (2.64 g) was dried in a vacuum oven at 50° C. and 698.5 mm Hg with a nitrogen sweep for 18 hours.

In each of the above steps, the isolation and/or purification steps of the intermediate compounds may be avoided if the intermediates from the reaction mixture are obtained as relatively pure compounds and the by-products or impurities of the reaction mixture do not interfere with the subsequent reaction steps. Where feasible, one or more isolation steps may be eliminated to provide shorter processing times, and the elimination of further processing may also afford higher overall reaction yields.

Compound 5

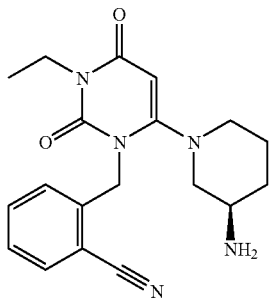

2-{6-[3(R)-Amino-piperidin-1-yl]-3-ethyl-2,4-dioxo-3,4-dihydro-2H-pyrimidin-1-ylmethyl}-benzonitrile TFA salt (5). The title compound, 5, was prepared from sample 2 using the procedures described in the preparation of samples 3 and 4, except that ethyl bromide was used in place of iodomethane. $^1$H-NMR (400 MHz, CDCl$_3$-CD$_3$OD 10:1): δ 7.66 (d, J=7.8 Hz, 1H), 7.59 (td, J=7.8, 1.4 Hz, 1H), 7.40 (t, J=7.6 Hz, 1H), 7.26 (d, J=7.6 Hz, 1H), 5.41 (s, 1H), 5.13-5.23 (ABq, 2H, J=41.6, 15.2 Hz), 3.91 (q, J=7.1 Hz, 2H), 3.37 (m, 2H), 2.87-2.98 (m, 2H), 2.70 (m, 1H), 2.12 (m, 1H), 1.88 (m, 1H), 1.67 (m, 2H), 1.15 (t, J=6.9 Hz, 3H). MS (ES) [m+H] calc'd for C$_{19}$H$_{24}$N$_5$O$_2$, 354.2; found, 354.2.

Compound 6

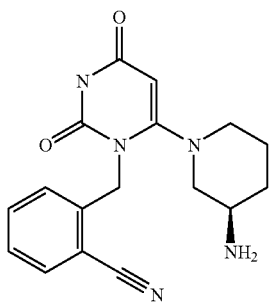

2-{6-[3(R)-Amino-piperidin-1-yl]-2,4-dioxo-3,4-dihydro-2H-pyrimidin-1-ylmethyl}-benzonitrile (6). The title compound 6 was prepared from compound 2 by the procedure used in preparation of compound 4. $^1$H-NMR (400 MHz, CDCl$_3$-CD$_3$OD 10:1): δ 7.65 (d, J=7.5 Hz, 1H), 7.58 (t, J=7.8 Hz, 1H), 7.39 (t, J=7.5 Hz, 1H), 7.27 (d, J=7.8 Hz, 1H), 5.32 (s, 1H), 5.13-5.13 (ABq, 2H, J=30.0, 15.0 Hz), 3.39 (m, 2H), 2.95 (m, 2H), 2.69 (m, 1H), 2.12 (m, 1H), 1.85 (m, 1H), 1.64 (m, 2H). MS (ES) [m+H] calc'd for C$_{17}$H$_{20}$N$_5$O$_2$, 326.2; found, 326.2.

Compound 7

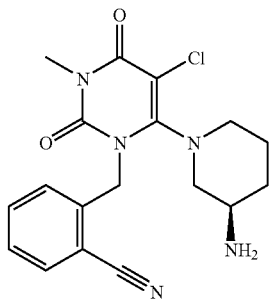

2-{6-[3(R)-Amino-piperidin-1-yl]-5-chloro-3-methyl-2,4-dioxo-3,4-dihydro-2H-pyrimidin-1-ylmethyl}-benzonitrile (7). Compound 4 (40 mg, 0.1 mmol) in CHCl$_3$ (2 mL) was treated with SOCl$_2$ (200 μL) at 100° C. for 30 min, concentrated, and then purified by LC-MS to give the title compound 7. $^1$H-NMR (400 MHz, CDCl$_3$-CD$_3$OD 10:1): δ 7.73 (d, J=7.6 Hz, 1H), 7.64 (t, J=7.6 Hz, 1H), 7.45 (t, J=7.6 Hz, 1H), 7.14 (d, J=8.1 Hz, 1H), 5.32-5.42 (m, 2H), 3.43 (s, 3H), 3.33-3.40 (m, 2H), 3.17 (m, 2H), 2.87 (s, 1H), 2.08 (m, 1H), 1.70 (m, 1H), 1.32-1.43 (m, 2H). MS (ES) [m+H] calc'd for C$_{18}$H$_{21}$ClN$_5$O$_2$, 374.1; found, 374.1.

Compound 8

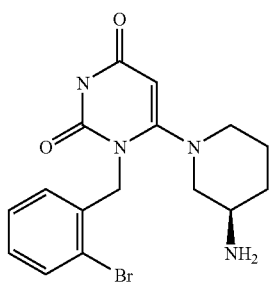

6-[3(R)-Amino-piperidin-1-yl]-1-(2-bromo-benzyl)-1H-pyrimidine-2,4-dione (8). The title compound was prepared in two steps. The first step was accomplished using the procedure for the preparation of compound 2, except that 2-bromobenzylbromide was used in the place of α-Bromo-o-tolunitrile. The crude product was then converted to the title compound by the method used in the preparation of compound 4. $^1$H-NMR (400 MHz, CDCl$_3$-CD$_3$OD 10:1): δ 7.52 (d, J=8.1 Hz, 1H), 7.24 (t, J=7.8 Hz, 1H), 7.10 (t, J=7.8 Hz, 1H), 6.89 (d, J=7.579 Hz, 1H), 5.27 (s, 1H), 4.92-5.04 (ABq, J=34.1, 15.0 Hz, 2H), 3.27 (bd, J=10.4 Hz, 1H), 3.09-3.18 (m, 1H), 2.89 (m, 1H), 2.70 (t, J=10.9 Hz, 1H), 2.48 (t, J=12.0 Hz, 1H), 2.03 (m, 1H), 1.60-1.71 (m, 1H), 1.42-1.53 (m, 2H). MS (ES) [m+H] calc'd for C$_{16}$H$_{20}$BrN$_4$O$_2$, 379.1; found, 379.1.

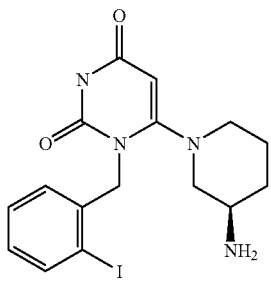

Compound 9

6-[3(R)-Amino-piperidin-1-yl]-1-(2-iodo-benzyl)-1H-pyrimidine-2,4-dione (9). The title compound was prepared by the procedure described in the preparation of compound 8, except that 2-iodobenzyl chloride was used as the benzylating reagent. $^1$H-NMR (400 MHz, CDCl$_3$-CD$_3$OD 10:1): δ 7.76 (d, J=7.6 Hz, 1H), 7.21 (t, J=7.3 Hz, 1H), 6.89 (t, J=7.2 Hz, 1H), 6.79 (d, J=7.3 Hz, 1H), 5.26 (s, 1H), 4.79-4.92 (ABq, J=34.1, 6.7.0 Hz, 2H), 3.27 (m, 1H), 3.13 (s, 1H), 2.85 (d, J=11.6 Hz, 1H), 2.70 (m, 1H), 2.41 (m, 1H), 2.02 (m, 1H), 1.60 (m, 1H), 1.45 (m, 2H). MS (ES) [m+H] calc'd for C$_{16}$H$_{20}$IN$_4$O$_2$, 427.1; found, 427.1.

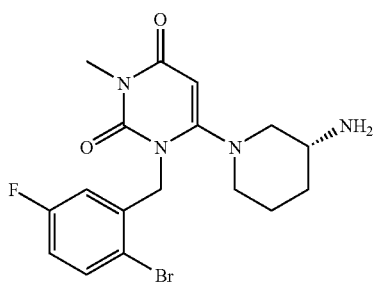

Compound 10

6-[3(R)-Amino-piperidin-1-yl]-1-(2-bromo-5-fluoro-benzyl)-3-methyl-1H-pyrimidine-2,4-dione (10). To a solution of 6-chlorouracil (220 mg, 1.5 mmol) in a mixture of dry DMF-DMSO (6:1, 5 mL) under nitrogen at 0° C., was added sodium hydride (60%, 61 mg, 1.8 mmol) in portions. After 0.5 h, lithium bromide (83 mg, 1 mmol) was added and the mixture was stirred for 15 min at 0° C. A solution of 2-bromo-5-fluoro-benzyl bromide (497 mg, 1.8 mmol) in DMF (30 mL) was added dropwise, and stirred at this temperature for 1 h, and then RT overnight. The mixture was evaporated and co-evaporated with water in vacuo to remove most of the DMF, and then poured into ice-water. The precipitate was collected by filtration, and then suspended in cold MeOH and filtered. The solution was concentrated to give the crude monobenzylated product.

The crude product was treated with NaH and MeI using the procedure described in the preparation of compound 3, followed by the procedure used in the preparation of compound 4 to give the title compound. $^1$H-NMR (400 MHz, CDCl$_3$-CD$_3$OD 10:1) δ 7.46 (dd, J=8.7, 5.2 Hz, 1H), 6.82 (td, J=8.3, 2.9 Hz, 1H), 6.59 (dd, J=9.1, 3.0 Hz, 1H), 5.28 (s, 1H), 4.99-5.06 (ABq, J=41.7, 16.7 Hz, 2H), 3.28 (m, 1H), 3.23 (s, 3H), 3.13-3.21 (m, 1H), 2.86 (bd, J=12.6 Hz, 1H), 2.71 (t, J=10.5 Hz, 1H), 2.47 (t, J=11.0 Hz, 1H), 2.00-2.08 (m, 1H), 1.65-1.74 (m, 1H), 1.42-1.53 (m, 2H). MS (ES) [m+H] calc'd for C$_{17}$H$_{21}$BrFN$_4$O$_2$, 411.1; found, 411.1.

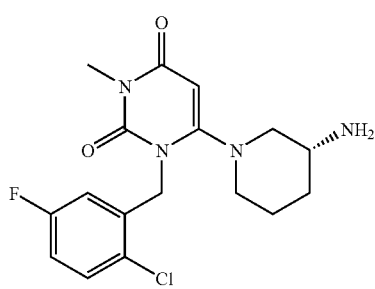

Compound 11

6-[3(R)-Amino-piperidin-1-yl]-1-(2-chloro-5-fluoro-benzyl)-3-methyl-1H-pyrimidine-2,4-dione (11). The title compound was prepared from compound 1 using the same procedures as the preparation of compound 10, except that 2-chloro-5-fluoro-benzyl bromide was used in the place of 2-bromo-5-fluoro-benzyl bromide. $^1$H-NMR (400 MHz, CDCl$_3$-CD$_3$OD 10:1): δ 7.34-7.40 (dd, J=8.5, 5.1 Hz, 1H), 6.97 (td, J=8.3, 2.9 Hz, 1H), 6.72 (dd, J=9.0, 2.9 Hz, 1H), 5.41 (s, 1H), 5.11-5.19 (ABq, J=41.7, 16.7 Hz, 2H), 3.37 (s, 1H), 3.32 (s, 3H), 3.23-3.30 (m, 1H), 2.96 (d, J=12.1 Hz, 1H), 2.81 (t, J=10.2 Hz, 1H), 2.59 (t, J=11.1 Hz, 1H), 2.13 (d, J=10.4 Hz, 1H), 1.76-1.86 (m, 1H), 1.52-1.63 (m, 2H). MS (ES) [m+H] calc'd for C$_{17}$H$_{21}$ClFN$_4$O$_2$, 367.1; found 367.1.

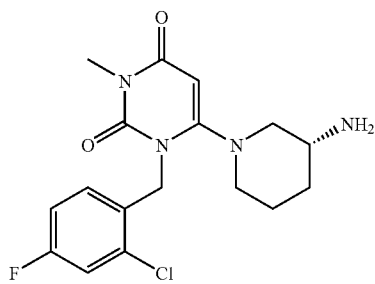

Compound 12

6-[3(R)-Amino-piperidin-1-yl]-1-(2-chloro-4-fluoro-benzyl)-3-methyl-1H-pyrimidine-2,4-dione (12). The title compound was prepared from compound 1 using the same procedures as described the preparation of compound 10, except that 2-chloro-4-fluoro-benzyl bromide was used in the place of 2-bromo-5-fluoro-benzyl bromide. $^1$H-NMR (400 MHz, CDCl$_3$-CD$_3$OD 10:1) δ 7.15 (dd, J=8.211, 2.400 Hz, 1H), 6.95-7.06 (m, 2H), 5.40 (s, 1H), 5.09-5.18 (ABq, J=37.7, 15.9 Hz, 2H), 3.33-3.39 (m, 1H), 3.30 (s, 3H), 3.23-3.29 (m, 1H), 2.98 (bd, J=12.9 Hz, 1H), 2.79 (t, J=10.4 Hz, 1H), 2.55-2.66 (t, J=11.2 Hz, 1H), 2.13 (m, 1H), 1.78-1.88 (m, 1H), 1.55-1.65 (m, 2H). MS (ES) [m+H] calc'd for C$_{17}$H$_{21}$ClFN$_4$O$_2$, 367.1; found 367.1.

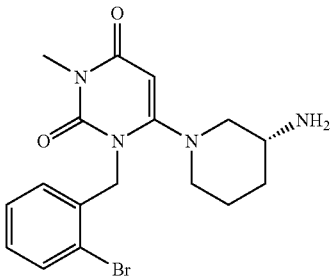

Compound 13

6-[3(R)-Amino-piperidin-1-yl]-1-(2-bromo-benzyl)-3-methyl-1H-pyrimidine-2,4-dione (13). The title compound was prepared from compound 1 used the procedures described in the synthesis of compound 10, except that 2-bromo benzyl bromide was used in the place of 2-bromo-5-fluoro-benzyl bromide. $^1$H-NMR (400 MHz, CDCl$_3$-CD$_3$OD 10:1): δ 7.45 (d, J=7.8 Hz, 1H), 7.16 (t, J=7.5 Hz, 1H), 7.03 (t, J=7.2 Hz, 1H), 6.80 (d, J=7.3 Hz, 1H), 5.28 (s, 1H), 4.93-5.05 (ABq, 2H, J=36.4, 16.4 Hz), 3.22 (m, 1H), 3.19 (m, 3H), 3.09 (m, 1H), 2.84 (d, J=12.6 Hz, 1H), 2.63 (t, J=10.5 Hz, 1H), 2.42 (t, J=10.9 Hz, 1H), 1.97 (d, J=11.1 Hz, 1H), 1.58-1.69 (m, 1H), 1.38-1.48 (m, 2H). MS (ES) [m+H] calc'd for C$_{17}$H$_{22}$BrN$_4$O$_2$, 393.1; found, 393.1.

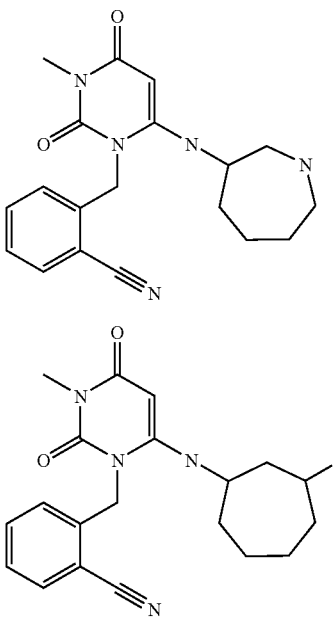

Compound 14

Compound 15

2-{6-[Azepan-3(±)-ylamino]-3-methyl-2,4-dioxo-3,4-dihydro-2H-pyrimidin-1-ylmethyl}-benzonitrile (14) and 2-{6-[3(±)-Amino-azepan-1-yl]-3-methyl-2,4-dioxo-3,4-dihydro-2H-pyrimidin-1-ylmethyl}-benzonitrile (15). Title compounds 14 and 15 were prepared from compound 3 (70 mg, 0.27 mmol) and azepan-3-ylamine (70 mg, 0.61 mg) using the procedure for the preparation of compound 4. Both compounds were purified by LC-MS.

14: $^1$H-NMR (400 MHz, CDCl$_3$-CD$_3$OD 10:1) δ 7.77 (d, J=7.8 Hz, 1H), 7.66 (t, J=7.6 Hz, 1H), 7.47 (t, J=8.0 Hz, 1H), 7.36 (d, J=8.1 Hz, 1H), 5.54 (s, 1H), 5.49 (s, 1H), 5.27-5.36 (ABq, J=26.0, 16.4 Hz, 2H), 3.50 (m, 2H), 3.37 (s, 2H), 3.26 (s, 3H), 3.12 (m, 1H), 3.04 (m, 1H), 2.07 (m, 1H), 1.86 (m, 1H), 1.60-1.71 (m, 3H). MS (ES) [m+H] calc'd for C$_{19}$H$_{24}$N$_5$O$_2$, 354.2; found, 354.2.

15: $^1$H-NMR (400 MHz, CDCl$_3$-CD$_3$OD 10:1) δ 7.77 (d, J=8.1 Hz, 1H), 7.63 (t, J=7.6 Hz, 1H), 7.46 (t, J=8.0 Hz, 1H), 7.19 (d, J=7.6 Hz, 1H), 5.48 (s, 1H), 5.44-5.52 (ABq, J=61.9, 18.4 Hz, 2H), 3.80 (s, 1H), 3.58-3.50 (m, 1H), 3.39-3.39 (m, 1H), 3.26 (s, 3H), 3.13 (m, 1H), 2.89 (t, J=12.4 Hz, 1H), 2.04 (m, 1H), 1.93 (m, 1H), 1.86 (m, 2H), 1.59-1.70 (m, 2H). MS (ES) [m+H] calc'd for C$_{19}$H$_{24}$N$_5$O$_2$, 354.2; found, 354.2.

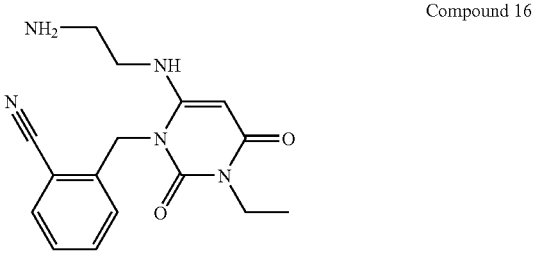

Compound 16

2-[6-(2-Amino-ethylamino)-3-ethyl-2,4-dioxo-3,4-dihydro-2H-pyrimidin-1-ylmethyl]-benzonitrile (16). Compound 2 (150 mg, 0.57 mmol) in THF-DMSO (6:1, 4 mL) was treated with 60% NaH (26 mg, 0.65 mmol), followed by adding ethyl bromide (300 uL). In a sealed tube, ~20% crude product in dry MeOH (3 mL) was treated NaHCO$_3$ and ethane-1,2-diamine (200 μL) at 120° C. for 2 h, and purified by LC-MS to give the title compound 16. $^1$H-NMR (400 MHz, CDCl$_3$-CD$_3$OD 10:1) δ 7.70 (d, J=7.8 Hz, 1H), 7.58 (t, J=7.7 Hz, 1H), 7.40 (t, J=7.4 Hz, 1H), 7.12 (d, J=8.1 Hz, 1H), 5.37 (s, 2H), 3.95 (q, J=6.8 Hz, 2H), 3.45 (t, J=5.9 Hz, 2H), 3.11 (t, J=6.1 Hz, 2H), 1.19 (t, J=6.8 Hz, 3H). MS (ES) [m+H] calc'd for C$_{16}$H$_{20}$N$_5$O$_2$, 314.2; found 314.2.

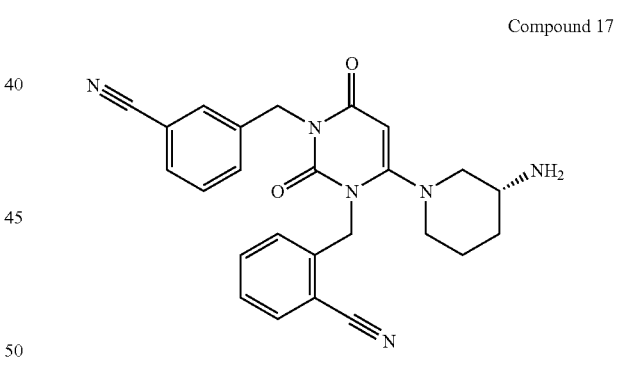

Compound 17

2-{6-[3(R)-Amino-piperidin-1-yl]-3-(3-cyano-benzyl)-2,4-dioxo-3,4-dihydro-2H-pyrimidin-1-ylmethyl}-benzonitrile (17). Compound 2 (65 mg, 0.25 mmol) in DME-DMF (2:1, 2.5 mL) was treated with 60% NaH (15 mg, 0.38 mmol) at 0° C. for 20 min, and then LiBr (25 mg) was added. 10 min later, m-cyano-benzyl bromide (55 mg, 0.28 mg) was added, and the mixture was stirred at RT for 5 h, and concentrated. The crude residue was dissolved in MeOH (3 mL). (R)-3-Amino-piperidine dihydrochloride (52 mg, 0.3 mmol) and sodium bicarbonate (100 mg) were added. The mixture was heated in a sealed tube at 120° C. for 2 h, and then filtered and concentrated. LC-MS purification gave the title compound 17 in 84% yield. $^1$H-NMR (400 MHz, CDCl$_3$-CD$_3$OD 10:1) δ 7.67 (d, J=7.8 Hz, 1H), 7.52-7.62 (m, 4H), 7.35-7.46 (m, 2H), 7.27 (d, J=7.8 Hz, 1H), 5.43 (s, 1H), 5.15-5.31 (ABq, J=40.9, 13.7 Hz, 2H), 5.04 (s, 2H), 3.40 (s, 1H), 3.40 (m 1H), 3.03 (m, 1H), 2.91 (m, 1H), 2.76 (s, 1H), 2.13 (s, 1H), 1.92 (m, 1H), 1.63-1.74 (m, 2H). MS (ES) [m+H] calc'd for $C_{25}H_{25}N_6O_2$, 441.2; found 441.2.

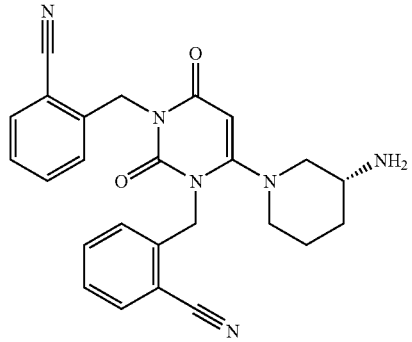

Compound 18

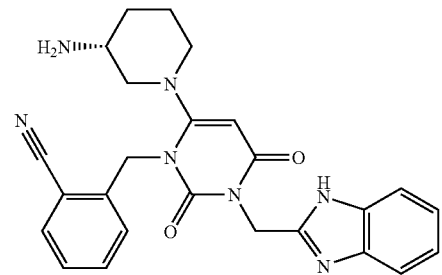

Compound 20

2-{6-[3(R)-Amino-piperidin-1-yl]-3-(2-cyano-benzyl)-2,4-dioxo-3,4-dihydro-2H-pyrimidin-1-ylmethyl}-benzonitrile (18). Title compound 18 was prepared by the methods used in the preparation of compound 17, except that α-bromo-o-tolunitrile was used in the place of m-cyano-benzyl bromide. $^1$H-NMR (400 MHz, CDCl$_3$-CD$_3$OD 10:1) δ 7.64 (d, J=6.8 Hz, 1H), 7.60 (d, J=7.8 Hz, 1H), 7.55 (t, J=7.8 Hz, 2H), 7.44 (t, J=7.6 Hz, 1H), 7.38 (t, J=7.5 Hz, 1H), 7.31 (t, J=7.6 Hz, 1H), 7.27 (d, J=7.8 Hz, 1H), 7.12 (d, J=7.8 Hz, 1H), 5.45 (s, 1H), 5.15-5.32 (m, 4H), 3.36-3.47 (m, 2H), 2.98 (m, 2H), 2.10 (m, 1H), 1.91 (m, 1H), 1.68 (m, 2H). MS (ES) [m+H] calc'd for $C_{25}H_{25}N_6O_2$, 441.2; found 441.2.

2-[6-(3-Amino-piperidin-1-yl)-3-(1H-benzoimidazol-2-ylmethyl)-2,4-dioxo-3,4-dihydro-2H-pyrimidin-1-ylmethyl]-benzonitrile (20). Title compound 20 was prepared by the methods used in the preparation of compound 17, except that 2-chloromethyl benzimidazole was used in the place of m-cyano-benzyl bromide. $^1$H-NMR (400 MHz, CDCl$_3$-CD$_3$OD 10:1) δ 7.67 (d, J=3.0 Hz, 1H), 7.65-7.56 (m, 2H), 7.47 (d, J=3.3 Hz, 2H), 7.46 (d, J=3.3 Hz, 1H), 7.37-7.40 (m, 2H), 5.52 (s, 3H), 5.23 (s, 2H), 3.51 (d, J=9.6 Hz, 1H), 3.36 (m, 1H), 2.87-2.92 (m, 2H), 2.64-2.72 (m, 1H), 2.09 (m, 1H), 1.76 (m, 1H), 1.52-1.64 (m, 2H). MS (ES) [m+H] calc'd for $C_{25}H_{26}N_7O_2$, 456.2; found 456.2.

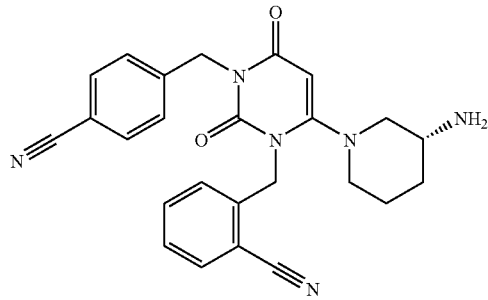

Compound 19

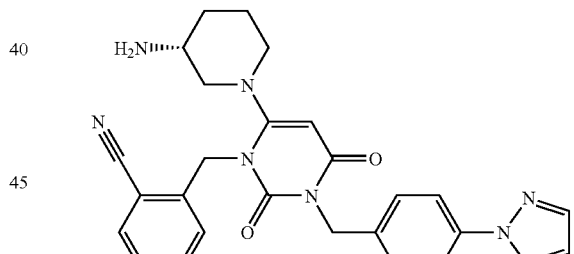

Compound 21

2-{6-[3(R)-Amino-piperidin-1-yl]-3-(4-cyano-benzyl)-2,4-dioxo-3,4-dihydro-2H-pyrimidin-1-ylmethyl}-benzonitrile (19). Title compound 19 was prepared by the methods used in the preparation of compound 17, except that p-cyano-benzyl bromide was used in the place of m-cyano-benzyl bromide. $^1$H-NMR (400 MHz, CDCl$_3$-CD$_3$OD 10:1) δ 7.70 (d, J=7.8 Hz, 1H), 7.56-7.63 (m, 3H), 7.46 (m, 3H), 7.29 (d, J=7.8 Hz, 1H), 5.47 (s, 1H), 5.16-5.36 (ABq, J=51.1, 14.7 Hz, 2H), 5.11 (s, 2H), 3.36-3.47 (m, 2H), 2.90-3.07 (m, 2H), 2.79 (s, 1H), 2.15 (s, 1H), 1.95 (s, 1H), 1.73 (s, 2H). MS (ES) [m+H] calc'd for $C_{25}H_{25}N_6O_2$, 441.2; found 441.2.

2-{6-[3(R)-Amino-piperidin-1-yl]-2,4-dioxo-3-(4-pyrazol-1-yl-benzyl)-3,4-dihydro-2H-pyrimidin-1-ylmethyl}-benzonitrile (21). Title compound 21 was prepared by the methods used in the preparation of compound 17, except that 1-(4-bromomethyl-phenyl)-1H-pyrazole was used in the place of m-cyano-benzyl bromide. $^1$H-NMR (400 MHz, CDCl$_3$-CD$_3$OD 10:1) δ 7.90 (d, J=2.5 Hz, 1H), 7.71 (d, J=1.8 Hz, 1H), 7.65 (d, J=7.6 Hz, 1H), 7.51-7.58 (m, 3H), 7.43-7.37 (m, 3H), 7.22 (d, J=7.8 Hz, 1H), 6.47 (t, J=2.1 Hz, 1H), 5.43 (s, 1H), 5.14-5.30 (ABq, J=41.2, 16.4 Hz, 2H), 5.05 (s, 2H), 3.32-3.40 (m, 2H), 2.96 (m, 1H), 2.89 (m, 1H), 2.70 (m, 1H), 2.10 (m, 1H), 1.88 (m, 1H), 1.66 (s, 2H). MS (ES) [m+H] calc'd for $C_{27}H_{28}N_7O_2$, 482.2; found 482.2.

Compound 22

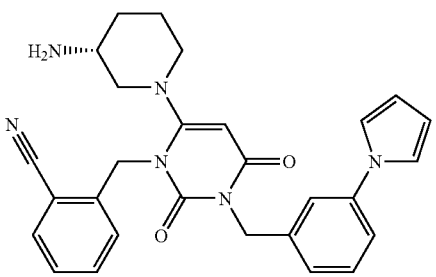

2-{6-[3(R)-Amino-piperidin-1-yl]-2,4-dioxo-3-(3-pyrrol-1-yl-benzyl)-3,4-dihydro-2H-pyrimidin-1-ylmethyl}-benzonitrile (22). Title compound 22 was prepared by the methods used in the preparation of compound 17, except that 1-(3-bromomethyl-phenyl)-1H-pyrrole was used in the place of m-cyano-benzyl bromide. $^1$H-NMR (400 MHz, CDCl$_3$-CD$_3$OD 10:1) δ 7.59 (d, J=7.3 Hz, 1H), 7.48 (t, J=7.7 Hz, 1H), 7.24-7.36 (m, 4H), 7.21 (t, J=7.6 Hz, 2H), 7.02 (t, J=2.1 Hz, 2H), 6.32 (t, J=2.0 Hz, 2H), 5.42 (s, 1H), 5.11-5.20 (ABq, J=44.7, 15.9 Hz, 2H), 5.06 (s, 2H), 3.36 (m, 2H), 2.98 (m, 1H), 2.89 (m, 1H), 2.70 (m, 1H), 2.10 (m, 1H), 1.88 (m, 1H), 1.73-1.58 (m, 2H). MS (ES) [m+H] calc'd for C$_{28}$H$_{29}$N$_6$O$_2$, 481.2; found 481.2.

Compound 23

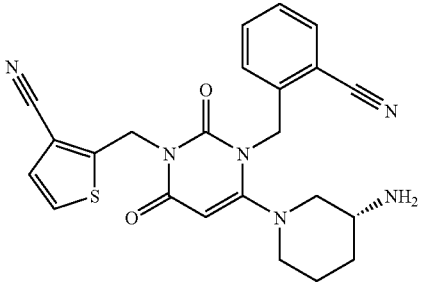

6-[3(R)-Amino-piperidin-1-yl]-3-(2-cyano-benzyl)-2,6-dioxo-3,6-dihydro-2H-pyrimidin-1-ylmethyl]-thiophene-3-carbonitrile (23). Title compound 23 was prepared by the methods used in the preparation of compound 17, except that 2-bromomethyl-thiophene-3-carbonitrile was used in the place of m-cyano-benzyl bromide. $^1$H-NMR (400 MHz, CDCl$_3$-CD$_3$OD 10:1) δ 7.65 (d, J=7.6 Hz, 1H), 7.57 (t, J=7.8 Hz, 1H), 7.40 (t, J=7.7 Hz, 1H), 7.29 (d, J=7.8 Hz, 1H), 7.25 (dd, J=5.3, 1.3 Hz, 1H), 7.11 (dd, J=5.3, 1.0 Hz, 1H), 5.45 (s, 1H), 5.35 (s, 2H), 5.15-5.33 (ABq, J=45.0, 15.5 Hz, 2H), 3.38 (bd, J=10.1 Hz, 2H), 2.98 (m, 2H), 2.72 (s, 1H), 2.12 (d, J=7.3 Hz, 1H), 1.83-1.93 (m, 1H), 1.61-1.72 (m, 2H). MS (ES) [m+H] calc'd for C$_{23}$H$_{23}$N$_6$O$_4$, 447.1; found 447.1.

Compound 24

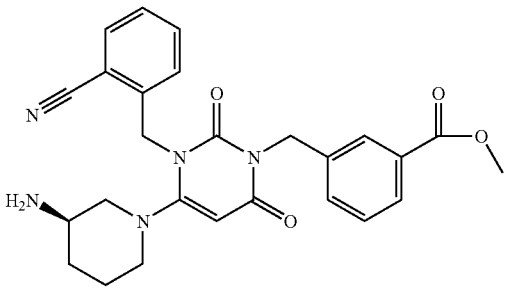

3-{4-[3(R)-Amino-piperidin-1-yl]-3-(2-cyano-benzyl)-2,6-dioxo-3,6-dihydro-2H-pyrimidin-1-ylmethyl}-benzoic acid methyl ester (24). Title compound 24 was prepared by the methods used in the preparation of compound 17, except that 3-bromomethyl-benzoic acid methyl ester was used in the place of m-cyano-benzyl bromide. $^1$H-NMR (400 MHz, CDCl$_3$-CD$_3$OD 10:1) δ 7.99 (s, 1H), 7.91 (d, J=7.8 Hz, 1H), 7.65 (d, J=7.6 Hz, 1H), 7.56 (d, J=7.9 Hz, 1H), 7.52 (d, J=7.6 Hz, 1H), 7.39 (t, J=7.6 Hz, 1H), 7.34 (t, J=7.6 Hz, 1H), 7.23 (d, J=8.1 Hz, 1H), 5.44 (s, 1H), 5.12-5.31 (ABq, J=43.7, 15.9 Hz, 2H), 5.08 (s, 2H), 3.90 (s, 3H), 3.31-3.39 (m, 2H), 2.98 (d, J=11.9 Hz, 1H), 2.87 (m, 1H), 2.71 (m, 1H), 2.11 (m, 1H), 1.89 (m, 1H), 1.73-1.59 (m, 2H). MS (ES) [m+H] calc'd for C$_{26}$H$_{28}$N$_5$O$_4$, 474.2; found 474.2.

Compound 25

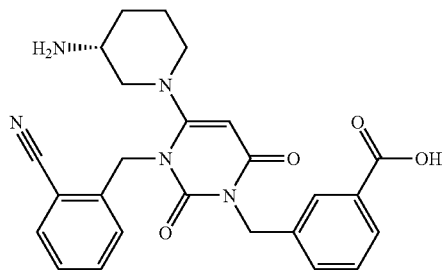

3-{4-[3(R)-Amino-piperidin-1-yl]-3-(2-cyano-benzyl)-2,6-dioxo-3,6-dihydro-2H-pyrimidin-1-ylmethyl}-benzoic acid (25). A crude mixture of compound 24 (~50 mg) was treated with LiOH in THF-water (10:1) to give the title compound 25. $^1$H-NMR (400 MHz, CDCl$_3$-CD$_3$OD 10:1) δ 7.90 (s, 1H), 7.86 (d, J=7.6 Hz, 1H), 7.60 (d, J=7.6 Hz, 1H), 7.50 (t, J=8.2 Hz, 1H), 7.45 (d, J=7.3 Hz, 1H), 7.26-7.36 (m, 2H), 7.17 (d, J=8.1 Hz, 1H), 5.39 (s, 1H), 5.10-5.25 (ABq, J=36.9, 15.5 Hz, 2H), 5.03 (s, 2H), 3.31 (m, 2H), 2.95 (m, 1H), 2.81 (m, 1H), 2.64 (m, 1H), 2.07 (m, 1H), 1.82 (m, 1H), 1.51-1.68 (m, 2H). MS (ES) [m+H] calc'd for C$_{25}$H$_{26}$N$_5$O$_4$, 460.2; found 460.2.

Compound 26

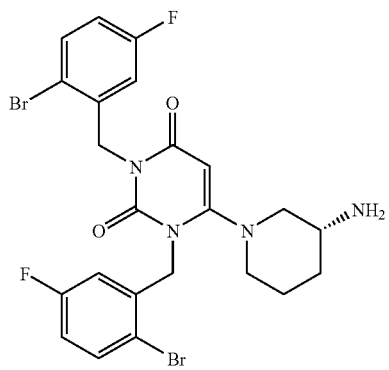

6-[3(R)-Amino-piperidin-1-yl]-1,3-bis-(2-bromo-5-fluoro-benzyl)-1H-pyrimidine-2,4-dione (26). The title compound was prepared from 1 by di-benzylation, using the procedure for the preparation of 2, except that 2-bromo-5-fluoro-benzyl bromide was used in the place of α-bromo-o-tolunitrile, followed by treatment with 3-(R)-amino-piperidine under the conditions described in the preparation of compound 4. $^1$H-NMR (400 MHz, CDCl$_3$-CD$_3$OD 10:1) δ

7.42 (dd, J=8.6, 5.3 Hz, 2H), 7.11-7.08 (dd, J=9.1, 2.2 Hz, 1H), 7.06 (dd, J=9.3, 2.8 Hz, 1H), 6.78-6.84 (m, 2H), 5.71 (s, 1H), 5.29 (s, 4H), 4.22 (d, J=11.1 Hz, 1H), 3.82 (d, J=13.4 Hz, 1H), 3.07-3.24 (m, 3H), 2.06 (m, 1H), 1.75-1.83 (m, 1H), 1.63-1.72 (m, 1H), 1.50-1.59 (m, 1H). MS (ES) [m+H] calc'd for $C_{23}H_{23}Br_2F_2N_3O_2$, 583.01; found 583.01.

Compound 27

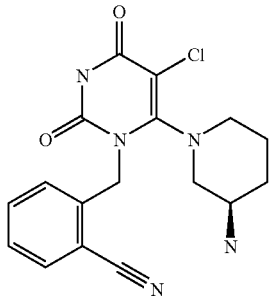

2-{6-[3(R)-Amino-piperidin-1-yl]-5-chloro-2,4-dioxo-3,4-dihydro-2H-pyrimidin-1-ylmethyl}-benzonitrile (27). Compound 4 (100 mg) in THF (2 mL) was treated with 4M HCl in dioxane (1 mL) at rt for 1 h, concentrated, and then purified by LC-MS to give the title compound. $^1$H-NMR (400 MHz, DMSO-D6): δ ppm 12.0 (s, 1H), 7.88 (d, J=7.6 Hz, 1H), 7.68 (t, J=7.7 Hz, 1H), 7.49 (t, J=7.7 Hz, 1H), 7.36 (d, J=7.8 Hz, 1H), 5.09-5.21 (m, 2H), 3.17 (m, 2H), 2.96 (t, J=11.1 Hz, 1H), 2.86 (d, J=10.6 Hz, 1H), 2.65 (m, 1H), 1.90 (d, J=11.6 Hz, 1H), 1.57 (d, J=13.1 Hz, 1H), 1.19-1.31 (m, 1H), 1.03-1.15 (m, 1H). MS (ES) [m+H] calc'd for $C_{17}H_{19}ClN_5O_2$, 360.1; found, 360.1.

Compound 28

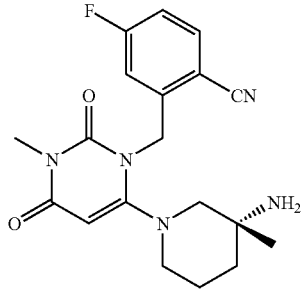

6-[3(R)-Amino-piperidin-1-yl]-1-(2,5-di-chloro-benzyl)-3-methyl-1H-pyrimidine-2,4-dione (28). The title compound was prepared from compound 1 using the same procedures as in the preparation of compound 10, except that 2,5-di-chloro-benzyl bromide was used in the place of 2-bromo-5-fluoro-benzyl bromide. $^1$H-NMR (400 MHz, CDCl$_3$-CD$_3$OD 10:1): δ ppm 7.50 (d, J=8.6 Hz, 1H), 7.39 (dd, J=8.3, 2.526 Hz, 1H), 7.22 (d, J=2.5 Hz, 1H), 5.41 (s, 1H), 5.01-4.93 (ABq, J=41.9, 16.2 Hz, 2H), 3.25 (m, 2H), 3.10 (s, 3H), 2.85 (m, 1H), 2.76 (m, 1H), 2.67 (m, 1H), 1.91 (m, 1H), 1.75 (m, 1H), 1.45 (m, 2H). MS (ES) [m+H] calc'd for $C_{17}H_{21}Cl_2N_4O_2$, 383.1; found 383.1.

Compound 29

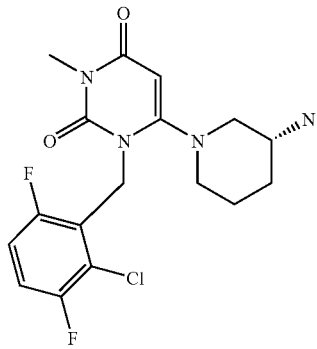

6-[3(R)-Amino-piperidin-1-yl]-1-(2-chloro-3,6-difluoro-benzyl)-3-methyl-1H-pyrimidine-2,4-dione (29). The title compound was prepared from compound 1 using the same procedures as in the preparation of compound 10, except that 2-chloro-3,6-di-fluoro-benzyl bromide was used in the place of 2-bromo-5-fluoro-benzyl bromide. $^1$H NMR (400 MHz, CDCl$_3$-CD$_3$OD 10:1) δ ppm 6.98-7.06 (m, 2H), 6.90 (m, 2H), 5.31 (s, 1H), 5.01-5.20 (ABq, J=24.2, 14.4 Hz, 2H), 3.28-3.37 (m, 2H) 3.13 (s, 3H), 3.01-2.94 (m, 1H), 2.6-2.9 (m, 2H), 2.10 (m, 1H), 1.92 (m, 2H), 1.73 (s, 1H), 1.6-1.75 (m, 2H). MS (ES) [m+H] calc'd for $C_{17}H_{20}ClF_2N_4O_2$, 385.1; found 385.1.

Compound 30

(R)-2-((6-(3-amino-3-methylpiperidin-1-yl)-3-methyl-2,4-dioxo-3,4-dihydropyrimidin-1(2H)-yl)methyl)-4-fluorobenzonitrile (30). 2-(6-Chloro-3-methyl-2,4-dioxo-3,4-dihydro-2H-pyrimidin-1-ylmethyl)-4-fluoro-benzonitrile (300 mg, 1.0 mmol), (R)-3-amino-3-methyl-piperidine dihydrochloride (266 mg, 1.4 mmol) and sodium bicarbonate (500 mg, 5.4 mmol) were stirred in a sealed tube in EtOH (3 mL) at 100° C. for 2 hrs. The final compound was obtained as TFA salt after HPLC purification. $^1$H-NMR (400 MHz, CD$_3$OD): δ. 7.78-7.83 (m, 1H), 7.14-7.26 (m, 2H), 5.47 (s, 1H), 5.12-5.36 (ABq, 2H, J=105.2, 15.6 Hz), 3.21 (s, 1H), 2.72-3.15 (m, 4H), 1.75-1.95 (m, 4H), 1.39 (s, 3H). MS (ES) [m+H] calc'd for C19H22FN5O2, 372.41; found, 372.41.

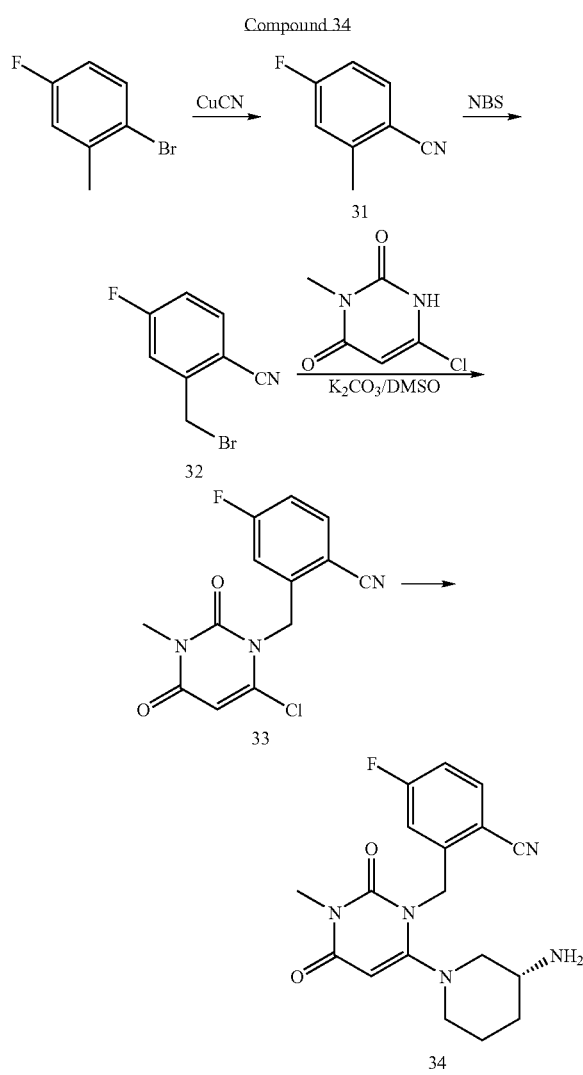

4-Fluoro-2-methylbenzonitrile (31). A mixture of 2-bromo-5-fluorotoluene (3.5 g, 18.5 mmol) and CuCN (2 g, 22 mmol) in DMF (100 mL) was refluxed for 24 hours. The reaction was diluted with water and extracted with hexane. The organics were dried over MgSO$_4$ and the solvent removed to give product 31 (yield 60%). $^1$H-NMR (400 MHz, CDCl$_3$): δ 7.60 (dd, J=5.6, 8.8 Hz, 1H), 6.93-7.06 (m, 2H), 2.55 (s, 3H).

2-Bromomethyl-4-fluorobenzonitrile (32). A mixture of 4-fluoro-2-methylbenzonitrile (2 g, 14.8 mmol), NBS (2.64 g, 15 mmol) and AIBN (100 mg) in CCl$_4$ was refluxed under nitrogen for 2 hours. The reaction was cooled to room temperature. The solid was removed by filtration. The organic solution was concentrated to give crude product as an oil, which was used in the next step without further purification. $^1$H-NMR (400 MHz, CDCl$_3$): δ 7.68 (dd, J=5.2, 8.4 Hz, 1H), 7.28 (dd, J=2.4, 8.8 Hz, 1H), 7.12 (m, 1H), 4.6 (s, 2H).

2-(6-Chloro-3-methyl-2,4-dioxo-3,4-dihydro-2H-pyrimidin-1-ylmethyl)-4-fluoro-benzonitrile (33). A mixture of crude 3-methyl-6-chlorouracil (0.6 g, 3.8 mmol), 2-bromomethyl-4-fluorobenzonitrile (0.86 g, 4 mmol) and K$_2$CO$_3$ (0.5 g, 4 mmol) in DMSO (10 mL) was stirred at 60° C. for 2 hours. The reaction was diluted with water and extracted with EtOAc. The organics were dried over MgSO$_4$ and the solvent removed. The residue was purified by column chromatography. 0.66 g of the product was obtained (yield: 60%). $^1$H-NMR (400 MHz, CDCl$_3$): δ 7.73 (dd, J=7.2, 8.4 Hz, 1H), 7.26 (d, J=4.0 Hz, 1H), 7.11-7.17 (m, 1H), 6.94 (dd, J=2.0, 9.0 Hz, 1H), 6.034 (s, 2H), 3.39 (s, 3H). MS (ES) [m+H] calc'd for C$_{13}$H$_9$ClFN$_3$O$_2$, 293.68; found 293.68.

2-[6-(3-Amino-piperidin-1-yl)-3-methyl-2,4-dioxo-3,4-dihydro-2H-pyrimidin-1-ylmethyl]-4-fluoro-benzonitrile (34). 2-(6-Chloro-3-methyl-2,4-dioxo-3,4-dihydro-2H-pyrimidin-1-ylmethyl)-4-fluoro-benzonitrile (300 mg, 1.0 mmol), (R)-3-amino-piperidine dihydrochloride (266 mg, 1.5 mmol) and sodium bicarbonate (500 mg, 5.4 mmol) were stirred in a sealed tube in EtOH (3 mL) at 100° C. for 2 hrs. The final compound was obtained as TFA salt after HPLC purification. $^1$H-NMR (400 MHz, CD$_3$OD): δ. 7.77-7.84 (m, 1H), 7.16-7.27 (m, 2H), 5.46 (s, 1H), 5.17-5.34 (ABq, 2H, J=35.2, 15.6 Hz), 3.33-3.47 (m, 2H), 3.22 (s, 3H), 2.98-3.08 (m, 1H), 2.67-2.92 (m, 2H), 2.07-2.17 (m, 1H), 1.82-1.92 (m, 1H), 1.51-1.79 (m, 2H). MS (ES) [m+H] calc'd for C$_{18}$H$_{20}$FN$_5$O$_2$, 357.38; found, 357.38.

The TFA salt (34) was suspended in DCM, and then washed with saturated Na$_2$CO$_3$. The organic layer was dried and removed in vacuo. The residue was dissolved in acetonitrile and HCl in dioxane (1.5 eq.) was added at 0° C. The HCl salt was obtained after removing the solvent. $^1$H-NMR (400 MHz, CD$_3$OD): δ. 7.77-7.84 (m, 1H), 7.12-7.26 (m, 2H), 5.47 (s, 1H), 5.21-5.32 (ABq, 2H, J=32.0, 16.0 Hz), 3.35-3.5 (m, 2H), 3.22 (s, 3H), 3.01-3.1 (m, 1H), 2.69-2.93 (m, 2H), 2.07-2.17 (m, 1H), 1.83-1.93 (m, 1H), 1.55-1.80 (m, 2H). MS (ES) [m+H] calc'd for C$_{18}$H$_{20}$FN$_5$O$_2$, 357.38; found, 357.38.

The product was also converted to a variety of corresponding acid addition salts. Specifically, the benzonitrile product (approximately 10 mg) in a solution of MeOH (1 mL) was treated with various acids (1.05 equivalents). The solutions were allowed to stand for three days open to the air. If a precipitate formed, the mixture was filtered and the salt dried. If no solid formed, the mixture was concentrated in vacuo and the residue isolated. In this way, salts of 34 were prepared from the following acids: benzoic, p-toluenesulfonic, succinic, R-(−)-Mandelic and benzenesulfonic. The succinate was found to be crystalline as determined by x-ray powder diffraction analysis.

In addition, the methanesulfonate salt was prepared as follows. A 10.5 g aliquot of the benzonitrile product was mixed with 400 mL of isopropylacetate. The slurry was heated to 75° C. and filtered through #3 Whatman filter paper. The solution was heated back to 75° C. and a 1M solution of methanesulfonic acid (30.84 mL) was added slowly over 10 minutes while stirring. The suspension was cooled to room temperature at a rate of about 20° C./hr. After 1 hr at room temperature, the solid was filtered and dried in an oven overnight to obtain the methanesulfonate salt.

Examples of In Vitro Assays

The protease inhibitory activities of DPP-IV inhibitors can be readily determined by methods known to those of ordinary skill in the art since suitable in vitro assays for measuring protease activity and the inhibition thereof by test compounds are known. Examples of assays that may be used for measuring protease inhibitory activity and selectivity are set forth below.

DPP-IV Assay

Solutions of test compounds in varying concentrations (≦10 mM final concentration) were prepared in Dimethyl Sulfoxide (DMSO) and then diluted into assay buffer comprising: 20 mM Tris, pH 7.4; 20 mM KCl; and 0.1 mg/mL BSA. Human DPP-IV (0.1 nM final concentration) was added to the dilutions and pre-incubated for 10 minutes at ambient temperature before the reaction was initiated with A-P-7-amido-4-trifluoromethylcoumarin (AP-AFC; 10 µM final concentration). The total volume of the reaction mixture was 10-100 µL depending on assay formats used (384 or 96 well plates). The reaction was followed kinetically (excitation λ=400 nm; emission λ=505 nm) for 5-10 minutes or an endpoint was measured after 10 minutes. Inhibition constants (IC$_{50}$) were calculated from the enzyme progress curves using standard mathematical models.

FAPα Assay

Solutions of test compounds in varying concentrations (≦110 mM final concentration) were prepared in Dimethyl Sulfoxide (DMSO) and then diluted into assay buffer comprising: 20 mM Tris, pH 7.4; 20 mM KCl; and 0.1 mg/mL BSA. Human FAPα (2 nM final concentration) was added to the dilutions and pre-incubated for 10 minutes at ambient temperature before the reaction was initiated with A-P-7-amido-4-trifluoromethylcoumarin (AP-AFC; 40 µM final concentration). The total volume of the reaction mixture was 10-100 µL depending on assay formats used (384 or 96 well plates). The reaction was followed kinetically (excitation λ=400 nm; emission λ=505 nm) for 5-10 minutes or an endpoint was measured after 10 minutes. Inhibition constants (IC$_{50}$) were calculated from the enzyme progress curves using standard mathematical models.

PREP Assay

Solutions of test compounds in varying concentrations (≦10 mM final concentration) were prepared in Dimethyl Sulfoxide (DMSO) and then diluted into assay buffer comprising: 20 mM Sodium Phosphate, pH 7.4; 0.5 mM EDTA; 0.5 mM DTT; and 0.1 mg/mL BSA. PREP (EC3.4.21.26 from *Flavobacterium meningosepticum;* 0.2 nM final concentration) was added to the dilutions. The PREP and compound were pre-incubated for 10 minutes at ambient temperature before the reaction was initiated with Z-G-P-AMC (10 µM final concentration). The total volume of the reaction mixture was 10-100 µL depending on assay formats used (384 or 96 well plates). The reaction was followed kinetically (excitation λ=375 nm; emission λ=460 nm) for 10 minutes or an endpoint was measured after 10 minutes. Inhibition constants (IC$_{50}$) were calculated from the enzyme progress curves using standard mathematical models.

Tryptase Assay

Solutions of test compounds in varying concentrations (≦10 mM final concentration) were prepared in Dimethyl Sulfoxide (DMSO) and then diluted into assay buffer comprising: 100 mM Hepes, pH 7.4; 0.01% Brij35; and 10% glycerol. Tryptase (rhLung beta; 0.1 nM final concentration) was added to the dilutions and pre-incubated with compound for 10 minutes at ambient temperature. The enzymatic reaction was initiated with 25 µM Z-lys-SBzl and 400 µM DTNB. The total volume of the reaction mixture was 100 µL in Costar λ/2 96 well plates. The reaction was followed calorimetrically (λ=405 nm) for 10 minutes. Inhibition constants (IC$_{50}$) were calculated from the enzyme progress curves using standard mathematical models.

Compounds of the invention were tested according to the above-described assays for protease inhibition and observed to exhibit selective DPP-IV inhibitory activity. For example, compounds of the invention were found to inhibit DPP-IV activity at concentrations that are at least 50 fold less than those concentrations required to produce an equiactive inhibition of protease activity for FAPα. The apparent inhibition constants (K$_i$) for compounds of the invention, against DPP-IV, were in the range from about $10^{-9}$M to about $10^{-5}$M.

It will be apparent to those skilled in the art that various modifications and variations can be made to the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound having the formula

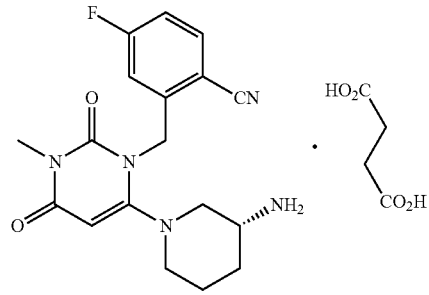

wherein the compound is in crystalline form.

2. A compound according to claim 1, wherein the compound is in the same crystalline form as is formed when the compound is crystallized from methanol.

3. A method comprising:
crystallizing a compound having the formula

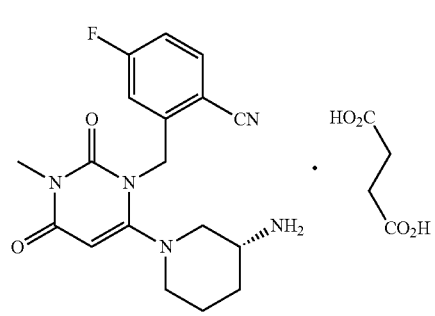

wherein the crystallization is performed in methanol.

4. A pharmaceutical composition comprising:
a compound having the formula

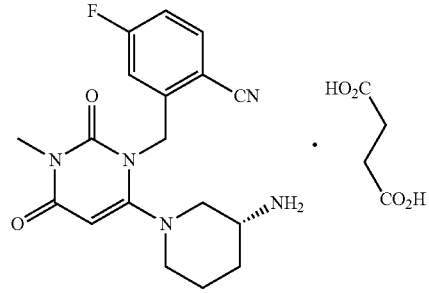

wherein the compound is in crystalline form; and
one or more pharmaceutical carriers,
wherein the pharmaceutical composition is in the form of a pill, capsule, tablet, wafer, powder or granule.

5. A pharmaceutical composition according to claim 4, wherein the compound is in the same crystalline form as is formed when the compound is crystallized from methanol.

6. A pharmaceutical composition according to claim 4, wherein the pharmaceutical composition is a pill or capsule adapted for oral administration.

7. A pharmaceutical composition according to claim 4, wherein the pharmaceutical composition is in an oral dosage form selected from the group consisting of pills, tablets, capsules, wafers, powders, and granules.

8. A pharmaceutical composition according to claim 4, wherein the pharmaceutical composition is adapted for topical or transdermal administration.

9. A pharmaceutical composition according to claim 4, wherein the pharmaceutical composition is in a pulmonary dosage form.

10. A kit comprising:
    a pharmaceutical composition comprising
        a compound having the formula

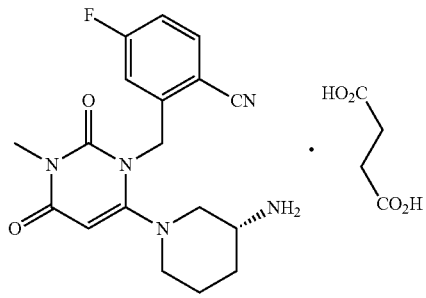

wherein the compound is in crystalline form, and
one or more pharmaceutical carriers; and
instructions which comprise one or more forms of information selected from the group consisting of indicating a disease state for which the pharmaceutical composition is to be administered selected from the group consisting of diabetes, rheumatoid arthritis and breast cancer, storage information for the pharmaceutical composition, dosing information and instructions regarding how to administer the composition.

11. A kit according to claim 10, wherein the kit comprises the pharmaceutical composition in a multiple dose form.

12. An article of manufacture comprising:
    a pharmaceutical composition comprising
        a compound having the formula

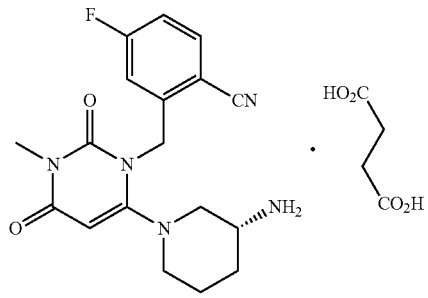

wherein the compound is in crystalline form, and
one or more pharmaceutical carriers; and
packaging materials.

13. An article of manufacture according to claim 12, wherein the packaging material comprises a container for housing the pharmaceutical composition.

14. An article of manufacture according to claim 12, wherein the container comprises a label indicating one or more members of the group consisting of a disease state for which the composition is to be administered selected from the group consisting of Type I diabetes, Type II diabetes, rheumatoid arthritis and breast cancer, storage information, dosing information and/or instructions regarding how to administer the composition.

15. An article of manufacture according to claim 12, wherein the pharmaceutical composition is in a multiple dose form.

* * * * *